(12) United States Patent
List

(10) Patent No.: US 10,697,970 B2
(45) Date of Patent: Jun. 30, 2020

(54) S100A9 LEVELS FOR PREDICTING LENALIDOMIDE AND ERYTHROPOIETIN RESPONSIVENESS

(71) Applicant: H. LEE MOFFITT CANCER CENTER AND RESEARCH INSTITUTE, INC., Tampa, FL (US)

(72) Inventor: Alan F. List, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 37 days.

(21) Appl. No.: 15/570,916

(22) PCT Filed: Apr. 29, 2016

(86) PCT No.: PCT/US2016/030253
§ 371 (c)(1),
(2) Date: Oct. 31, 2017

(87) PCT Pub. No.: WO2016/179036
PCT Pub. Date: Nov. 10, 2016

(65) Prior Publication Data
US 2018/0292411 A1   Oct. 11, 2018

Related U.S. Application Data

(60) Provisional application No. 62/155,994, filed on May 1, 2015, provisional application No. 62/165,032, filed on May 21, 2015, provisional application No. 62/307,960, filed on Mar. 14, 2016.

(51) Int. Cl.
| | |
|---|---|
| *A61K 38/18* | (2006.01) |
| *G01N 33/574* | (2006.01) |
| *G01N 33/68* | (2006.01) |
| *A61K 31/454* | (2006.01) |
| *A61K 38/19* | (2006.01) |
| *A61K 38/22* | (2006.01) |

(52) U.S. Cl.
CPC ..... *G01N 33/57426* (2013.01); *A61K 31/454* (2013.01); *A61K 38/1816* (2013.01); *A61K 38/193* (2013.01); *A61K 38/22* (2013.01); *G01N 33/574* (2013.01); *G01N 33/57407* (2013.01); *G01N 33/57484* (2013.01); *G01N 33/6893* (2013.01); *G01N 2333/4703* (2013.01); *G01N 2333/525* (2013.01); *G01N 2800/52* (2013.01)

(58) Field of Classification Search
CPC ........... G01N 2800/52; G01N 2800/24; G01N 33/574; G01N 33/57407; G01N 33/6872; G01N 2333/525; G01N 2333/435; G01N 2333/46; G01N 33/57484; G01N 33/48; G01N 33/53; G01N 33/50; G01N 33/564; G01N 2800/22; G01N 33/57496; G01N 33/6893

See application file for complete search history.

(56) References Cited

U.S. PATENT DOCUMENTS

2011/0172273 A1   7/2011 Zeldis

FOREIGN PATENT DOCUMENTS

WO   2015003149 A2   1/2015

OTHER PUBLICATIONS

Basiorka et al. Activation of redox-sensitive inflammasomes underlies the biologic phenotype of myelodysplastic syndromes. Leukemia Res 39(Suppl 1): S14, Apr. 2015; 1 page.*
Chen et al. Induction of myelodysplasia by myeloid-derived suppressor cells. J Clin Invest 123(11): 4595-4611, 2013.*
Ebert et al. An erythroid differentiation signature predicts response to lenalidomide in myelodysplastic syndrome. PLoS Med 5(2): e35, 2008.*
Foell et al. Proinflammatory s100 proteins in arthritis and autoimmune disease. Arthritis Rheunnat 50(12): 3762-3771, 2004.*
Fuchs, O. "Treatment of myelodysplastic syndrome and acute myeloid leukemia by immunomodulatory and epigenetic drugs" in Leukemia, IntechOpen 2013, pp. 157-193.*
Komrokji et al. Deletion 5q MDS: molecular and therapeutic implications. Best Practice Res Clin Haematol 26: 365-275, 2013.*
Nirmala et al. Biomarkers in systemic juvenile idiopathic arthritis : a comparison with biomarkers in cryopyrin associated periodic syndromes. Curr Opin Rheumatol 26(5): 543-552, 2014.*
Porwit et al. The AML-MDS interface-leukemic transformation in myelodysplastic syndromes. J Hematopathol 4: 69-79, 2011.*
Tian et al. TNF-alpha, a good or bad factor in hematological diseases? Stem Cell Investig 1: 12, 2014.*
Wang et al. Screening for feature genes associated with hereditary hemochromatosis and functional analysis with DNA microarrays. Genet Mol Res 12(4): 6240-6248, 2013.*
Wei et al. MDS genetic damage is linked to inflammaging induced bone marrow hyperglycemia. Leukemia Res 39(Suppl 1): S13, Apr. 2015; 1 page.*
Wittkowski et al. MRP8 and MRP14, phagocyte-specific danger signals, are sensitive biomarkers of disease activity in cryopyrin-associated periodic syndromes. Annals Rheumat Dis 70(12): 2075-2081, 2011.*

(Continued)

*Primary Examiner* — Bridget E Bunner
(74) *Attorney, Agent, or Firm* — Thomas|Horstemeyer, LLP

(57) ABSTRACT

A method is disclosed for diagnosing multiple myeloma or myelodysplastic syndrome (MDS) in a subject and/or predicting the responsiveness of a patient with a multiple myeloma or MDS to lenalidomide treatment, erythropoietin treatment, or a combination thereof. The method involves assaying a biological sample from the subject, such as a blood, serum, or plasma sample, for s100A9 protein levels, TNF? levels, or a combination thereof wherein elevated levels of s100A9 in the biological sample and/or reduced levels of TNF? levels is an indication of MDS in the subject and/or that the patient will be responsive.

9 Claims, 67 Drawing Sheets

Specification includes a Sequence Listing.

(56) References Cited

OTHER PUBLICATIONS

International Search Report for PCT/US2016/030253 dated Aug. 5, 2016.
List, et al., "Efficacy of Lenalidomide in Myelodysplastic Syndromes", The New England Journal of Medicine, Feb. 10, 2005, 352;6, pp. 549-557.

* cited by examiner

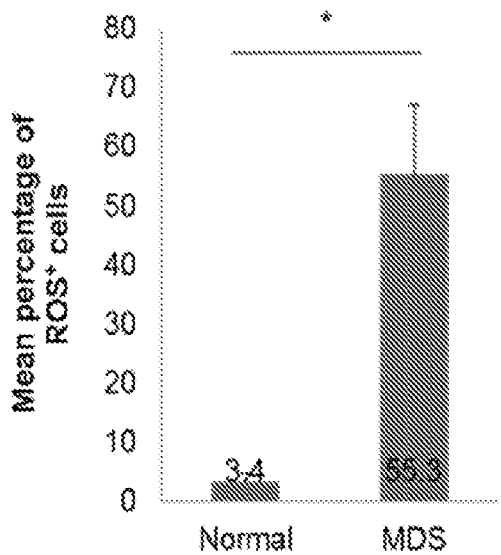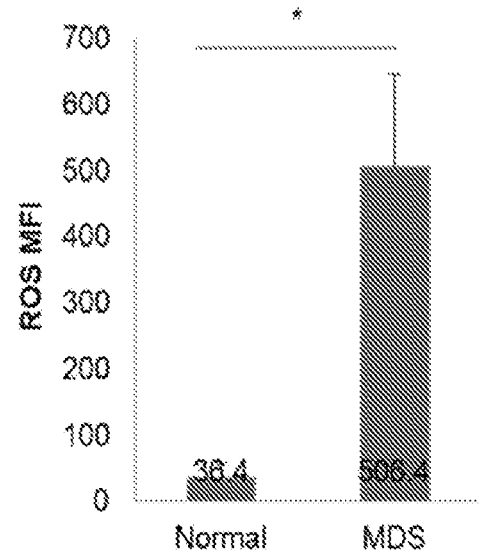
FIGURE 6A                    FIGURE 6B

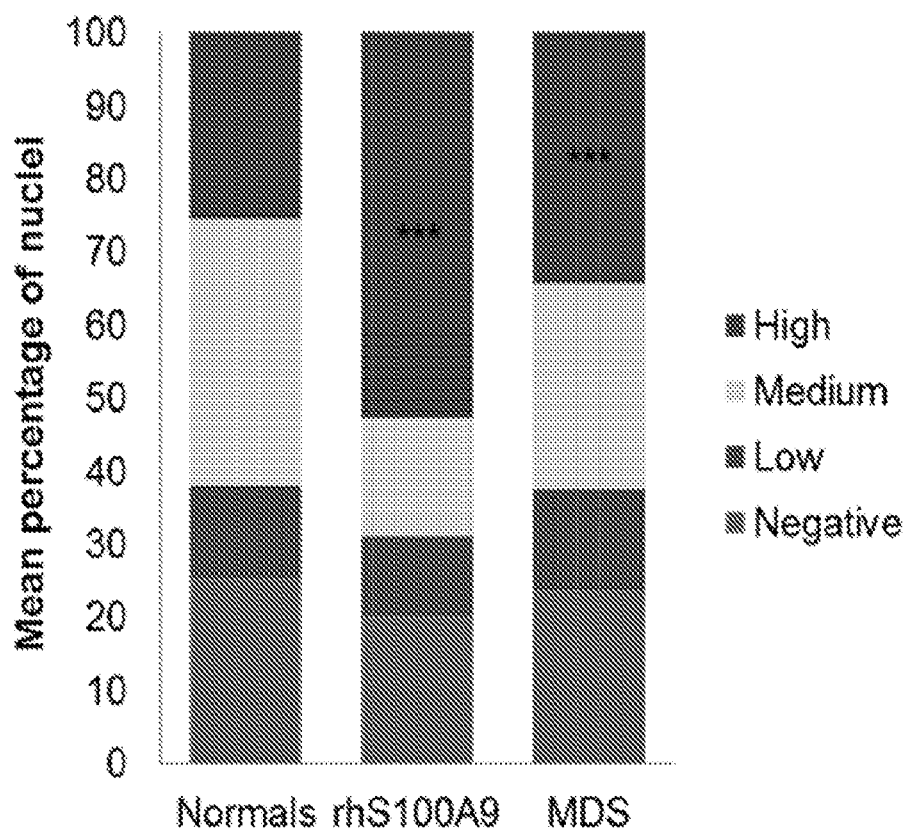
FIGURE 6D
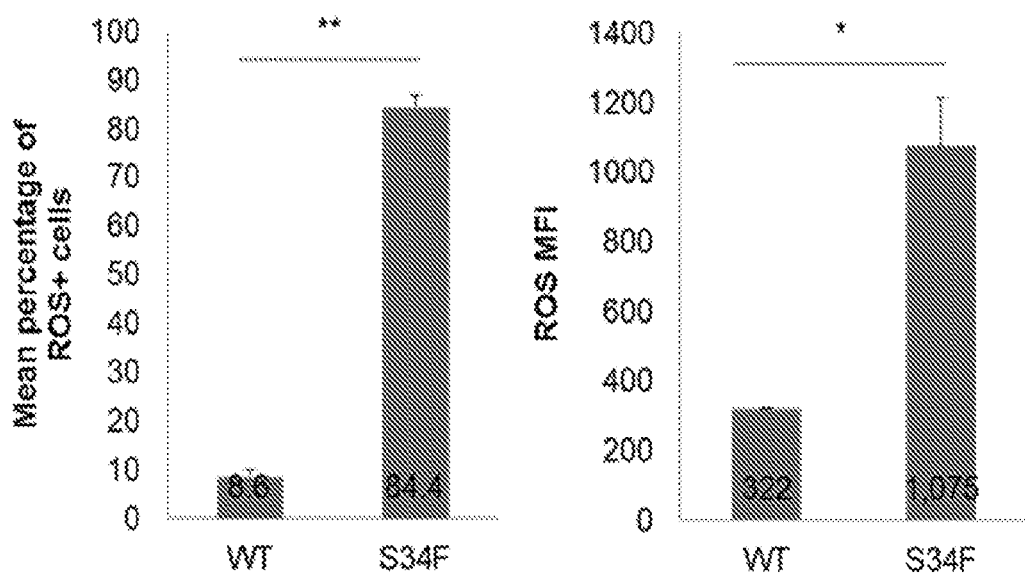
FIGURE 6E
FIGURE 6F

| | a-Caspase-1 MFI | % a-Caspase-1+ |
|---|---|---|
| Control | 57.2 | 2.99 |
| 1ug S100A9 | 88.9 | 15.4 |
| 5ug S100A9 | 126 | 28.4 |
| 10ug S100A9 | 608 | 79 |
| 25ug S100A9 | 1192 | 96.4 |

| | a-Caspase-1 MFI | % a-Caspase-1+ |
|---|---|---|
| Control | 95.7 | 20.3 |
| LPS | 128 | 41.4 |
| 24h S100A9 | 327 | 58.1 |
| 48h S100A9 | 330 | 58.5 |
| 72h S100A9 | 589 | 76.5 |

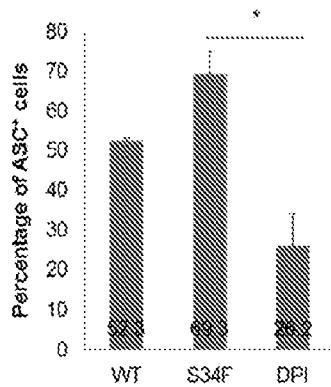
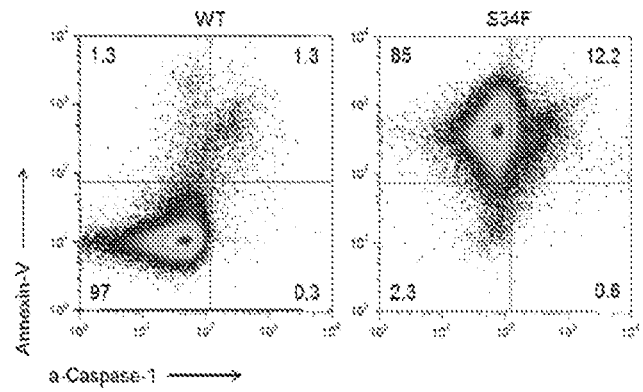
*FIGURE 15B*          *FIGURE 15C*
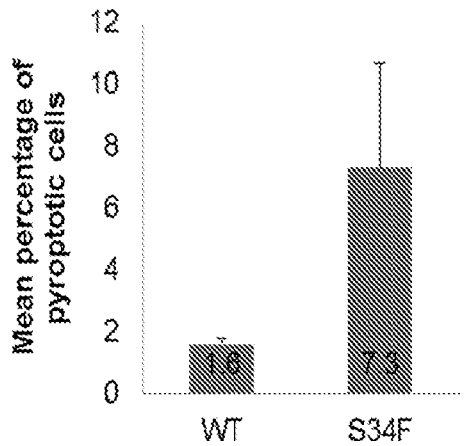
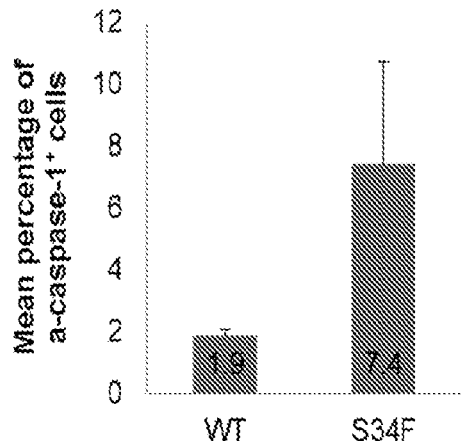
*FIGURE 15D*          *FIGURE 15E*
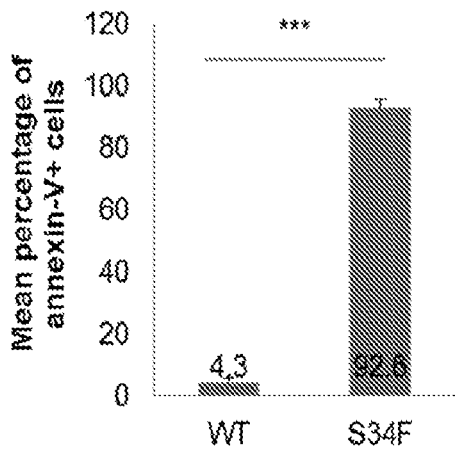
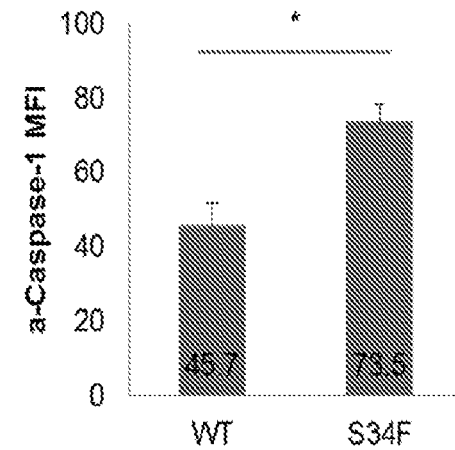
*FIGURE 15F*          *FIGURE 15G*

SEQUENCE LISTING

```
<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
```

<223> OTHER INFORMATION: Synthetic construct

<400> SEQUENCE: 1
tgagcagcca gatggtagag c                                              21

<210> SEQ ID NO 2
<211> LENGTH: 24
<212> TYPE: DNA
<213> ORGANISM: Artificial Sequence
<220> FEATURE:
<223> OTHER INFORMATION: Synthetic construct

<400> SEQUENCE: 2
gtgaggcggt tgtagaagag tttc                                           24

<210> SEQ ID NO 3
<211> LENGTH: 20
<212> TYPE: DNA
<213> ORGANISM: Artificial Sequence
<220> FEATURE:
<223> OTHER INFORMATION: Synthetic construct

<400> SEQUENCE: 3
ctcttcgagg cacaaggcac                                                20

<210> SEQ ID NO 4
<211> LENGTH: 20
<212> TYPE: DNA
<213> ORGANISM: Artificial Sequence
<220> FEATURE:
<223> OTHER INFORMATION: Synthetic construct

<400> SEQUENCE: 4
actgcctgga cagtcagcaa                                                20

<210> SEQ ID NO 5
<211> LENGTH: 20
<212> TYPE: DNA
<213> ORGANISM: Artificial Sequence
<220> FEATURE:
<223> OTHER INFORMATION: Synthetic construct

<400> SEQUENCE: 5
tctacgttgg ccacttggga                                                20

<210> SEQ ID NO 6
<211> LENGTH: 20
<212> TYPE: DNA
<213> ORGANISM: Artificial Sequence
<220> FEATURE:
<223> OTHER INFORMATION: Synthetic construct

<400> SEQUENCE: 6
caatggggag gagaaggcgt                                                20

<210> SEQ ID NO 7
<211> LENGTH: 21
<212> TYPE: DNA
<213> ORGANISM: Artificial Sequence
<220> FEATURE:
<223> OTHER INFORMATION: Synthetic construct

<400> SEQUENCE: 7
ctcggctttg acagagtgca a                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic construct

<400> SEQUENCE: 8
ccctcccaaa ggggagacaa a                                              21

<210> SEQ ID NO 9
<211> LENGTH: 18
<212> TYPE: DNA
<213> ORGANISM: Artificial Sequence
<220> FEATURE:
<223> OTHER INFORMATION: Synthetic construct

<400> SEQUENCE: 9
gaaggtgaag gtcggact                                                  18

<210> SEQ ID NO 10
<211> LENGTH: 21
<212> TYPE: DNA
<213> ORGANISM: Artificial Sequence
<220> FEATURE:
<223> OTHER INFORMATION: Synthetic construct

<400> SEQUENCE: 10
tcacttcctg cccacagaca t                                              21

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
tgagcagggc tcgctaactc                                                20

<210> SEQ ID NO 12
<211> LENGTH: 23
<212> TYPE: DNA
<213> ORGANISM: Artificial Sequence
<220> FEATURE:
<223> OTHER INFORMATION: Synthetic construct

<400> SEQUENCE: 12
caagtcatcc tcattgccac tgt                                            23

<210> SEQ ID NO 13
<211> LENGTH: 22
<212> TYPE: DNA
<213> ORGANISM: Artificial Sequence
<220> FEATURE:
<223> OTHER INFORMATION: Synthetic construct

<400> SEQUENCE: 13
gcagccatct ttattcctga ga                                             22

<210> SEQ ID NO 14
<211> LENGTH: 22
<212> TYPE: DNA
<213> ORGANISM: Artificial Sequence
<220> FEATURE:
<223> OTHER INFORMATION: Synthetic construct

```
<400> SEQUENCE: 14
agaggtgaag gtacggctat gc                                               22

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
tctgaacccc acttcggctc                                                  20

<210> SEQ ID NO 16
<211> LENGTH: 20
<212> TYPE: DNA
<213> ORGANISM: Artificial Sequence
<220> FEATURE:
<223> OTHER INFORMATION: Synthetic construct

<400> SEQUENCE: 16
ctggttcagg gtgtctgggt                                                  20

<210> SEQ ID NO 17
<211> LENGTH: 21
<212> TYPE: DNA
<213> ORGANISM: Artificial Sequence
<220> FEATURE:
<223> OTHER INFORMATION: Synthetic construct

<400> SEQUENCE: 17
agaggaagaa ggccgaagga g                                                21

<210> SEQ ID NO 18
<211> LENGTH: 20
<212> TYPE: DNA
<213> ORGANISM: Artificial Sequence
<220> FEATURE:
<223> OTHER INFORMATION: Synthetic construct

<400> SEQUENCE: 18
gaagatggtg atgggatttc                                                  20
```

S100A9 LEVELS FOR PREDICTING LENALIDOMIDE AND ERYTHROPOIETIN RESPONSIVENESS

CROSS-REFERENCE TO RELATED APPLICATIONS

This application is the 35 U.S.C. §371 national stage application of PCT Application No. PCT/US2016/030253, filed Apr. 29, 2016, where the PCT claims benefit of U.S. Provisional Application No. 62/155,994, filed May 1, 2015, U.S. Provisional Application Serial No. 62/165,032, filed May 21, 2015, and U.S. Provisional Application Serial No. 62/307,960, filed Mar. 14, 2016, which are hereby incorporated herein by reference in their entirety.

BACKGROUND

Myelodysplastic syndromes (MDS) are hematopoietic stem cell malignancies characterized by dysplastic and ineffective hematopoiesis. MDS bone marrow precursors have a larger cell size, deregulated proliferation and maturation, and accelerated attrition by programmed cell death.

Lenalidomide (Revlimid®, Celgene Corporation, NJ, USA) (LEN) was initially intended as a treatment for multiple myeloma, but has also shown efficacy in MDS. Lenalidomide has significantly improved overall survival in myeloma (which generally carries a poor prognosis). Lenalidomide is undergoing clinical trial as a treatment for Hodgkin's lymphoma, as well as non-Hodgkin's lymphoma, chronic lymphocytic leukemia and solid tumor cancers, such as carcinoma of the pancreas. Patients with an interstitial deletion of Chromosome 5q have a high rate of response to lenalidomide, but most MDS patients lack this deletion. Approximately 25% of patients without 5q deletions also benefit from lenalidomide therapy, but response in these patients is difficult to predict. In addition, treatment with erythropoietin (EPO) may improve anemia in about 15-20% of patients with MDS. However, methods are needed to predict this responsiveness.

SUMMARY

A method is disclosed for diagnosing a myelodysplastic syndrome (MDS) in a subject. In some embodiments, the method involves assaying a sample from the subject to detect s100A9 protein levels, wherein an increase in s100A9 protein levels in the sample compared to a control is an indication of MDS. As disclosed herein, s100A9 levels can also be used to predict whether the subject has low-risk or high-risk MDS. Therefore, this can be used to select the appropriate therapy, dosage, or combination thereof. The disclosed methods can further involve treating the subject for MDS if an increase in s100A9 levels is detected. In some embodiments, the method involves treating the subject with a therapeutically effective amount of lenalidomide.

Also disclosed is a method for predicting the responsiveness of a patient with a multiple myeloma or MDS to lenalidomide treatment, erythropoietin treatment, or a combination thereof. The method involves assaying a biological sample from the subject, such as a blood, serum, or plasma sample, for s100A9 levels, TNFα levels or a combination thereof. In some embodiments, elevated levels of s100A9 in the biological sample is an indication that the patient will be responsive. In some embodiments, reduced levels of TNFα in the biological sample is an indication that the patient will be responsive. In some embodiments, the patient is suffering from anemia. In some cases, the patient has non-del5q MDS. In some cases, the patient has del5q MDS.

In some embodiments, the method further involves treating the patient with lenalidomide, erythropoietin, or a combination thereof, if s100A9 levels are elevated compared to control values. In some embodiments, the method further involves treating the patient with lenalidomide, erythropoietin, or a combination thereof, if TNFα levels are reduced compared to control values. For example, the patient can be treated with erythropoietin and granulocyte colony-stimulating factor (GCSF) if s100A9 levels are elevated compared to control values, if TNFα levels are reduced compared to control levels, or a combination thereof.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a series of bar graphs showing markedly increased expression of pyroptosis-associated genes in MNC isolated from patient MDS BM specimens (n=10 total; n=5 lower and n=5 higher-risk disease), compared to normal controls (n=5). FIG. 1B is a representative confocal fluorescence micrograph (2520× magnification, 7.5 μm scale) of a-caspase-1 and NLRP3 expression in MDS versus normal BM-MNC. DAPI, a-caspase-1, NLRP3; merged image shows inflammasome formation. FIG. 1C shows quantitative analysis of a-caspase-1/NLRP3 confocal images of BM-MNC isolated from lower-risk (n=7) and higher-risk (n=3) MDS patients, and normal donors (n=6). MDS patient specimens have significantly increased expression of a-caspase-1 and NLRP3 proteins, accompanied by co-localization, confirming inflammasome assembly. FIG. 1D contains representative scatter plots of pyroptotic cells (a-caspase-1$^+$/annexin-V$^+$) by flow cytometry in four phenotypically distinct hematopoietic lineages and cell types: stem cells (CD34$^+$CD38$^-$), progenitor cells (CD34$^+$CD38$^+$), immature myeloids (CD33$^+$), and erythroids (CD71$^+$). FIG. 1E shows quantitation of the mean percentage of pyroptotic cells by hematopoietic lineage in MDS (n=8) versus normal donors (n=5). FIG. 1F shows comparison of the mean percentage of pyroptotic versus apoptotic cells (a-caspase-3/7$^+$/annexin-V$^+$) by hematopoietic lineage in lower-risk MDS specimens (n=5). FIGS. 1G and 1H show mean percentage of pyroptoic cells when lower-risk MDS BM-MNC (n=3) were transfected by lentivirus with shRNAs targeting CASP1 (FIG. 1G) or CASP3 (FIG. 1H). Suppression of caspase-1 resulted in a significant reduction in the percentage of pyroptotic cells, whereas suppression of caspase-3 had no significant effect, confirming caspase-1 dependence. Error bars: SE, *$p<0.05$, $p<0.01$, and *$p<0.001$.

FIG. 2A shows ELISA assessment of BM plasma concentration of S100A9 in normal donors (n=12) versus lower-risk (n=33) and higher-risk (n=27) MDS. FIG. 2B shows BM plasma concentration of HMGB1 assessed by ELISA in normal donors (n=11) and MDS (n=55). FIG. 2C shows qPCR analysis of S100A9 mRNA in normal (n=2) versus lower-risk MDS (n=8). FIG. 2D shows HMGB1 transcript levels in normal (n=6) versus MDS BM-MNC (n=10). FIG. 2E shows changes in pyroptosis-related gene expression assessed by qPCR in untreated normal BM-MNC (n=3), normal BM-MNC treated with 1 μg/mL rhS100A9 for 24 hours (n=2), and in MDS patient specimens (n=5). FIG. 2F shows representative micrograph (2520× magnification, 7.5 μm scale) depicting inflammasome formation in normal, untreated BM-MNC or normal BM-MNC treated with 5 μg/mL rhS100A9 for 24 hours. DAPI a-caspase-1, and NLRP3; merged images show formation of inflammasome complexes. FIG. 2G shows quantitative analysis of a-caspase-1/NLRP3 confocal images from normal donors (n=6), normal BM-MNC treated with 5 μg/mL rhS100A9 (n=2), and MDS patients (n=10). Error bars: SE, *p<0.05, p<0.01, and *p<00.001.

FIG. 3A shows mean cell area quantified following analysis of a-caspase-1/NLRP3 confocal images of BM from normal donor (n=6), lower-risk (n=7), and higher-risk MDS patient specimens (n=3). Mean cell area is augmented in MDS irrespective of risk score. FIG. 3B shows NLRP3 MFI and cell area are correlated in lower-risk MDS patients (r=0.49, n=7). FIG. 3C shows U937 cells incubated with 12.5 μg/mL ethidium bromide (EB), and treated with 5 μg/mL rhS100A9 or media alone. Uptake of EB is depicted in green (680× magnification, 25 μm scale). FIG. 3D shows BM-MNC from normal donors (n=3) and MDS patients (n=3) incubated with autologous BM plasma for 24 hours. 12.5 μg/mL EB was then added to the cells, and dye incorporation measured by flow cytometry at 5 minute intervals. FIG. 3E shows Left to right, photomicrograph images from normal donors illustrating normal red blood cell (RBC, 7.0 μm) followed by normal erythroid lineage maturation of nucleated BM precursors with corresponding cell diameter. FIG. 3F shows corresponding images from MDS BM aspirates, demonstrating an oval macrocyte (RBC, 9.1 μm) followed by dysplastic and megaloblastic erythroid lineage maturation. FIG. 3G shows normal myelocyte. FIG. 3H shows enlarged dysplastic myelocyte with mild hypogranulation in MDS. FIGS. 3I and 3H show comparison of mean cell diameter in normal (n=4) versus MDS (n=4) BM during erythroid (FIG. 3I) and myeloid (FIG. 3J) lineage maturation. Left to right, maturation is depicted as most to least mature cell populations. Error bars: SE, *p<0.05, p<0.01, and *p<0.001.

FIG. 4A shows reduction in the fraction of pyroptotic BM cells from a MDS patient following treatment with 0.5 μg CD33-IgG$_1$ or 0.1 μM IRAK4 inhibitor. Values are normalized to autologous BM plasma-incubated MDS BM-MNC. FIG. 4B shows quantitation of the mean percentage of pyroptotic cells in each respective lineage in MDS BM-MNC incubated with autologous BM plasma and either 0.5 μg CD33-IgG$_1$ or 0.1 μM IRAK4 inhibitor for 24 hours (n=4). FIG. 4C shows BM-MNC isolated from lower-risk MDS patients (n=5) were treated for 24 hours with CD33-IgG$_1$, and pyroptosis-related gene expression was assessed by qPCR. FIGS. 4D and 4E shows colony forming capacity was assessed in BM-MNC from MDS patient specimens (n=3) that were treated with increasing concentrations of CD33-IgG$_1$ (FIG. 4D), or with the inflammasome inhibitor MCC950 (FIG. 4E). Error bars: SE.

FIG. 5A shows quantitative analysis of a-caspase-1 MFI, NLRP3 MFI, co-localization, and cell area from confocal images of BM cells isolated from WT (n=2), 2 month (n=4), 6 month (n=5), and 11 month (n=4) old S100A9Tg mice. FIG. 5B shows representative micrograph (2520× magnification, 7.5 μm scale) of a-caspase-1 and NLRP3 protein expression in WT BM cells treated for 24 hours with 5 μg/mL S100A9, and of BM cells from S100A9Tg mice. DAPI, a-caspase-1, and NLRP3; merged image illustrates inflammasome formation. FIG. 5C shows quantitative analysis of confocal images of BM cells isolated from WT (n=2) mice, from WT BM cells treated for 24 hours with 5 μg/mL S100A9, or from BM cells from S100A9Tg mice (n=13). FIGS. 5D and 5E show representative scatter plots of pyroptotic (FIG. 5D) and apoptotic (FIG. 5E) KLS (c-Kit$^+$Lin$^-$Sca-1$^+$) cells isolated from WT and transgenic mice. FIG. 5F shows mean percentage of pyroptotic versus apoptotic KLS cells in WT (n=6) and S100A9Tg mice (n=6). FIG. 5G shows mean percentage of total a-caspase-1$^+$ and a-caspase-3/7$^+$ KLS cells isolated from WT (n=6) and S100A9Tg mice (n=6). FIG. 5H shows at six months of age, S100A9Tg transgenic mice treated every other day with 50 mg/kg of the inflammasome inhibitor ICTA by oral gavage for a total of eight weeks. Shown are changes in hemoglobin, white blood cells (WBC), RBC and platelet counts in WT (n=4) and S100A9Tg (n=5) versus S100A9Tg mice treated with ICTA (n=5). Error bars: SE, *p<0.05, p<0.01, and *p<00.001.

FIGS. 6A to 6H show S100A9 and MDS gene mutations induce ROS through NADPH oxidase to activate β-catenin. FIG. 6A shows the percentage of ROS positive cells and b, ROS MFI were assessed by flow cytometry in BM-MNC isolated from MDS patients (n=5) and normal donors (n=2). FIG. 6C shows representative micrograph (2520× magnification, 7.5 μm scale) of β-catenin expression in normal BM-MNC (n=3), normal BM-MNC treated with 5 μg/mL rhS100A9 (n=3) and MDS patients (n=6). DAPI and β-catenin are individually depicted, and the merged image illustrates nuclear localization of β-catenin. FIG. 6D shows quantitation and scoring of β-catenin confocal images based on the presence of no, low, medium, or high nuclear β-catenin in normal BM-MNC, rhS100A9 treated normal BM cells, and MDS patients. FIG. 6E shows mean percentage of ROS positive cells and FIG. 6F shows ROS MFI assessed by flow cytometry in U2AF1 S34F mutant expressing TF-1 cells and corresponding WT cells. Data are representative of three independent experiments. FIG. 6G shows representative micrograph (1890× magnification, 10 μm scale) illustrating β-catenin expression in U2AF1WT cells, cells expressing S34F, or S34F-expressing mutant cells treated with NAC or the NADPH oxidase inhibitor DPI for 24 hours prior to staining. FIG. 6H shows quantitation and scoring of β-catenin confocal images based on the presence of no, low, medium, or high nuclear β-catenin. Error bars: SE, *p<0.05, p<0.01, and *p<0.001.

FIGS. 7A to 7C are bar graph showing mean percentage of total a-caspase-1$^+$ (FIG. 7A), annexin-V$^+$ (FIG. 7B), and a-caspase-3/7$^+$ (FIG. 7C) cells assessed by hematopoietic lineage. Data are representative of five normal donors and eight lower-risk MDS patients. Error bars: SE, *p<0.05 and **p<0.01.

FIG. 9A shows U937 monocytic cells were treated with increasing concentrations of rhS100A9 for 24 hours, resulting in a concentration-dependent increase in the fraction of pyroptotic cells. FIG.

9B shows active caspase-1 MFI and percent positive cells increase in a concentration-dependent manner. FIG. 9C shows U937 cells treated with 5 µg/mL rhS100A9 over time show a time-dependent increase in a-caspase-1 MFI and percent positive cells. FIG. 9D shows representative histogram depicting a-caspase-1. LPS was used as a positive control for caspase-1 activation. FIG. 9E shows representative micrograph (1890× magnification, 10 µm scale) depicting inflammasome formation in U937 cells that were untreated or treated with 5 µg/mL rhS100A9 for 24 hours. DAPI, a-caspase-1, NLRP3; merged image shows formation of inflammasome complexes. FIG. 9F shows quantitative analysis of a-caspase-1/NLRP3 confocal images of untreated and treated U937 cells. Cells were pooled for analysis. Error bars: SE, $p<0.01$ and *$p<0.001$. Data are representative of three independent experiments.

FIG. 11A is representative histogram. FIG. 11B shows mean percentage of S100A9$^+$ cells and FIG. 11C shows S100A9 MFI. Error bars: SE, *$p<0.05$.

FIG. 12A shows normal BM with mild erythroid hyperplasia. The erythroid precursors show a full spectrum of maturation with mean cellular diameter recorded at different maturation stages [orthrochromic normoblast, 7.5 µm (normal reference: 6-12 µm); early to late polychromic normoblasts, 8.5 µm (normal reference: 8-14 µm); early and late basophilic normoblasts, 12.4 µm (normal reference: 12-17 µm and 10-15 µm, respectively); and promonoblasts, 15.8 µm (normal reference: 14-24 µm)]. FIG. 12B shows dysplastic erythroid precursors in the BM from an MDS patient. The erythroid precursors show obscured stage specific maturation or maturation asynchrony. Hematopoietic precursors are enlarged in size compared to the corresponding stage of maturation in normal donors [dysplastic/megaloblastoid orthrochromic normoblasts (15.8 µm), dysplastic early to late polychromic binucleated normoblast (18.2 µm), dysplastic late basophilic normoblasts (17.6 µm), and dysplastic promonoblasts (25.5 µm)]. FIG. 12C shows normal BM with complete spectrum of myeloid maturation. The myeloid progenitors represent different stages of maturation with appropriate size [segmented neutrophil (10-18 µm), band form (10-20 µm), metamyelocyte (10-18 µm), myelocyte (10-20 µm), promyelocyte (12-24 µm), and myeloblasts (9-20 µm)]. FIG. 12D shows enlarged eosinophilic myelocytes measuring 23.1 µm at the maximal dimension in a background of marked dyserythropoiesis. FIG. 12E shows enlarged myelocyte with overt maturation asynchrony in a background of dyserythropoiesis in an MDS BM. The myelocyte measures 23.6 µm, which is larger than a normal myelocyte.

FIG. 13A is a representative micrograph (1890× magnification) depicting inflammasome formation in U937 cells following 24 hour treatment with vehicle or 5 µg/mL rhS100A9 alone or with ICTA (20 µg/mL). DAPI, a-caspase-1, NLRP3; merged image shows formation of inflammasome complexes. FIG. 13B shows quantitative analysis of confocal images. Error bars: SE, *$p<0.05$, $p<0.01$, *$p<0.001$.

FIGS. 14A and 14B show the percentage of ROS positive cells was assessed by flow cytometry (FIG. 14A) and DNA damage assessed by comet assay (FIG. 14B). FIG. 14C shows representative micrograph of β-catenin (1890× magnification, 10 µm scale) in untreated and treated cells by confocal microscopy. DAPI (blue), β-catenin; merged image shows nuclear localization of β-catenin, reflecting its active form. FIG. 14D shows β-catenin confocal images were quantified and scored based on the presence of no, low, medium, or high expression of nuclear β-catenin. Cells were pooled for analysis. There is a statistically significant increase in high nuclear β-catenin expression following treatment with rhS100A9 ($p=2.4\times10^{-3}$). Error bars: SE, $p<0.01$ and *$p<0.001$. Data are representative of three independent experiments.

FIGS. 15A to 15J show U2AF1 mutations manifest in MDS provoke pyroptosis. The ability of U2AF1 mutations to induce pyroptosis was assessed in S34F mutant cell lines. FIG. 15A shows representative density plot of inflammasome formation based on the detection of fluorescence pulse differences in ASC. FIG. 15B shows quantitation of ASC in WT, S34F, and S34F cells treated with DPI for 24 hours. FIG. 15C shows representative scatter plots of pyroptotic cells by flow cytometry. FIG. 15D shows quantitation of the percentage of pyroptotic cells in mutant and WT cells. FIGS. 15E to 14H show the relative percentage of total a-caspase-1$^+$ (FIG. 15E) and annexin-V$^+$ cells (FIG. 15F), as well as the MFI of a-caspase-1 (FIG. 15G) and annexin-V (FIG. 15H) assessed by flow cytometry. FIG. 15I shows Mean cell area was quantitated from confocal images of WT and S34F mutant cells. FIG. 15J shows that to investigate pore formation, 12.5 µg/mL EB was added to the WT and mutant line, and incorporation of the dye was measured by flow cytometry at 5 min intervals. Error bars: SE, *$p<0.05$, $p<0.01$, and *$p<0.001$. Data are representative of three independent experiments.

FIG. 16A shows quantitation of the percentage of pyroptotic versus apoptotic cells. FIG. 16B shows mean percentage of total a-caspase-1$^+$, a-caspase-3/7$^+$, and annexin-V$^+$ cells. FIG. 16C shows MFI values for a-caspase-1, a-caspase-3/7, and annexin-V$^+$ the mutant and WT cells. FIG. 16D shows representative micrograph (2520× magnification, 7.5 µm scale) depicting inflammasome formation in the WT and K700E mutant cells. DAPI, a-caspase-1, NLRP3; merged image shows inflammasome formation. FIG. 16E shows quantitative analysis of a-caspase-1/NLRP3 confocal images. FIG. 16F shows representative density plot of inflammasome formation based on the detection of fluorescence pulse differences in ASC. FIG. 16G shows quantitation of ASC in WT (n=6), K700E (n=6), and K700E cells treated with NAC (n=6) or DPI (n=3) for 24 hours.

FIG. 17A shows mean percentage of ROS-positive cells, and FIG. 17B shows ROS MFI assessed by flow cytometry. FIG. 17C shows representative micrograph (2520× magnification, 7.5 μm scale) of β-catenin expression. DAPI, β-catenin, and the merged images show nuclear localization of β-catenin. FIG. 17D shows quantitation and scoring of β-catenin confocal images based on the presence of no, low, medium, or high nuclear β-catenin in WT (n=6), K700E (n=6), and K700E cells treated with NAC (n=3) or DPI (n=3) for 24 hours. Error bars: SE, *p<0.05 and **p<0.01.

FIG. 18A shows representative density plot of inflammasome formation based on the detection of fluorescence pulse differences in ASC. FIG. 18B shows quantitation of ASC positive cells. FIGS. 18C to 18G show fold change of the mean percentage of pyroptotic cells (FIG. 18C), total a-caspase-1$^+$ cells (FIG. 18D), total annexin-V$^+$ cells (FIG. 18E), and MFI values for a-caspase-1 (FIG. 18F) and annexin-V (FIG. 18G), normalized to WT transfected cells. FIG. 18H shows mean percentage of ROS positive cells and FIG. 18I shows ROS MFI. FIG. 18J shows representative micrograph (1890× magnification, 10 μm scale) of β-catenin expression. DAPI, β-catenin, and the merged images show nuclear localization of β-catenin. FIG. 18K shows quantitation and scoring of β-catenin confocal images based on the presence of no, low, medium, or high nuclear β-catenin. Error bars: SE, *p<0.05.

FIG. 19A shows representative micrograph (2520× magnification, 7.5 μm scale) depicting inflammasome formation in control and KO cells that were untreated, or treated with NAC or DPI. DAPI, a-caspase-1, NLRP3; merged images show inflammasome formation. FIGS. 19B to 19D show quantitative analysis of a-caspase-1/NLRP3 confocal images. Cells were pooled for analysis. FIG. 19E shows representative density plot of inflammasome formation based on the detection of fluorescence pulse differences in ASC. FIG. 19F shows quantitation of percentage of ASC positive cells. FIG. 19G shows quantitation of mean cell area. FIG. 19H shows to assess pore formation, ethidium bromide was added to the cells and dye incorporation was measured by flow cytometry at 5 minute intervals. Error bars: SE, *p<0.05, p<0.01, and *p<0.001.

FIG. 20A shows mean percentage of ROS positive cells, and FIG. 20B shows ROS MFI assessed by flow cytometry. FIG. 20C shows representative micrograph (2520× magnification, 7.5 μm scale) of β-catenin expression. DAPI, β-catenin, and the merged images show nuclear localization of β-catenin. FIG. 20D shows quantitation and scoring of β-catenin confocal images based on the presence of no, low, medium, or high nuclear β-catenin. Cells were pooled for analysis, and measurements of significance were made on untreated deleted cells compared to NAC or DPI treated deleted cells. Error bars: SE, *p<0.05 and ***p<0.001.

FIG. 21A shows S100A8/A9 binds both CD33 and TLR4, resulting in inflammasome assembly. Ligation of S100A8/A9 to TLR4 results in NFκB-mediated transcription and subsequent production of proinflammatory cytokines such as pro-IL-1β and pro-IL-18, along with inflammasome components. FIG. 21B shows through interaction with Rac2 and p67phox, S100A8/A9 promotes activation of NOX, which results in a dual function. First, NOX proteins generate ROS, which serve to activate NLRs and inflammasome assembly. Second, NOX-derived ROS results in oxidation of NRX, leading to its dissociation from Dvl. Once dissociated, Dvl suppress the β-catenin destruction complex (GSKβ/CK1/APC/Axin), resulting in stabilization of β-catenin. This allows β-catenin to enter the nucleus and induce transcription of TCF/LEF controlled genes, including cyclin-D1 and c-Myc, which are essential to self-renewal.

FIG. 21C shows transient receptor potential melastatin 2 (TRPM2), a calcium-permeable cation channel in hematopoietic cells, is activated by NOX-derived ROS via oxidation of a single channel methionine residue, Met$^{214}$. Upon activation, TRPM2 causes an influx of calcium leading to mitochondrial depolarization and further release of ROS, which activate the inflammasome complex. FIG. 21D shows formation of the inflammasome complex occurs as a consequence of ROS activation and DAMP signaling. Once activated, inflammasomes mediate conversion of pro-caspase-1 to its mature and catalytically active form. Active caspase-1 cleaves pro-IL-1β and pro-IL-18 to their mature forms. FIG. 21E shows pyroptosis ensues with loss of membrane integrity resulting in release of pro-inflammatory cytokines and other intracellular contents into the extracellular milieu. FIG. 21F shows MDS-related gene mutations activate NF-κB and NLRP3 via NOX-generated ROS (Sallmyr A, et al. Cancer Lett. 2008 270(1): 1-9; Rassool F, et al. Cancer Res. 2007 67(18):8762-71).

FIG. 27A is a bar graph showing supernatant Epo concentration from HepG2 cells treated with 1 μM lenalidomide for 30 minutes prior to addition of S100A9 (1 μg/ml), TNFα (10 ng/ml) or IL-1β (10 ng/ml). FIG. 27B is a bar graph showing IL10 mRNA relative expression from HepG2 cells 24 h after treatment with 1 μM lenalidomide 30 minutes prior to addition of S100A9 (1 μg/ml) or TNFα (10 ng/ml). FIG. 27C is a western blot showing NF-kB protein in HepG2 cells 24 h after treatment with 1 μM lenalidomide 30 minutes before addition of S100A9 (1 μg/ml) or TNFα (10 ng/ml). *mean p≤0.05

FIG. 28A shows supernatant S100A9 concentration in frozen PBMC from lower risk MDS patients (n=7) treated with 1 µM lenalidomide for 24 h. Results are expressed relative to untreated cells. FIG. 28B shows TNFα expression in PBMC from lower risk MDS patients (n=7) 24 h after stimulation with 1 µM lenalidomide 30 minutes prior to addition of LPS (1 µg/ml). Results are expressed as a percentage relative to LPS treatment alone. *mean p≤0.05

DETAILED DESCRIPTION

Figure 1A:
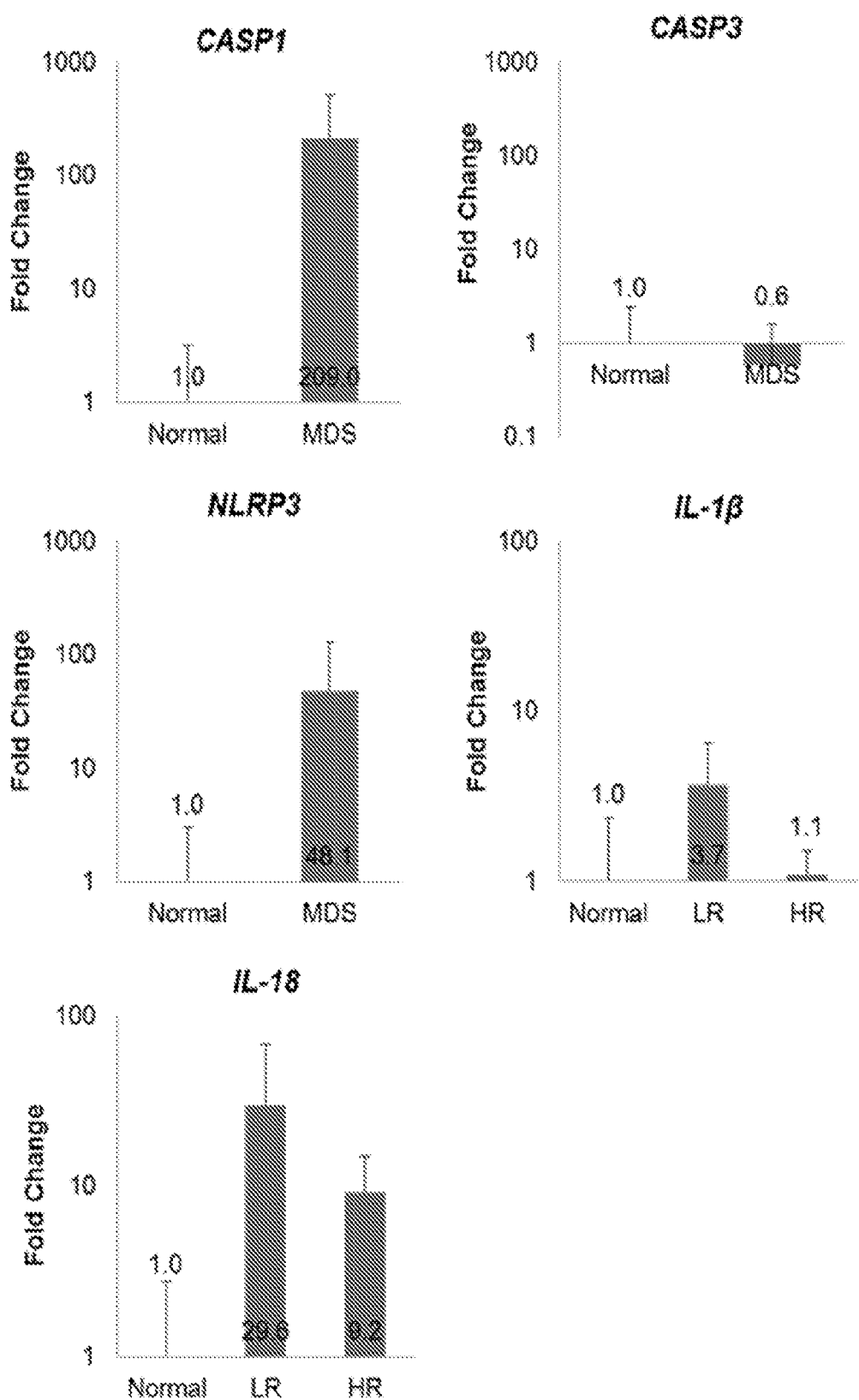
FIGS. 1A to 1H show fulminant pyroptosis is manifest in HSPC and their progeny in MDS.
Figure 1B:
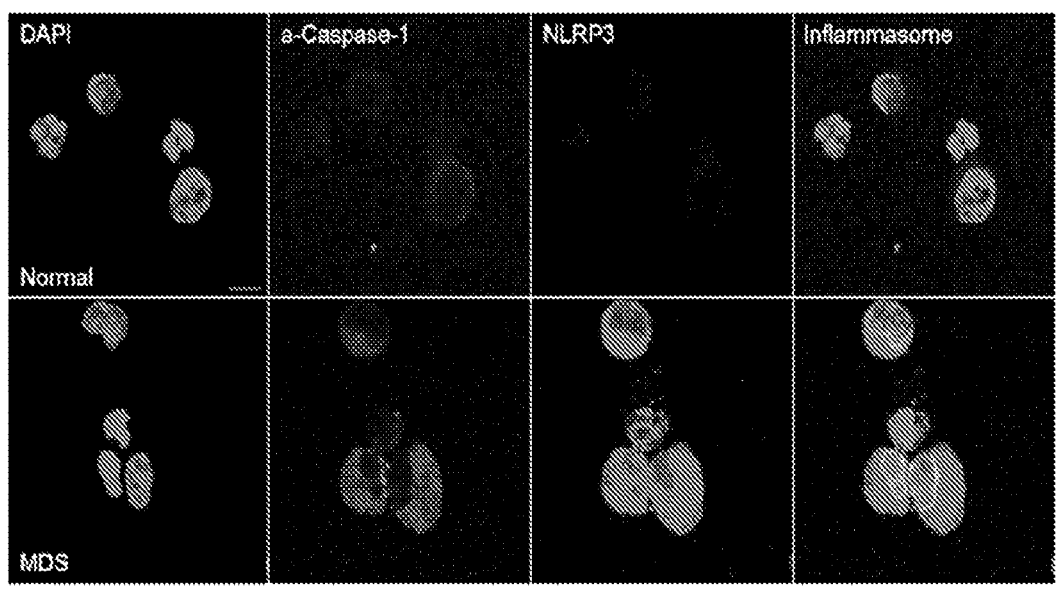
Figure 1C:
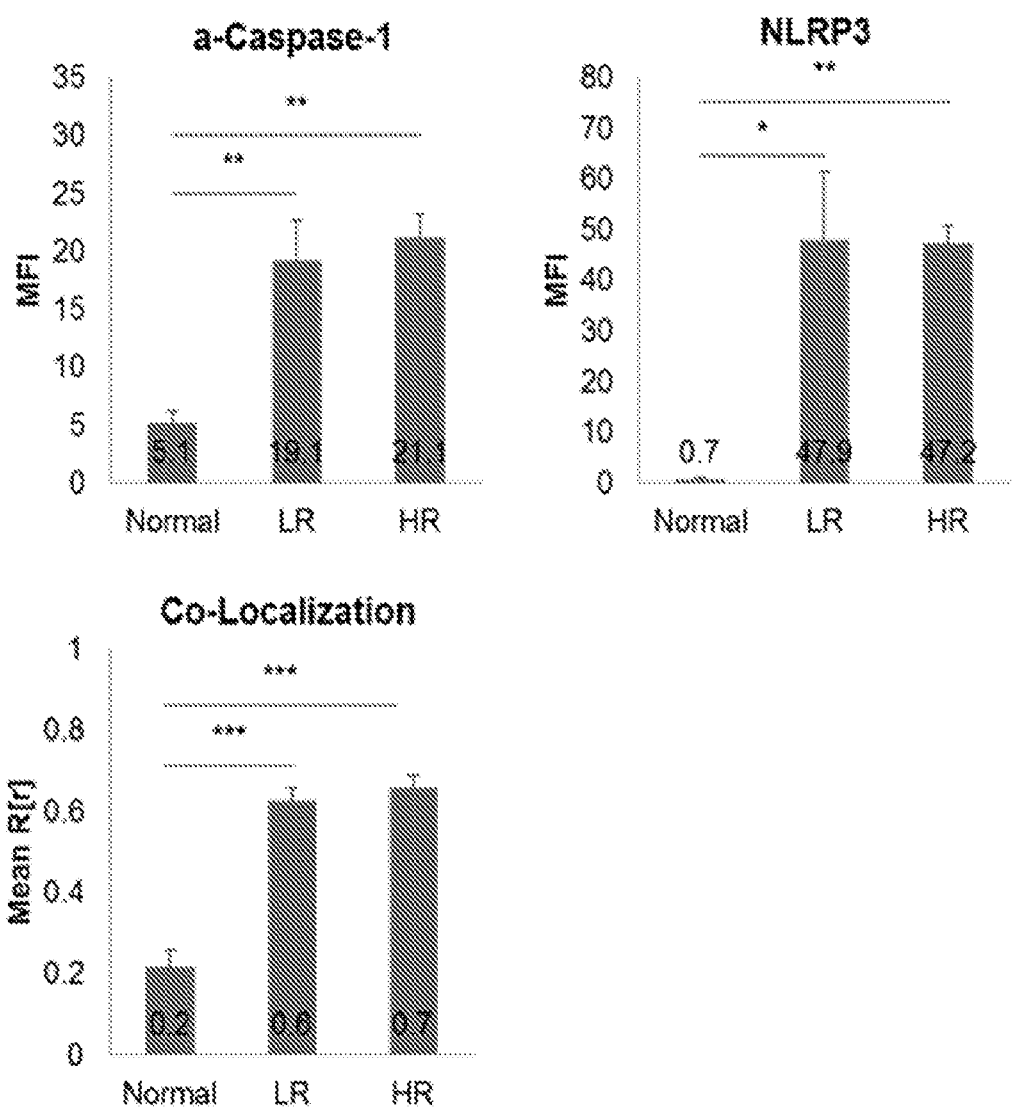
Figure 1D:
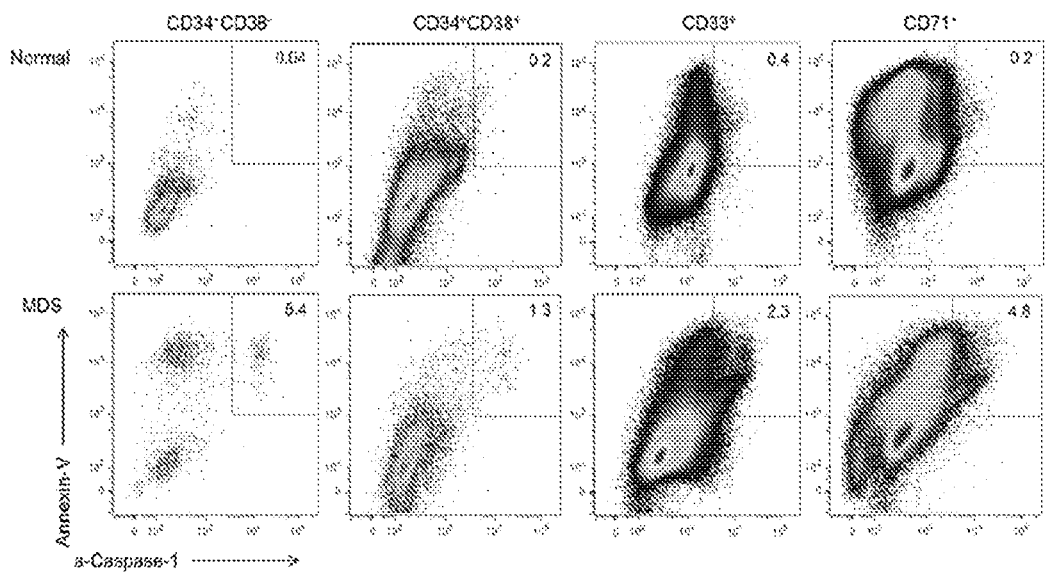
Figure 1E:
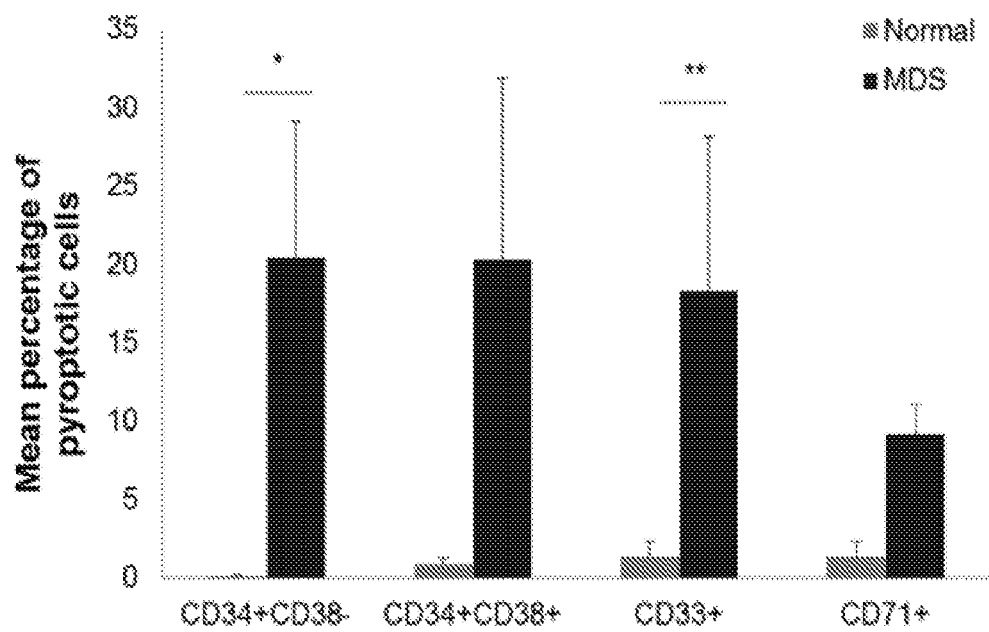
Figure 1F:
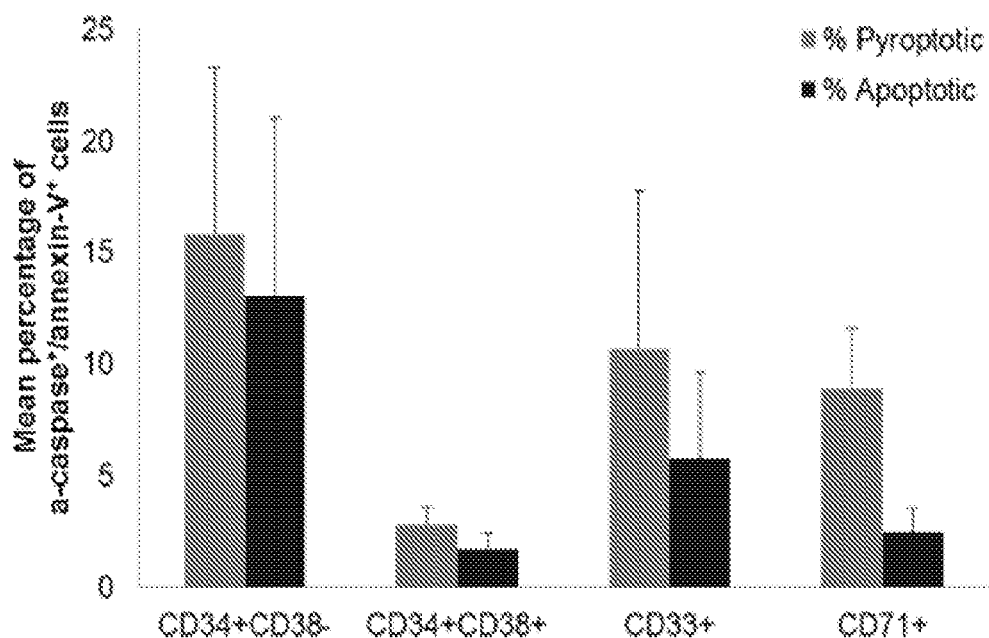
Figure 1G:
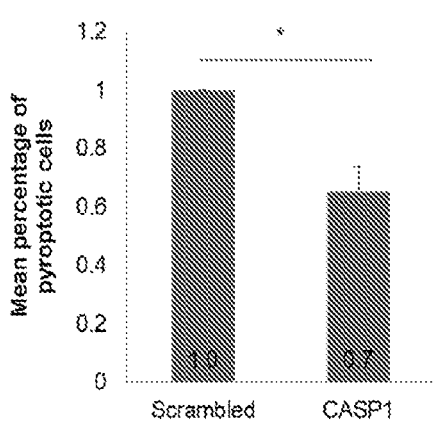
Figure 1H:
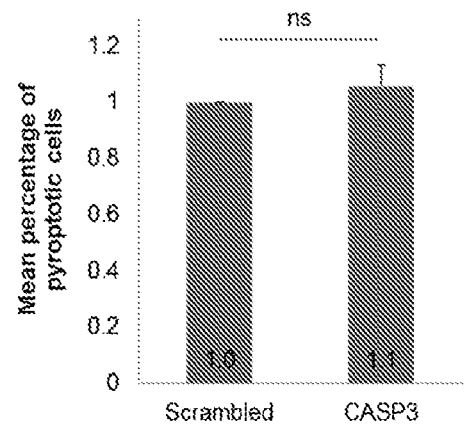

Disclosed herein are compositions and methods for diagnosing a subject with MDS and/or predicting the responsiveness of a subject to treatment of MDS with lenalidomide, erythropoietin, or a combination thereof, that involve assaying a sample from the subject for S100A9 levels, wherein elevated S100A9 levels are diagnostic of MDS in the subject and/or are an indication that the subject will be responsive to treatment with lenalidomide, erythropoietin, or a combination thereof.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The "biological sample" may comprise any clinically relevant sample containing blood cells, such as peripheral blood. The sample may be taken from a human, or, in a veterinary context, from non-human animals such as ruminants, horses, swine or sheep, or from domestic companion animals such as felines and canines.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Disclosed are methods that involve assaying a sample for S100A9 levels. In some aspects, the disclosed method is an immunoassay. Immunoassays, in their most simple and direct sense, are binding assays involving binding between antibodies and antigen. For example, antibodies that specifically bind s100A9 are commercially available and can be produced using routine skill.

Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label. See, for example, U.S. Pat. Nos. 3,817,837; 3,850,752; 3,939,350; 3,996,345; 4,277,437; 4,275,149 and 4,366,241, each of which is incorporated herein by reference in its entirety and specifically for teachings regarding immunodetection methods and labels.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

A modifier unit such as a radionuclide can be incorporated into or attached directly to any of the compounds described herein by halogenation. In another aspect, the radionuclide can be attached to a linking group or bound by a chelating group, which is then attached to the compound directly or by means of a linker. Radiolabeling techniques such as these are routinely used in the radiopharmaceutical industry.

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

Immunoassays that involve the detection of as substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

In some aspects, the method comprises detecting gene expression for genes such as s100A9, e.g., using a primer or probe that selectively binds s100A9 mRNA.

A number of widely used procedures exist for detecting and determining the abundance of a particular mRNA in a total or poly(A) RNA sample. For example, specific mRNAs can be detected using Northern blot analysis, nuclease protection assays (NPA), in situ hybridization, or reverse transcription-polymerase chain reaction (RT-PCR).

In theory, each of these techniques can be used to detect specific RNAs and to precisely determine their expression level. In general, Northern analysis is the only method that provides information about transcript size, whereas NPAs are the easiest way to simultaneously examine multiple messages. In situ hybridization is used to localize expression of a particular gene within a tissue or cell type, and RT-PCR is the most sensitive method for detecting and quantitating gene expression.

Northern analysis presents several advantages over the other techniques. The most compelling of these is that it is the easiest method for determining transcript size, and for identifying alternatively spliced transcripts and multigene family members. It can also be used to directly compare the relative abundance of a given message between all the samples on a blot. The Northern blotting procedure is straightforward and provides opportunities to evaluate progress at various points (e.g., intactness of the RNA sample and how efficiently it has transferred to the membrane). RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes.

The Nuclease Protection Assay (NPA) (including both ribonuclease protection assays and S1 nuclease assays) is an extremely sensitive method for the detection and quantitation of specific mRNAs. The basis of the NPA is solution hybridization of an antisense probe (radiolabeled or nonisotopic) to an RNA sample. After hybridization, single-stranded, unhybridized probe and RNA are degraded by nucleases. The remaining protected fragments are separated on an acrylamide gel. Solution hybridization is typically more efficient than membrane-based hybridization, and it can accommodate up to 100 µg of sample RNA, compared with the 20-30 µg maximum of blot hybridizations. NPAs are also less sensitive to RNA sample degradation than Northern analysis since cleavage is only detected in the region of overlap with the probe (probes are usually about 100-400 bases in length).

NPAs are the method of choice for the simultaneous detection of several RNA species. During solution hybridization and subsequent analysis, individual probe/target interactions are completely independent of one another. Thus, several RNA targets and appropriate controls can be assayed simultaneously (up to twelve have been used in the same reaction), provided that the individual probes are of different lengths. NPAs are also commonly used to precisely map mRNA termini and intron/exon junctions.

In situ hybridization (ISH) is a powerful and versatile tool for the localization of specific mRNAs in cells or tissues. Unlike Northern analysis and nuclease protection assays, ISH does not require the isolation or electrophoretic separation of RNA. Hybridization of the probe takes place within the cell or tissue. Since cellular structure is maintained throughout the procedure, ISH provides information about the location of mRNA within the tissue sample.

The procedure begins by fixing samples in neutral-buffered formalin, and embedding the tissue in paraffin. The samples are then sliced into thin sections and mounted onto microscope slides. (Alternatively, tissue can be sectioned frozen and post-fixed in paraformaldehyde.) After a series of washes to dewax and rehydrate the sections, a Proteinase K digestion is performed to increase probe accessibility, and a labeled probe is then hybridized to the sample sections. Radiolabeled probes are visualized with liquid film dried onto the slides, while nonisotopically labeled probes are conveniently detected with colorimetric or fluorescent reagents.

RT-PCR has revolutionized the study of gene expression. It is now theoretically possible to detect the RNA transcript of any gene, regardless of the scarcity of the starting material or relative abundance of the specific mRNA. In RT-PCR, an RNA template is copied into a complementary DNA (cDNA) using a retroviral reverse transcriptase. The cDNA is then amplified exponentially by PCR. As with NPAs, RT-PCR is somewhat tolerant of degraded RNA. As long as the RNA is intact within the region spanned by the primers, the target will be amplified.

Relative quantitative RT-PCR involves amplifying an internal control simultaneously with the gene of interest. The internal control is used to normalize the samples. Once normalized, direct comparisons of relative abundance of a specific mRNA can be made across the samples. It is crucial to choose an internal control with a constant level of expression across all experimental samples (i.e., not affected by experimental treatment). Commonly used internal controls (e.g., GAPDH, β-actin, cyclophilin) often vary in expression and, therefore, may not be appropriate internal controls. Additionally, most common internal controls are expressed at much higher levels than the mRNA being studied. For relative RT-PCR results to be meaningful, all products of the PCR reaction must be analyzed in the linear range of amplification. This becomes difficult for transcripts of widely different levels of abundance.

Competitive RT-PCR is used for absolute quantitation. This technique involves designing, synthesizing, and accurately quantitating a competitor RNA that can be distinguished from the endogenous target by a small difference in size or sequence. Known amounts of the competitor RNA are added to experimental samples and RT-PCR is performed. Signals from the endogenous target are compared with signals from the competitor to determine the amount of target present in the sample.

The disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The compositions disclosed herein may be administered prophylactically to patients or subjects who are at risk for MDS. Thus, the method can further comprise identifying a subject at risk for MDS prior to administration of the herein disclosed compositions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical daily dosage of the disclosed composition used alone might range from about 1 µg/kg to up to 100 mg/kg of body weight or more per day, depending on the factors mentioned above.

In some embodiments, lenalidomide, erythropoietin, or a combination thereof is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of lenalidomide, erythropoietin, or a combination thereof administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

A number of embodiments of the invention have been described. Nevertheless, it will be understood that various modifications may be made without departing from the spirit

EXAMPLES

Example 1: Identification of the NLRP3 Inflammasome as a Driver of the MDS Phenotype Methods MDS Patient Specimens.

MDS patients consented on The University of South Florida Institutional Review Board approved protocols were recruited from the Malignant Hematology Clinic at H. Lee Moffitt Cancer Center & Research Institute, and the Eastern Cooperative Oncology Group (ECOG) E2905 trial (NCT00843882). Pathologic subtype of MDS was reported according to World Health Organization (WHO) criteria and prognostic risk assigned according to the International Prognostic Scoring System (IPSS). Patients were segregated as lower (Low, Intermediate-1) and higher risk (Intermediate-2, High) MDS. Bone marrow mononuclear cells (BM-MNC) were isolated from heparinized bone marrow aspirates using Ficoll-Hypaque Plus gradient centrifugation (GE Healthcare).

Mice.

S100A9Tg mice were used for animal studies (Chen X, et al. J Clin Invest. 2013 123(11):4595-611). WT FVB/NJ mice were purchased from Jackson Laboratories (Bar Harbor, Me.). Heparinized BM cells were isolated from tibias and femurs of male and female mice.

Reagents and Cells.

U937 cells were grown in RPMI1640 supplemented with 10% FBS. TF-1 U2AF1 mutant and mock WT cells were cultured in RPMI1640 supplemented with 10%/FBS and 2 ng/mL recombinant human GM-CSF. Cells were maintained at 37° C. under 5% $CO_2$. Normal, heparinized BM aspirates were purchased from Lonza Walkersville or AllCells, LLC. Recombinant human S100A9 and the CD33/Siglec 3 chimeric fusion protein were generated as previously described (Chen X, et al. J Clin Invest. 2013 123(11):4595-611). The IRAK4 inhibitor was acquired through material transfer agreement from Nimbus Discovery. NAC and DPI were purchased from Sigma-Aldrich. Active caspase-1 and caspase-3/7 were detected using FAM-FLICA® Caspase-1 and Caspase-3/7 activity kits, (ImmunoChemistry Technologies). NLRP1 antibodies were purchased from Santa Cruz Biotechnology, NLRP3 antibodies from Abcam, and β-catenin antibodies from BD Biosciences.

Pyroptosis Flow Cytometry Panel.

For human samples, treated and untreated BM-MNC were incubated overnight in IMDM, supplemented with 10% autologous BM plasma. Subsequently, cells were harvested, washed twice in 1×PBS, and stained with LIVE/DEAD Violet fluorescent reactive dye according to the manufacturer's protocol (Life Technologies). Cells were resuspended in 1×PBS with 2% BSA, and incubated at room temperature for 15 minutes to block non-specific binding. After washing, cells were stained with 30×FAM-FLICA® Caspase-1 and Caspase-3/7 solution at a ratio of 1:30 for 2 hours at 37° C. Cells were washed and stained for cell surface receptors using CD38:PE-CF594, CD33:BV711, CD34:APC (BD Biosciences), and CD71:PE-Cyanine7 (eBioscience). All antibodies were diluted 1:20, and cells were stained for 30 minutes at 4° C. Cells were washed, resuspended in 1× binding buffer, and stained with Annexin-V:Cy5.5 at a dilution of 1:20 for 15 minutes at room temperature (BD Biosciences). 1× binding buffer was added to a final volume of 400 µL. Sample acquisitions were carried out using a BD LSR II flow cytometer and FACSDiva software (BD Biosciences). Calibration of the flow cytometer was carried out prior to each experiment using Rainbow Mid-Range Fluorescent Particles (BD Biosciences). To establish fluorescence compensation settings, ArC Amine Reactive Compensation Beads were used for LIVE/DEAD Violet staining (Life Technologies), and BD CompBead Plus Anti-Mouse Ig κ/Negative Control (BSA) Compensation Plus Particles were used for surface receptor conjugates (BD Biosciences). Data were analyzed using FlowJo 9.7.5 software (FlowJo, LLC, Ashland, Oreg.).

S100A9 Flow Cytometry Experiments in U937 Cells.

Monocytic U937 cells were treated with the indicated concentrations of rhS100A9 for 24 hours, or with 5 µg/mL rhS100A9 for the indicated time points. Subsequently, cells were stained with 30×FAM-FLICA® Caspase-1 solution at a ratio of 1:30 for 2 hours at 37° C. Cells were washed, resuspended in 1× binding buffer, and stained with Annexin-V:PE at a dilution of 1:30 for 15 minutes at room temperature. 1× binding buffer was added to a final volume of 350 µL. Sample acquisitions were carried out using a BD FACSCalibur flow cytometer (BD Biosciences). Data were analyzed using FlowJo 9.7.5 software.

Intracellular S100A9 Flow Cytometry.

BM-MNC were incubated overnight in IMDM, supplemented with 10% autologous BM plasma. The following day, cells were harvested and washed twice in 1×PBS. Cells were fixed with BD Cytofix Fixation Buffer at 37° C. for 10 minutes, and stored at −80° C. until staining. At the time of staining, cells were warmed to 37° C. in a water bath, spun down, and washed 1× with staining buffer. Pellets were resuspended in 1 mL of pre-warmed BD Permeabilization Buffer III, and incubated on ice for 30 minutes. Cells were washed twice with staining buffer. Following washing, cells were stained with S100A9:FITC (BioLegend), and cell surface receptors using CD38:PE-CF594, CD33:BV711, CD34:APC (BD Biosciences), and CD71:PE-Cyanine7 (eBioscience). All antibodies were diluted 1:20, and cells were stained for 30 minutes at 4° C. Cells were washed and resuspended in 400 µL staining buffer. Sample acquisitions were carried out using a BD LSR II flow cytometer and FACSDiva software (BD Biosciences).

Enzyme-Linked Immunosorbent Assays (ELISA).

Human S100A9 DuoSet ELISA kit was purchased from R&D Systems and HMGB1 ELISA kit was purchased from MYBioSource. Both were performed according to manufacturer's protocol.

Immunofluorescence Confocal Microscopy.

MDS and normal donor BM-MNC and mouse BM cells were stained with 30×FAM-FLICA® Caspase-1 solution at a ratio of 1:30 for 2 hours at 37° C. Cells were washed and cytospins were generated using a 5 minutes centrifugation at 450 rpm. Slides were fixed at 37° C. for 10 minutes using BD Cytofix Fixation Buffer (BD Biosciences), and subsequently washed using PBS. Cells were permeabilized with 0.1% Triton X-100/2% BSA in PBS for 15 minutes at room temperature. After washing with PBS, cells were blocked using 2% BSA in PBS for 30 minutes at room temperature, and washed again. Cells were incubated with the appropriate primary antibody overnight (1:400 for NLRP3, 1:20 for β-catenin) at 4° C. The next day, cells were washed with PBS and incubated with the appropriate secondary antibodies (1:500) for 1 hour at room temperature. After washing, cells were covered with ProLong Gold Antifade Reagent with DAPI prior to the addition of a coverslip (Life Technologies). Co-localization of a-caspase-1 with NLRP3 inflammasome complexes was assessed using a Leica TCS SP5 AOBS Laser Scanning Confocal microscope (Leica Microsystems). Analysis of the inflammasome images was performed with Definiens Developer 2.0 (Definiens AG). The software was used to segment cells based on brightness and size thresholds, followed by a watershed segmentation algorithm. Intensity values and Pearson's correlation coefficient were extracted from the segmented cells. For β-catenin image analysis, confocal images were imported into Definiens Tissue Studio v3.0, 64 Dual in .tif format. Cells were separated from background using the RGB thresholds. Nuclei were identified by setting thresholds in the DAPI channel. Typical cells averaged 60 microns. The red intensity (β-catenin) in the nucleus and cytoplasm was established by setting thresholds to low, medium and high in the red channel on a scale of 0-255 in the red channel.

ASC Staining to Detect Inflammasome Formation by Flow Cytometry.

Staining was carried out as described (Sester D. P, et al. J Immunol. 2015 194(1):455-62). Briefly, cell pellets were resuspended in 1 mL of prewarmed BD Permeabilization Buffer III, and incubated on ice for 30 minutes. Cells were washed 2× with staining buffer. Following washing, cells were stained with rabbit-anti-ASC primary antibodies at a 1:1500 dilution and incubated for 90 minutes. Cells were washed, stained with secondary antibodies at a dilution of 1:1500, and incubated for 45 minutes. Cells were washed, and sample acquisitions were carried out using a BD LSR II flow cytometer and FACSDiva software.

Real-Time Quantitative PCR.

RNA was isolated from BM-MNC using the RNeasy Mini Kit (Qiagen). cDNA was produced using the iScript cDNA Synthesis Kit (Bio-Rad). Sequences for primers can be found in Table 1. GAPDH mRNA was used for transcript normalization. cDNA was amplified using the iQ SYBR Green Supermix and the CFX96 Real-Time PCR Detection System (Bio-Rad). PCR conditions were as follows: 10 minutes at 95° C., followed by 40 cycles of amplification (15 seconds at 95° C. and 1 minute at 60° C.). Relative gene expression was calculated using the $-2^{\Delta\Delta Ct}$ method.

TABLE 1

Primer sets used for qPCR.

| Gene | Forward | |
|---|---|---|
| CASP1 | 5'-TGAGCAGCCAGATGGTAGAGC-3' | SEQ ID NO: 1 |
| CASP3 | 5'-GTGAGGCGGTTGTAGAAGAGTTTC-3' | SEQ ID NO: 2 |
| IL-1β | 5'-CTCTTCGAGGCACAAGGCAC-3' | SEQ ID NO: 3 |
| IL-18 | 5'-ACTGCCTGGACAGTCAGCAA-3' | SEQ ID NO: 4 |
| NLRP1 | 5'-TCTACGTTGGCCACTTGGGA-3' | SEQ ID NO: 5 |
| NLRP3 | 5'-CAATGGGGAGGAGAAGGCGT-3' | SEQ ID NO: 6 |
| S100A9 | 5'-CTCGGCTTTGACAGAGTGCAA-3' | SEQ ID NO: 7 |
| HMGB1 | 5'-CCCTCCCAAAGGGGAGACAAA-3' | SEQ ID NO: 8 |
| GAPDH | 5'-GAAGGTGAAGGTCGGACT-3' | SEQ ID NO: 9 |
| | Reverse | |
| CASP1 | 5'-TCACTTCCTGCCCACAGACAT-3' | SEQ ID NO: 10 |
| CASP3 | 5'-TGAGCAGGGCTCGCTAACTC-3' | SEQ ID NO: 11 |

TABLE 1-continued

Primer sets used for qPCR.

| Gene | | |
|---|---|---|
| IL-1β | 5'-CAAGTCATCCTCATTGCCACTGT-3' | SEQ ID NO: 12 |
| IL-18 | 5'-GCAGCCATCTTTATTCCTGAGA-3' | SEQ ID NO: 13 |
| NLRP1 | 5'-AGAGGTGAAGGTACGGCTATGC-3' | SEQ ID NO: 14 |
| NLRP3 | 5'-TCTGAACCCCACTTCGGCTC-3' | SEQ ID NO: 15 |
| S100A9 | 5'-CTGGTTCAGGGTGTCTGGGT-3' | SEQ ID NO: 16 |
| HMGB1 | 5'-AGAGGAAGAAGGCCGAAGGAG-3' | SEQ ID NO: 17 |
| GAPDH | 5'-GAAGATGGTGATGGGATTTC-3' | SEQ ID NO: 18 |

Lentiviral Infection of Primary Mononuclear Cells.

Lentiviral constructs were purchased from Origene. Caspase-1 (TL305640), Caspase-3 (TL305638b), and scrambled (TR30021) HuSH™ shRNA plasmids were amplified by transforming One Shot® Top 10 competent cells (Life technologies) according to manufacturer's protocol. Single colonies were expanded and mini preps were performed using the Qiagen QIAprep® Mini Prep Kit. HEK293T cells were transfected by incubating 2600 ng of shRNA plasmid, 30 μL Lipofectamine® 2000 (Invitrogen), 26 μL MISSION™ Lentiviral Packaging Mix (Sigma Aldrich) in 500 μL of Opti-MEM®I (Life technologies) for 15 minutes at room temperature. This mixture was then added to 70% confluent HEK293T cells with 4 mL Opti-MEM®I medium without serum in a 100 mm dish. Cells were incubated at 37° C. for 6 hours in a humidified chamber, then 6 mL of DMEM (Mediatech, Manassas, Va.) with 10% serum was added. In the morning, medium was changed and 10 mL fresh DMEM was added. Virus was collected at 48 and 72 hours using 0.45 μm filters. The concentration was determined to be at least $5\times10^5$ IFU/mL using Clontech Lenti-X Go Stix (Mountain View, Calif.) and stored at 4° C. Virus up to one week old was used for experiments. For primary cell infection, 2.5 million cells were plated in a 100 mm dish with 1.25 mL fresh virus, 1.25 mL opti-MEM®I, and 8 μg/mL polybrene. Cells were incubated overnight, then 5 mL of fresh IMDM (Mediatech) with 10% FBS was added. RNA was isolated after 72 hours of infection using Qiagen RNeasy Isolation Kit according to manufacturer's protocol and mRNA levels were analyzed by qPCR using GAPDH mRNA levels as a control. Additionally at 72 hours, 10% v/v of autologous BM plasma was added to the remaining cells. Twenty-four hours after plasma was added, cells were stained with annexin-V, 7-AAD, and FAM-FLICA® Caspase-1 and analyzed using a BD FAC-SCalibur flow cytometer.

Colony Formation Assay.

Four replicates of 350,000 BM-MNC/mL were resuspended in 10% autologous BM plasma and plated in Metho-Cult methylcellulose medium (Stemcell Technologies) supplemented with 1% v/v penicillin-streptomycin and 3 units/mL erythropoietin. CD33-IgG and MCC950 were added directly to the medium prior to plating. Colonies of BFU-E, CFU-GM, and CFU-GEMM were scored using an inverted light microscope fourteen days after plating.

SRSF2 Transfection of HEK293T Cells.

HEK293T cells were transfected by incubating 4 μg of SRSF2 DNA with 10 μL Lipofectamine® 2000 in 100 μL of Opti-MEM®I for 20 minutes at room temperature. This mixture was added to 70% confluent HEK293T cells with 2 mL Opti-MEM®I medium without serum in a 6 well plate. Cells were incubated at 37° C. for 4 hours in a humidified chamber, then medium was replaced with 2 mL of DMEM with 10% serum added. Treatment with NAC or DPI and subsequent analyses were carried out 24 and 48 hours following transfection, respectively.

Pore Formation Assay.

MDS and normal donor BM-MNC were incubated in 10% autologous BM plasma at 37° C. overnight. Cells were subsequently washed and resuspended in 1 mL of PBS. 12.5 µg/mL ethidium bromide (Fisher Scientific, Pittsburgh, Pa.) was added, and sample acquisitions were acquired at the indicated time points using a BD FACSCalibur flow cytometer.

Ros Detection.

ROS were detected using CM-H2DCFDA and Cell ROX® Deep Red Reagent according to manufacturer's protocol (Life Technologies).

Comet Assays.

Monocytic U937 cells were treated with 5 µg/mL rhS100A9 for 24 hr. DNA damage was measured by single cell gel electrophoresis using alkaline CometAssay® according to manufacturer's protocol (Trevigen Inc.).

ICTA Mouse Treatment Studies.

ICTA was synthesized by the Drug Discovery Core Facility at H. Lee Moffitt Cancer Center & Research Institute. Six month old transgenic mice (n=5) were dosed every other day with 50 mg/kg ICTA by oral gavage, for a total of eight weeks.

Statistics.

Data are expressed as means±standard error. Statistical analyses were carried out in Microsoft Excel using student's t-test, correlations using chi square for non-continuous variables and logistic regression for continuous variables were performed using IPSS software v22 (SPSS Inc., Chicago, Ill.), and *p values<0.05, p<0.01, and *p<0.01 were considered to be statistically significant.

Results

MDS HSPC Manifest Inflammasome Activation and Pyroptosis

To assess whether pyroptosis was primed in MDS, expression of genes encoding inflammasome proteins was evaluated in bone marrow (BM) mononuclear cells (BM-MNC) isolated from MDS patients (n=10) compared to age-matched normal controls (n=5). MDS specimens displayed marked up-regulation of inflammasomal transcripts (FIG. 1$a$). For example, caspase-1 (CASP1) gene expression was increased 209-fold in MDS, whereas caspase-3 (CASP3), the canonical apoptotic caspase, was 40% lower in MDS compared to normal controls. Gene expression of NLRP3 was increased 48.1-fold in MDS. Further, the expression of the inflammatory cytokines IL-1β and IL-18 was increased 3.7-fold and 29.6-fold in lower-risk MDS (n=5) compared to normal controls (n=5), whereas higher-risk MDS specimens demonstrated only 1.1-fold and 9.2-fold up-regulation (n=5), consistent with the known up-regulation of survival signals in higher risk MDS. Confocal fluorescence microscopy confirmed selective activation of NLRP3 inflammasome complexes in MDS specimens versus age-matched control BM-MNC, where there was co-localization and increased active (a)-caspase-1 (MFI increased 3.7-fold in lower-risk [p=7.1×10$^{-3}$] and 4.1-fold in higher-risk disease [p=6.0×10$^{-3}$]) and NLRP3 (MFI was increased 69.1-fold in lower-risk [p=0.013] and 68.2-fold in higher-risk [p=5.1×10$^{-3}$]) disease (FIG. 1$b$, 1$c$). MDS specimens also displayed significantly greater inflammasome assembly compared to controls, irrespective of IPSS risk group (FIG. 1$c$). Specifically, NLRP3 inflammasome assembly was increased 2.9-fold in lower-risk (p=3.9×10$^{-5}$) and 3.1-fold in higher-risk (p=7.1×10$^{-5}$) patients.

Figure 7A:
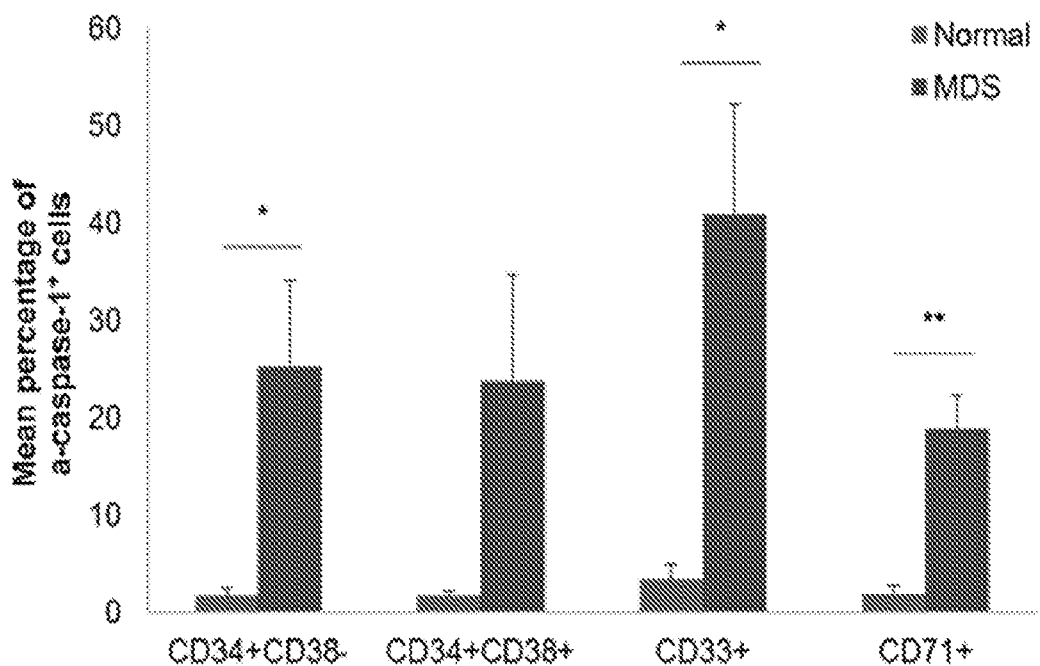
FIGS. 7A to 7C show caspase-1 activation exceeds caspase-3 activation in MDS.
Figure 7B:
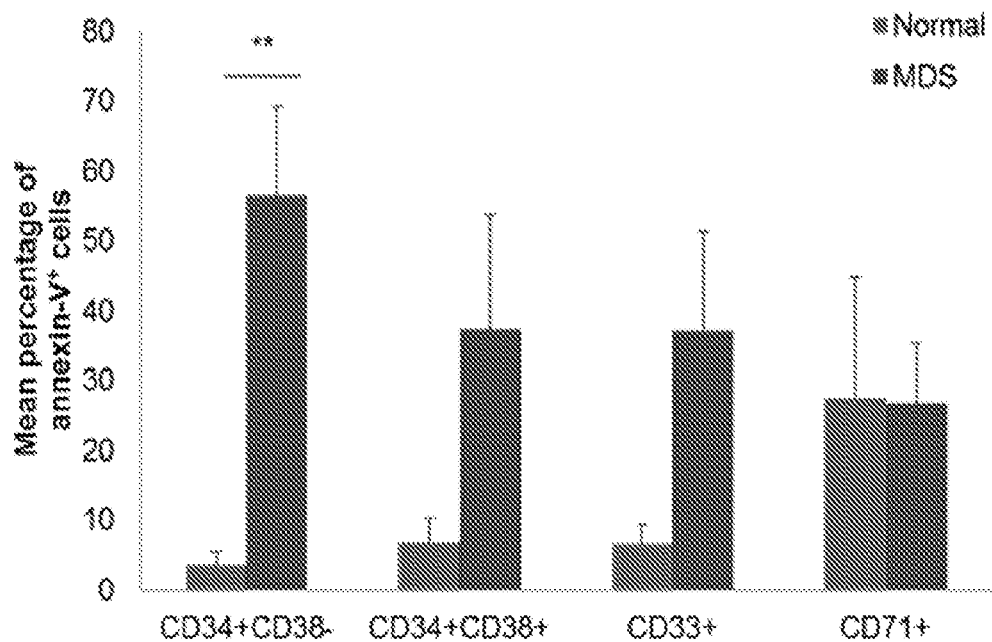
Figure 7C:
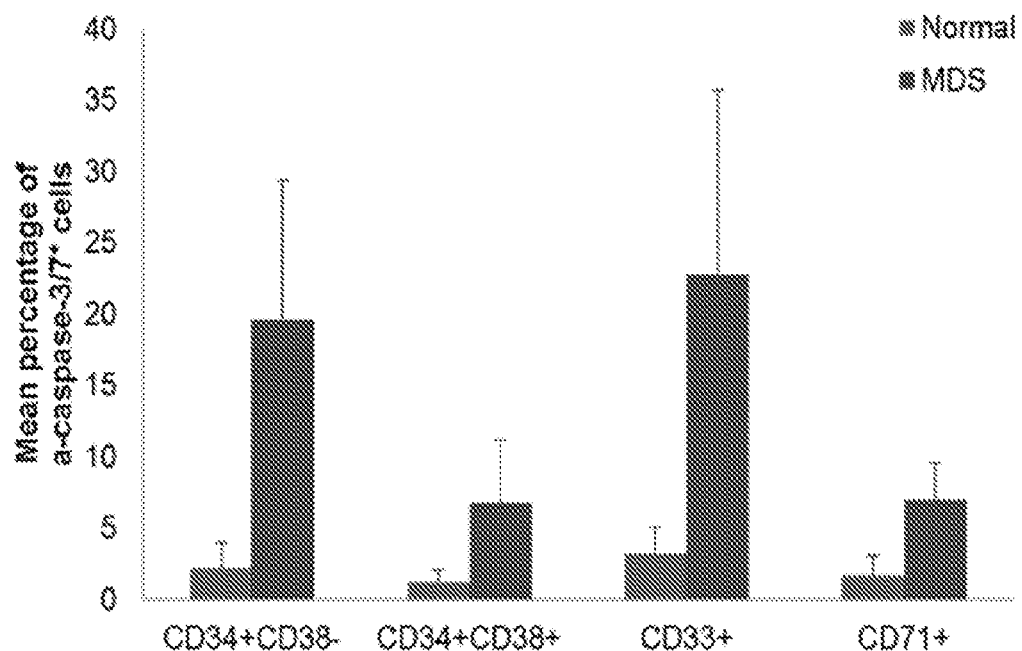
Figure 8A:
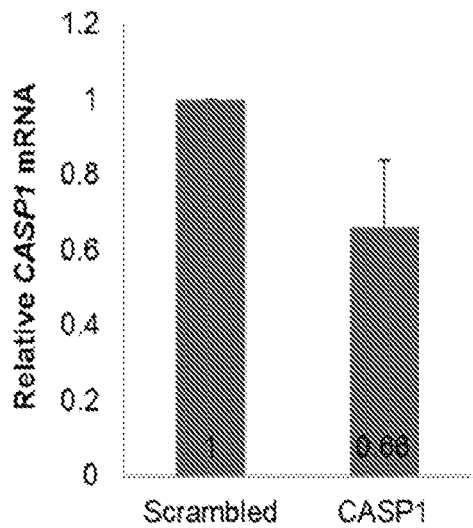
FIGS. 8A and 8B show gene expression following lentivirus-mediated transfection of MDS BM-MNC. Gene expression of CASP1 (FIG. 8A) and CASP3 (FIG. 8B) was assessed by qPCR following shRNA-directed silencing performed by lentivirus transfection of lower-risk BM-MNC (n=3).
Figure 8B:
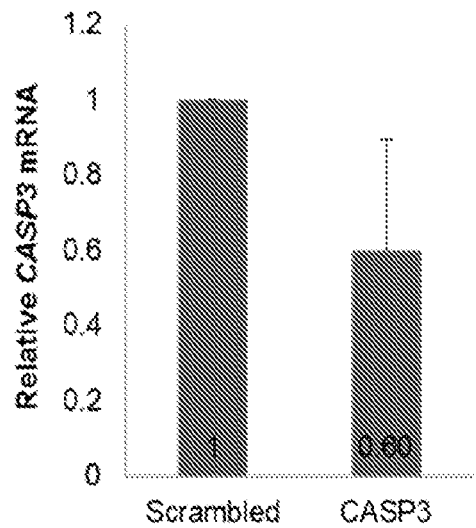
Figure 9A:
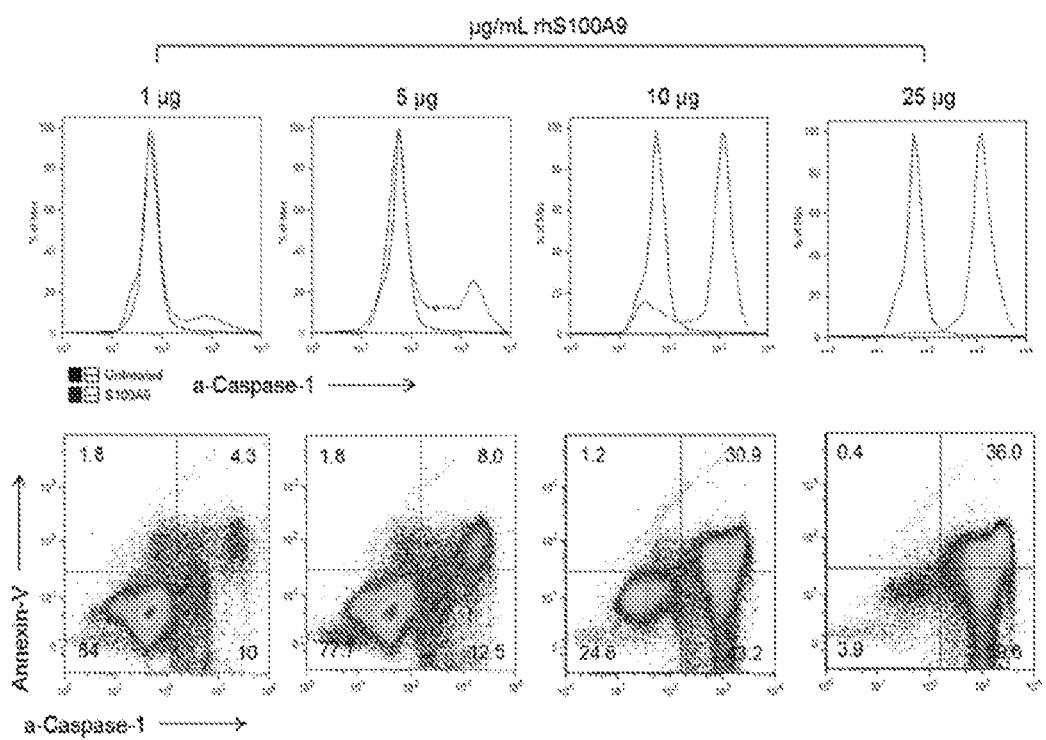
FIGS. 9A to 9F show S100A9 provokes pyroptosis and inflammasome activation ex vivo.
Figures 9B, 9C, 9D:
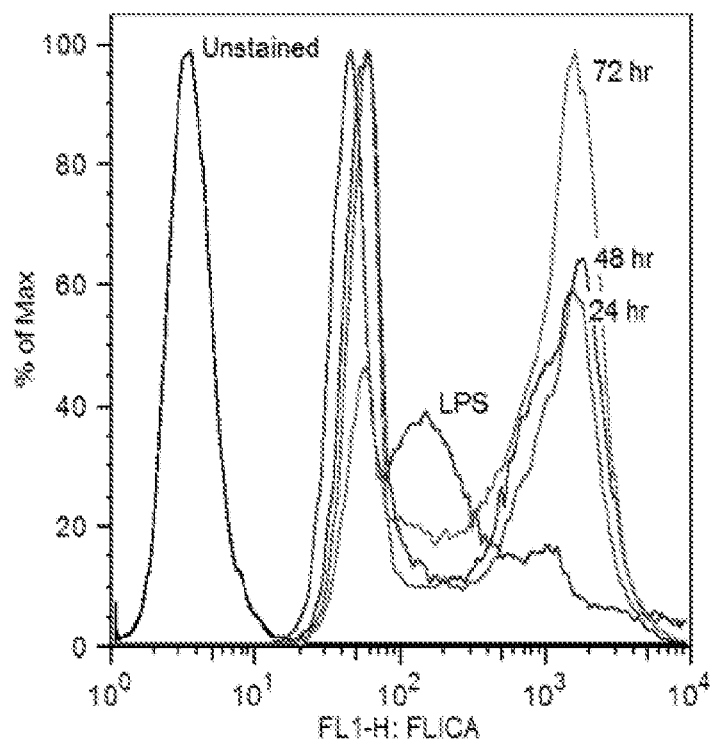
Figure 9E:
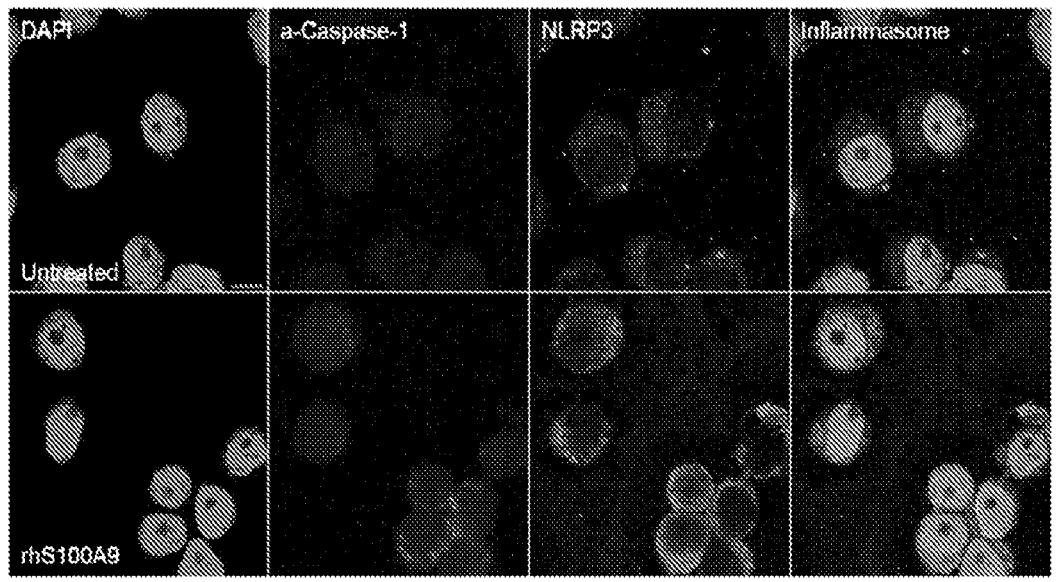
Figure 9F:
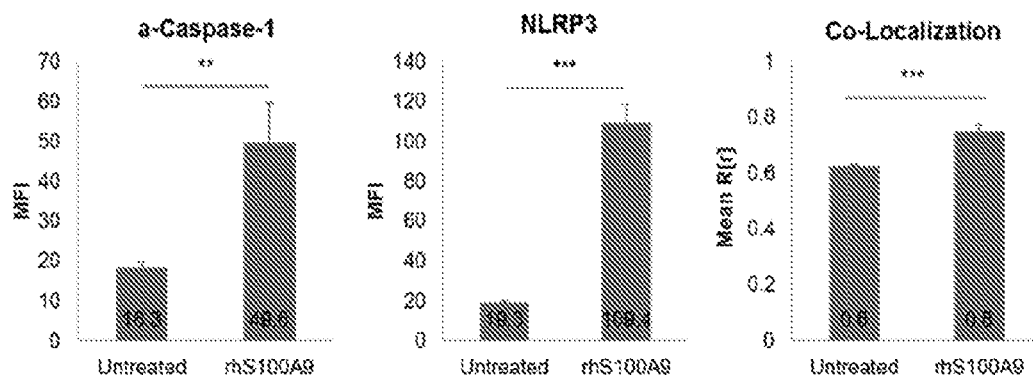

To assess pyroptosis in MDS, the percentage of pyroptotic cells, defined as percentage of a-caspase-1$^+$/annexin-V$^+$ cells, was determined in phenotypically distinct hematopoietic lineages by flow cytometry. Normal (n=5) and lower-risk MDS BM-MNC (n=8) were incubated with autologous BM plasma for 24 hours prior to flow cytometry analysis. MDS HSPC demonstrated markedly increased pyroptosis (FIG. 1$d$), where the fraction of pyroptotic cells increased 150-fold in CD34$^+$CD38$^-$ stem cells (p=0.051), 22.8-fold in progenitor cells (CD34$^+$CD38$^+$), 13.0-fold in immature myeloid cells (CD33$^+$), and 6.8-fold in erythroid cells (CD71$^+$, p=3.1×10$^{-3}$), compared to normal controls (FIG. 1$e$). Additionally, the percentage of a-caspase-1$^+$ cells was increased 15.6-fold in hematopoietic stem cells (p=0.032), 14.1-fold in progenitors, 12.1-fold in immature myeloid cells (p=0.012), and 10.1-fold in CD71$^+$ cells (p=1.5×10$^{-3}$) (FIG. 7$a$). Overall, only the stem cell population had a significant increase in total annexin-V$^+$ cells (p=3.8×10$^{-3}$) (FIG. 7$b$). A-caspase-1 MFI directly correlated with NLRP3 MFI, inflammasome assembly, and the percentage of pyroptotic stem cells. Notably, the latter was directly associated with the percentage of a-caspase-1$^+$CD33 myeloid progenitors. The extent of apoptosis (i.e., a-caspase-3/7$^+$/annexin-V$^+$) was also evaluated in lower-risk MDS specimens (n=5). Pyroptotic cells were 1.2-fold, 1.6-fold, 1.9-fold, and 3.6-fold up-regulated in stem cells, progenitor cells, immature myeloids, and erythroid cells, compared to the apoptotic cell fraction (FIG. 1$f$). No significant differences in a-caspase-3/7$^+$ cells were detected in any of the four hematopoietic lineages investigated (FIG. 7$c$). Lastly, to confirm that caspase-1 is essential for hematopoietic cell death in MDS, shRNA-directed silencing of caspase-1 and caspase-3 was performed by lentivirus transfection of lower-risk BM-MNC (n=3) (FIG. 8). Knockdown of caspase-1 significantly decreased the fraction of pyroptotic cells, greater than 35% versus scrambled transfected controls (p=0.038) (FIG. 1$g$). In contrast, knockdown of caspase-3 had no discernible effect (FIG. 1$h$), confirming selective caspase-1-dependence.

The DAMP Protein S100A9 is a Primary Initiator of Pyroptosis

BM plasma concentrations of the alarmin S100A9 are profoundly increased in MDS and stimulate the expansion of MDSC through ligation of its cognate receptors, TLR4 and CD33 (Chen X, et al. J Clin Invest. 2013 123(11):4595-611). As NLRPs are sensors of DAMP signals, experiments were conducted to determine if S100A9 triggers pyroptosis in MDS. Indeed, treatment of the monocytic cell line U937 with recombinant human S100A9 (rhS100A9) resulted in a concentration-dependent increase in the fraction of pyroptotic cells (FIG. 9$a$), with a corresponding increase in a-caspase-1 MFI and percentage of a-caspase-1$^+$ cells (FIG. 9$b$). Likewise, treatment with 5 µg/mL rhS100A9 provoked a time-dependent increase in activation of caspase-1 (FIG. 9$c$, 9$d$). Furthermore, treatment with rhS100A9 markedly increased levels of NLRP3 inflammasome complexes and this was accompanied by caspase-1 activation (FIG. 9$e$, 9$f$).

Figure 10:
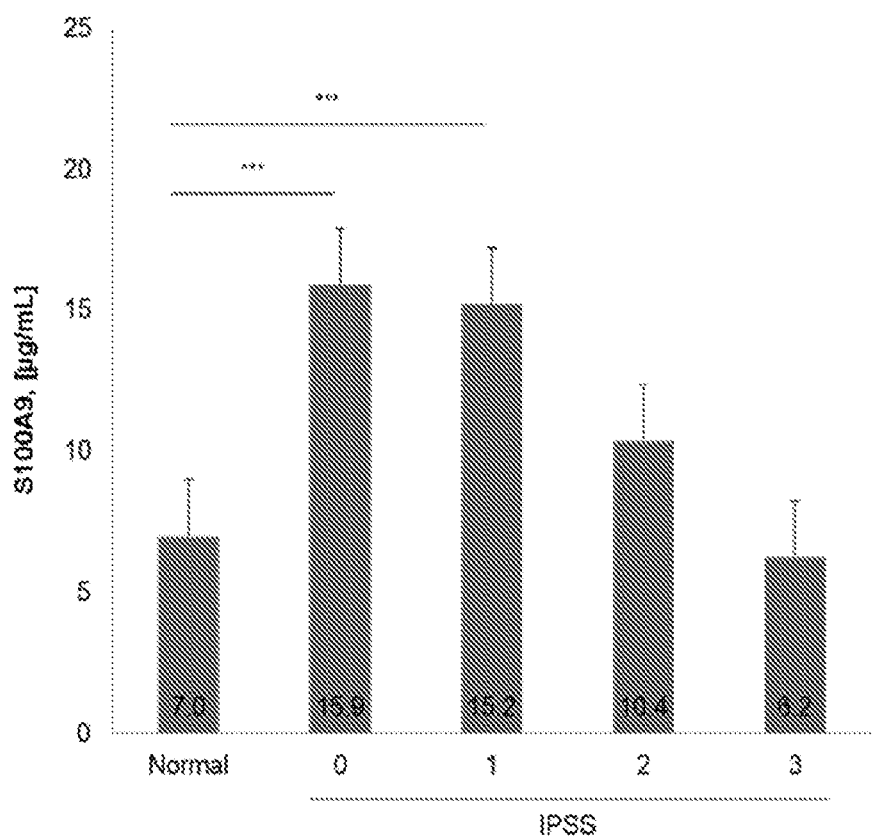
FIG. 10 shows plasma levels of S100A9 are elevated in MDS. BM plasma concentration of S100A9 was assessed by ELISA and analyzed according to IPSS risk score. Only MDS patients with lower-risk disease (IPSS=0, IPSS=1) demonstrate a statistically significant increase in BM plasma S100A9 concentration ($p=2.3\times10^{-5}$ and $1.0\times10^{-3}$, respectively). Error bars: SE, ***$p<0.001$.
Figure 11A:
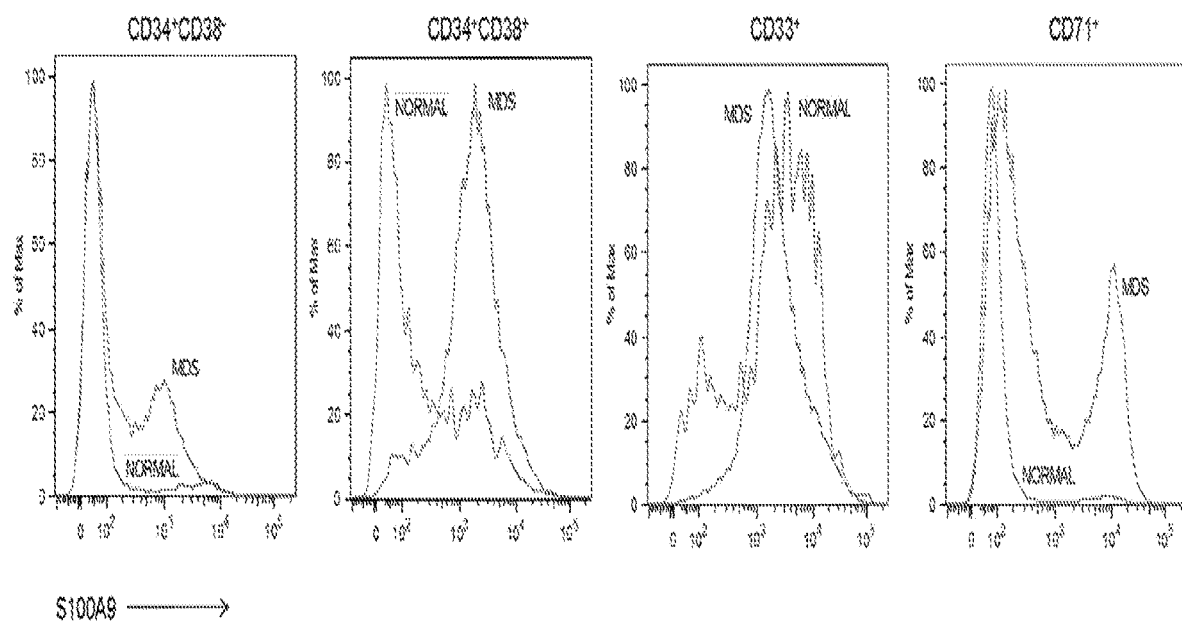
FIGS. 11A to 11C show intracellular levels of the alarmin S100A9 are increased across myeloid lineages. Intracellular levels of S100A9 were measured by flow cytometry in BM-MNC isolated from MDS patients (n=6) and normal controls (n=4).
Figure 11B:
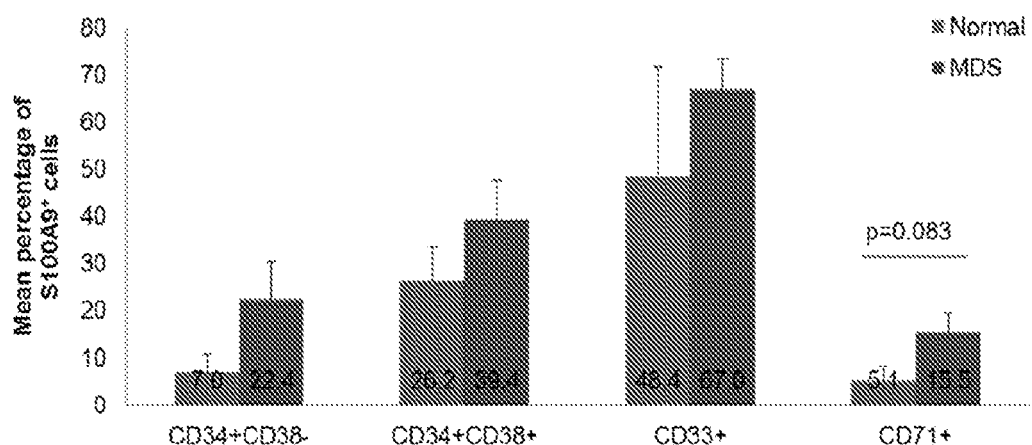
Figure 11C:
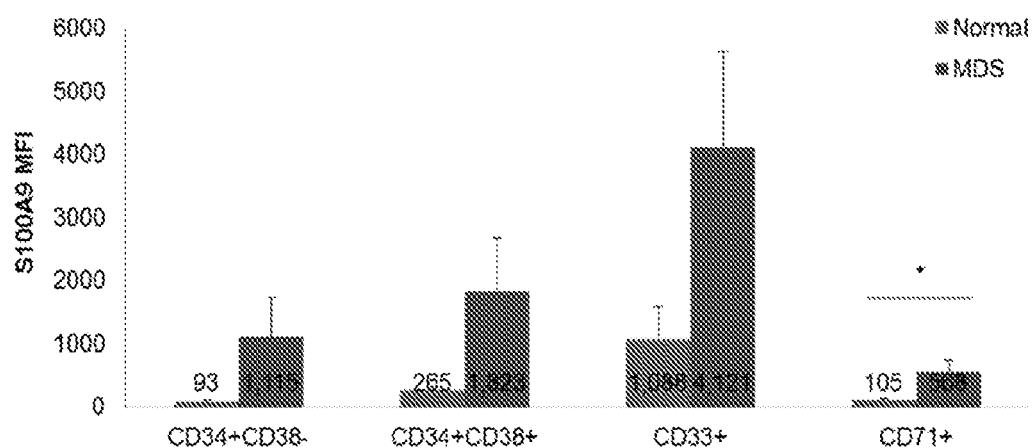
Figures 12A, 12B, 12C, 12D, 12E:
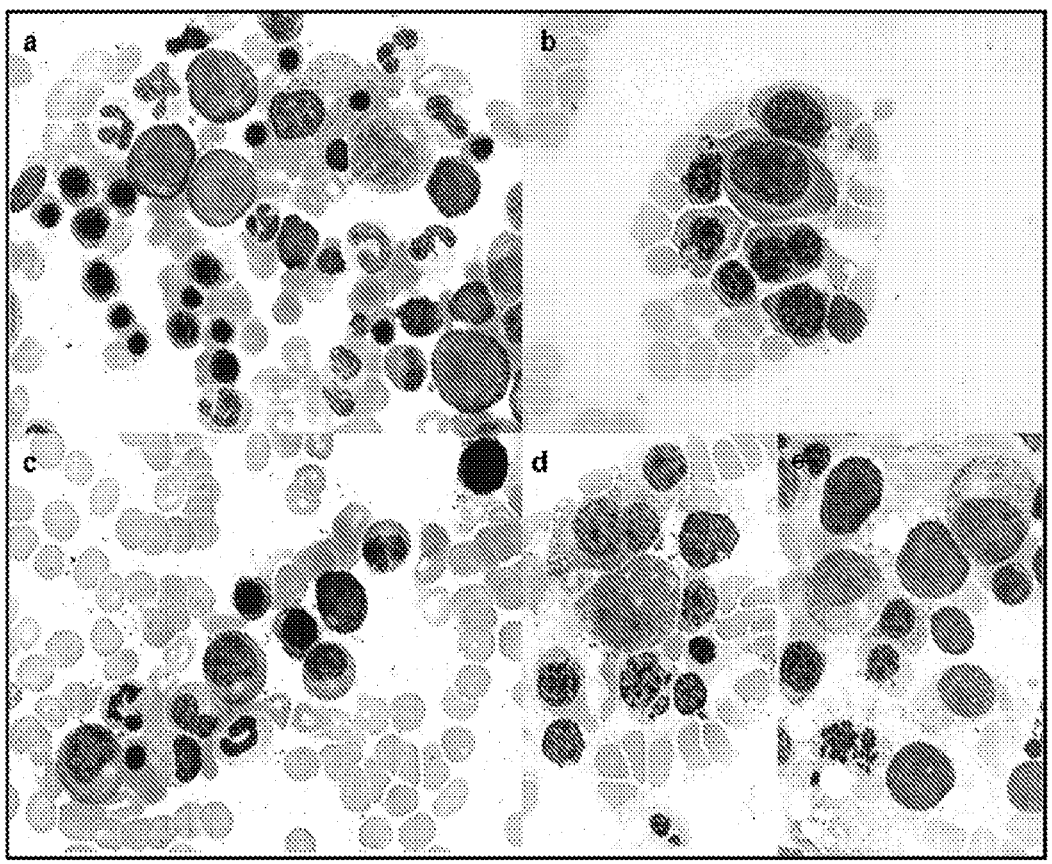
FIGS. 12A to 12E show increased size of MDS hematopoietic lineage cells. Images depict Wright-Giemsa staining (1000× magnification).

The BM plasma concentration of S100A9 was significantly higher in lower-risk patient specimens (n=33) compared to normal controls (n=12; p=1.5×10$^{-4}$), with no difference in higher-risk patient specimens (n=27, FIG. 2$a$). Analysis of S100A9 BM plasma concentration by International Prognostic Scoring System (IPSS) risk category showed a 2.3- and 2.2-fold increase in low risk (n=10, p=2.3×10$^{-5}$) and intermediate-I (n=23, p=1.0×10$^{-3}$), compared to normal controls (n=12), with no significant differences among controls and intermediate-II (n=17) or high risk (n=10) disease (FIG. 10). Notably, BM S100A9 concentrations were significantly higher in lower-risk versus higher-risk MDS (p=0.013) (FIG. 2a). In addition, the BM plasma concentration of HMGB1, a nuclear DAMP and TLR4 ligand, was significantly increased in MDS (n=55) versus normal controls (n=11) (p=2.6×10$^{-3}$) (FIG. 2b) (Velegraki M, et al. Haematologica. 2013 98(8):1206-15; Chirico V, et al. Eur J Pediatr. 2014 173(9): 1123-36). Moreover, S100A9 and HMGB1 gene expression were up-regulated 104.5-fold and 1.5-fold in MDS, respectively, compared to normal controls (FIG. 2c, 2d), and flow cytometric analysis confirmed a corresponding increase in cellular expression of the S100A9 alarmin in MDS stem cells and progeny (FIG. 11).

Figure 2A:
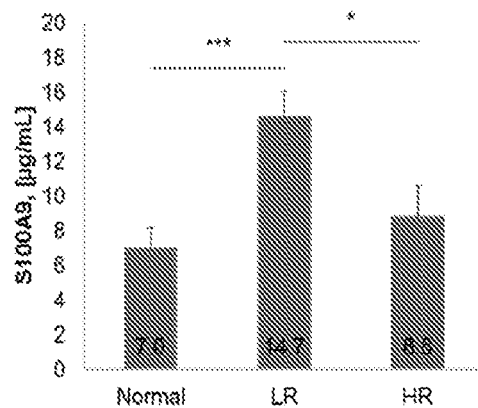
FIGS. 2A to 2G show S100A9 initiates pyroptosis in MDS.
Figure 2B:
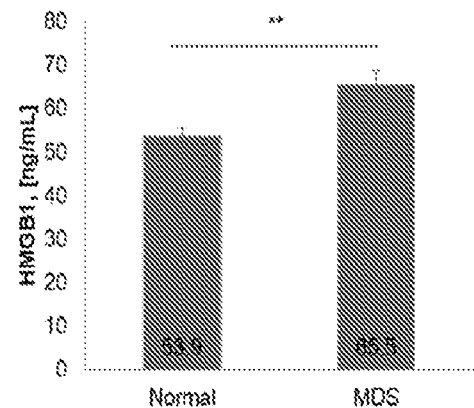
Figure 2C:
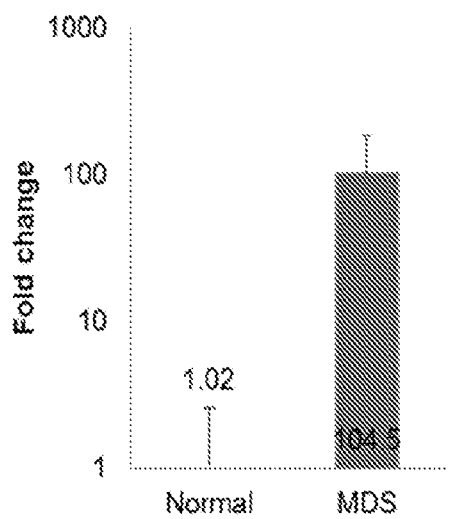
Figure 2D:
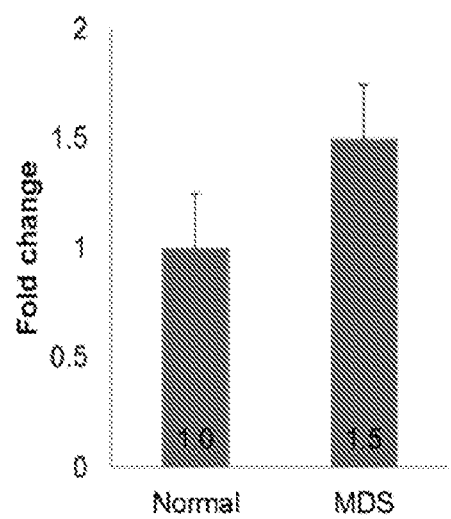
Figure 2E:
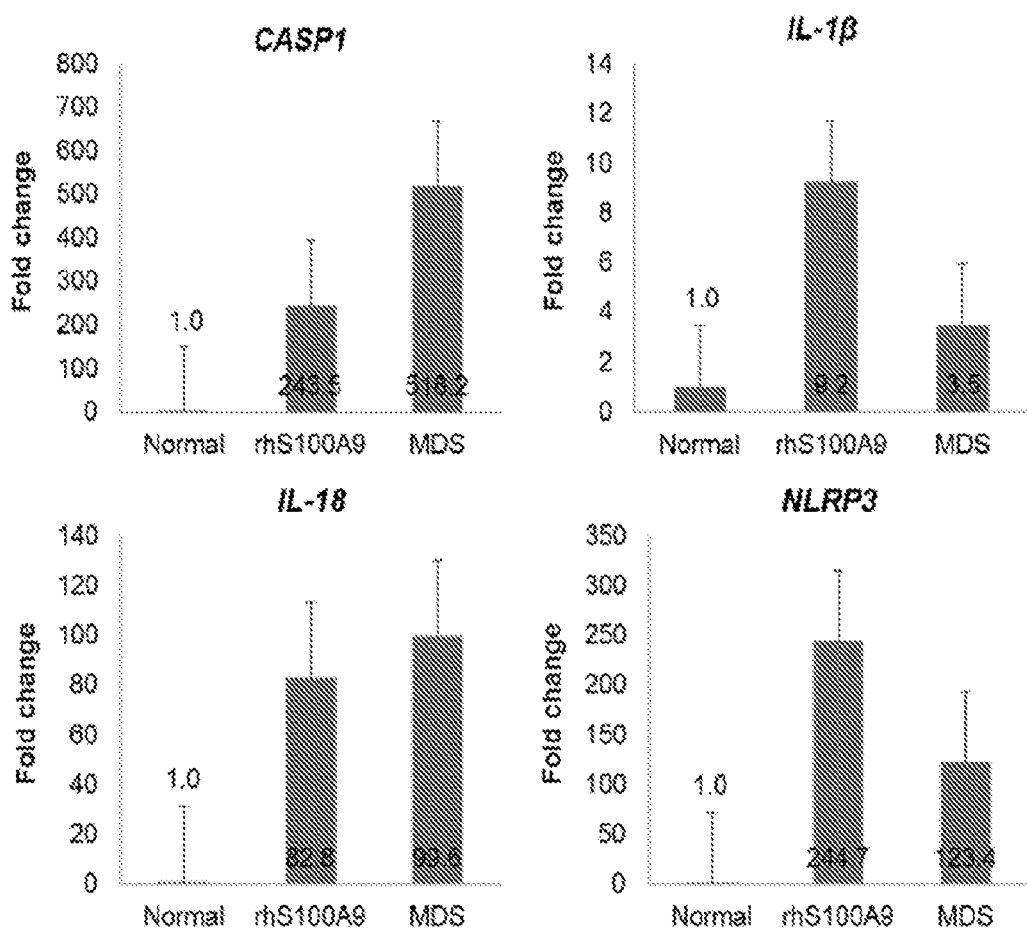
Figure 2F:
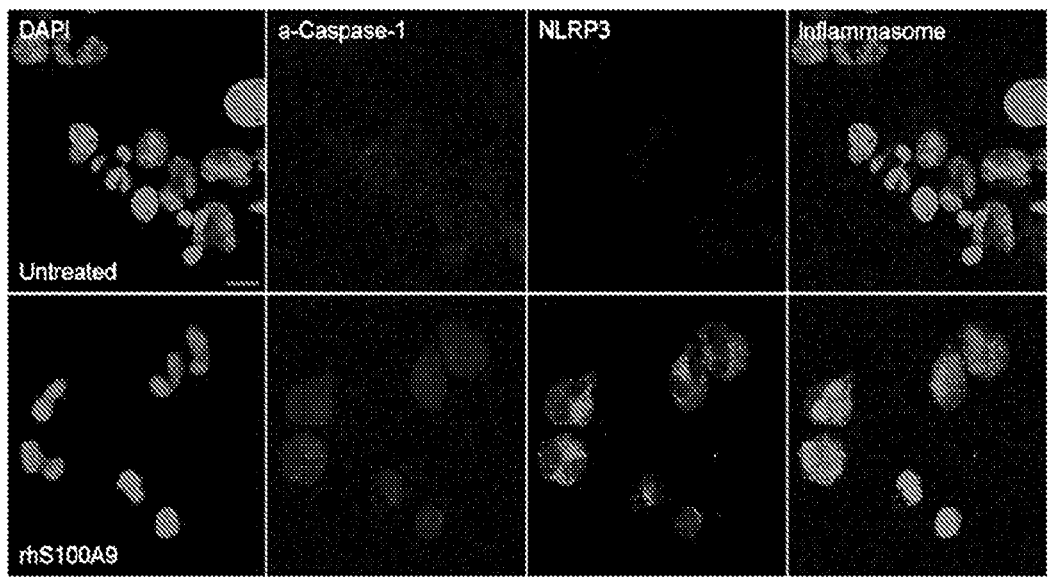
Figure 2G:
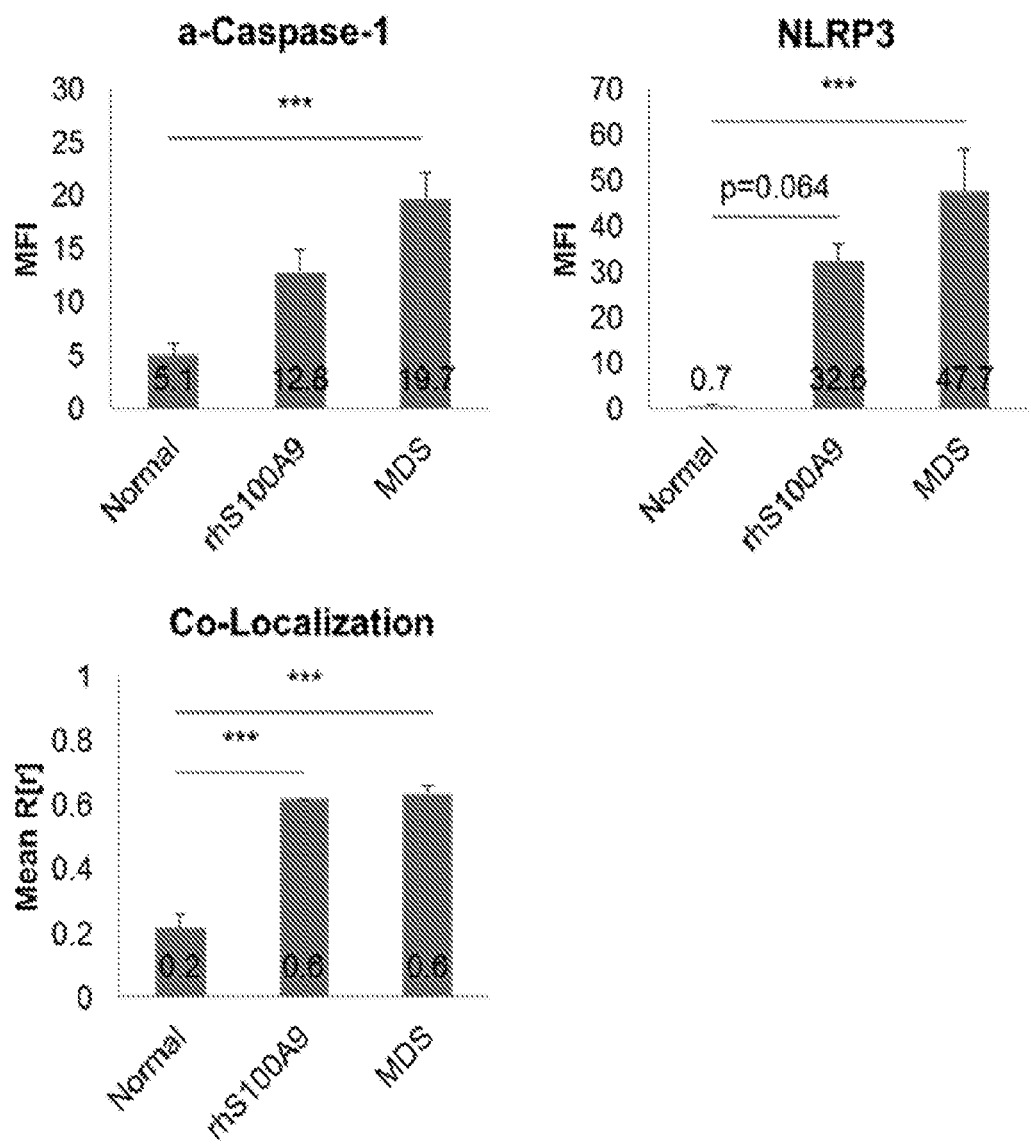

To determine if S100A9 directly triggers pyroptosis in HSPC, normal BM-MNC (n=2) were treated with 1 μg/mL rhS100A9 and changes in gene expression was assessed by qPCR. The expression of pyroptosis-associated genes was significantly up-regulated following addition of rhS100A9, for some to levels that surpass those detected in MDS (n=5) (FIG. 2e). Accordingly, a-caspase-1 and NLRP3 levels were induced following treatment of normal BM-MNC with 5 μg/mL rhS100A9 (FIG. 2f), by 2.5-fold and 47.1-fold (p=0.064), respectively, as were formation of NLRP3 inflammasomes, by 2.9-fold (p=3.1×10$^{-4}$) (FIG. 2g). Finally, although rhS100A9 treatment induced inflammasome assembly and caspase-1 activation in normal controls, MDS patient specimens (n=10) displayed greater activation and co-localization of these effectors.

Inflammasome-Initiated Pore Formation Increases Size of MDS Precursors

Figure 3A:
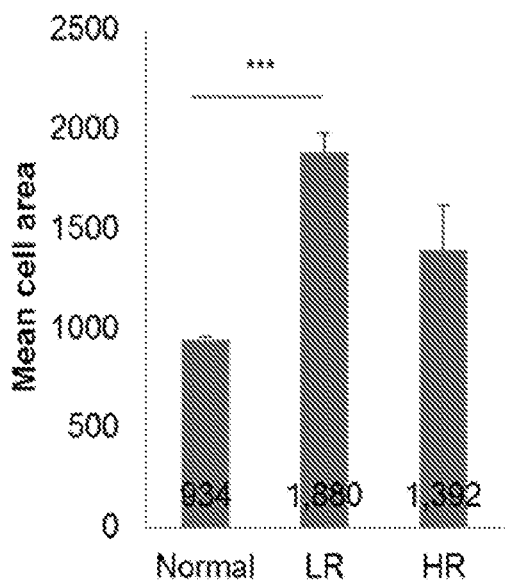
FIGS. 3A to 3J show inflammasome-initiated pore formation increases size of MDS precursors.
Figure 3B:
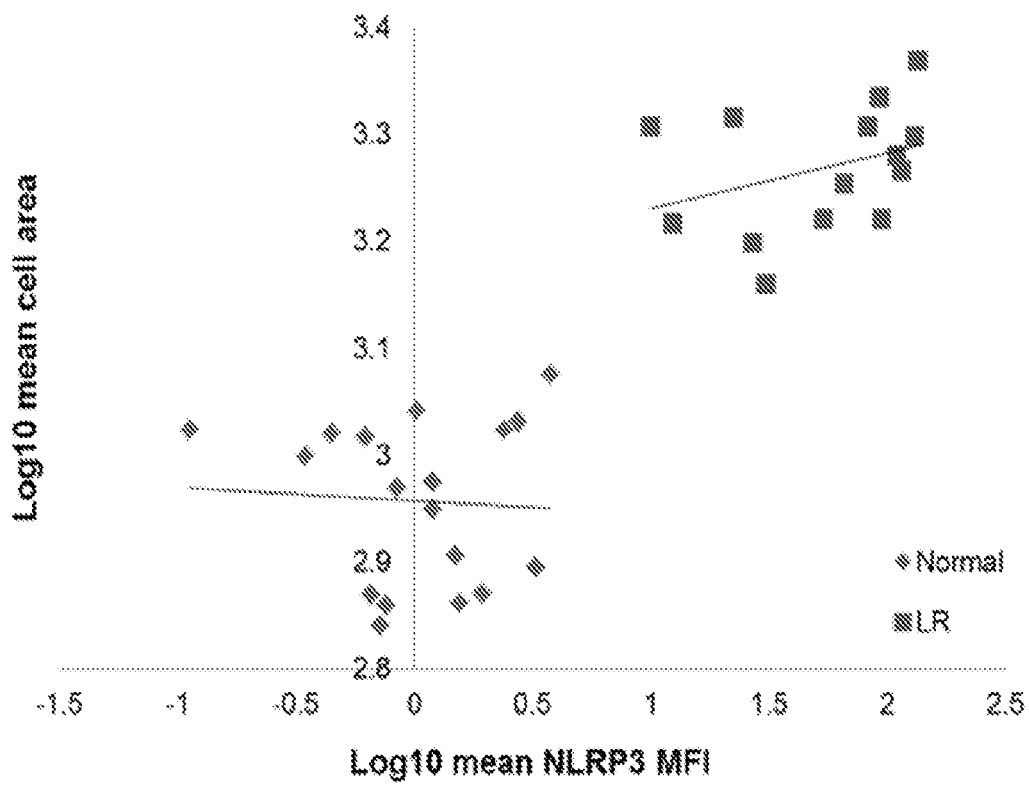
Figure 3C:
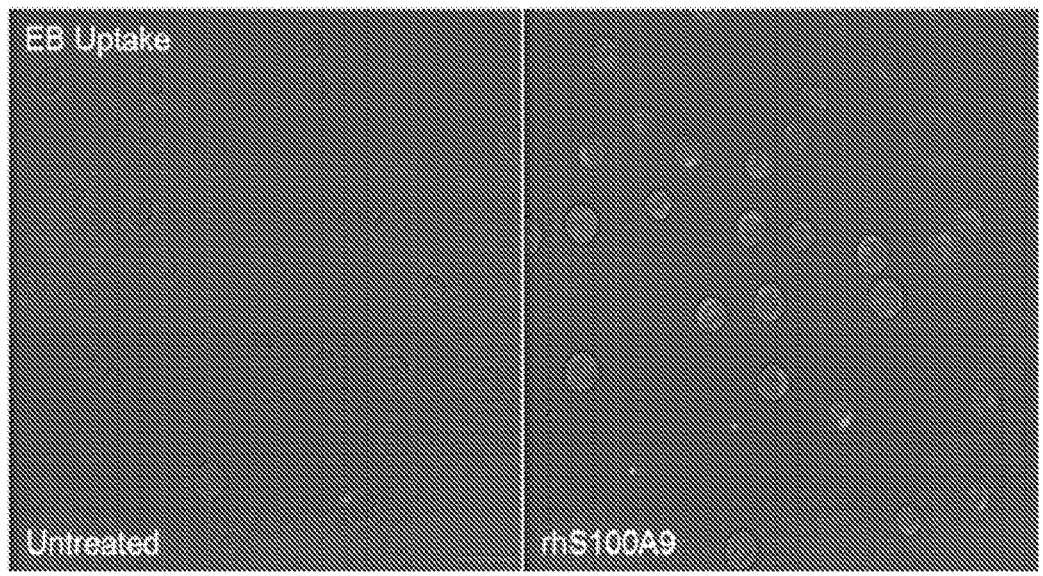
Figure 3D:
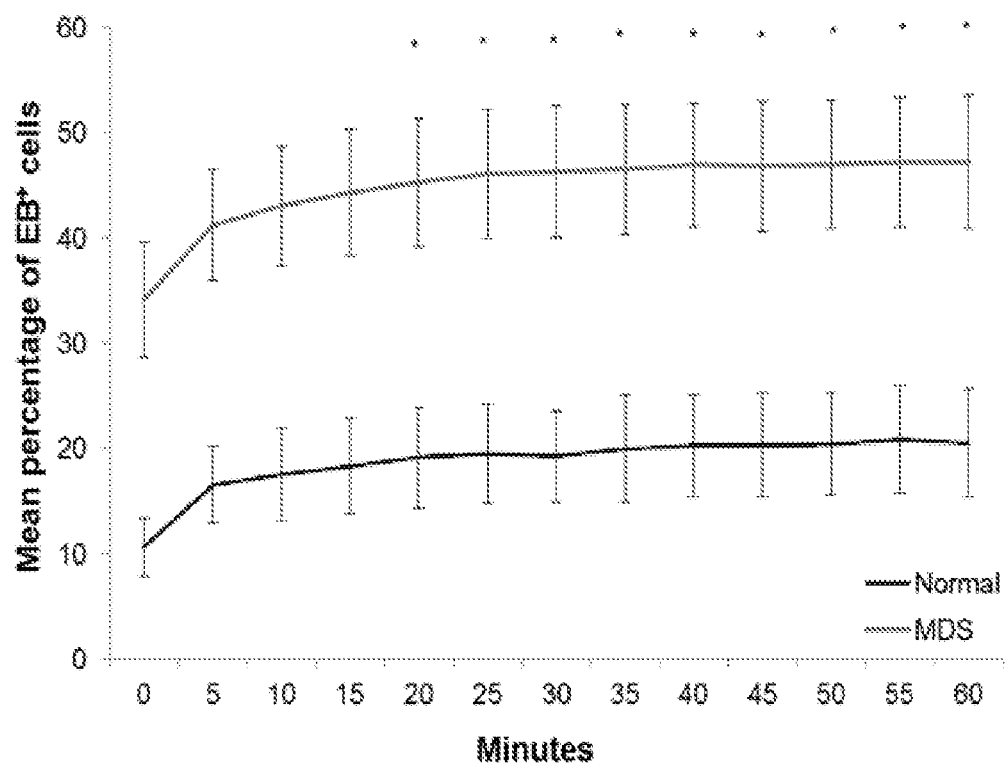
Figures 3E, 3F, 3G, 3H:
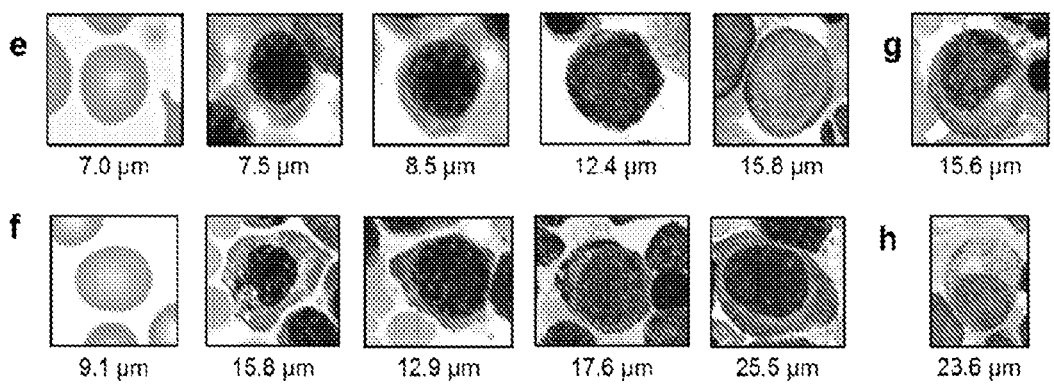
Figure 3I:
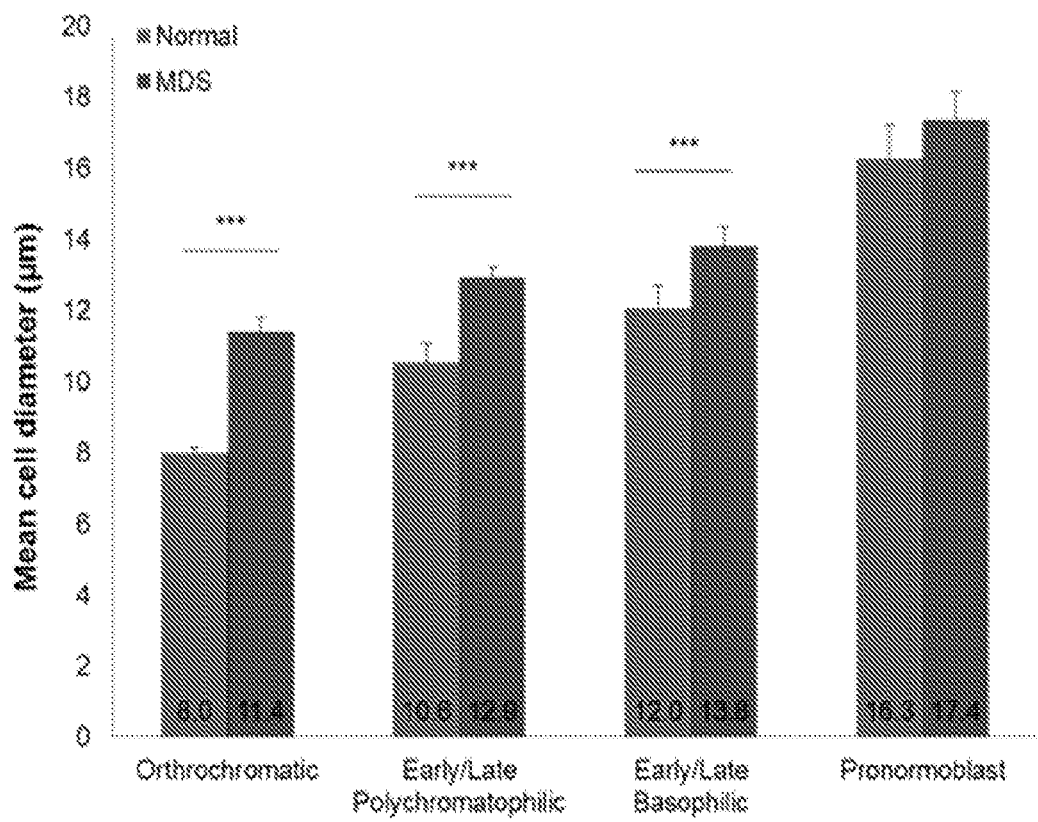
Figure 3J:
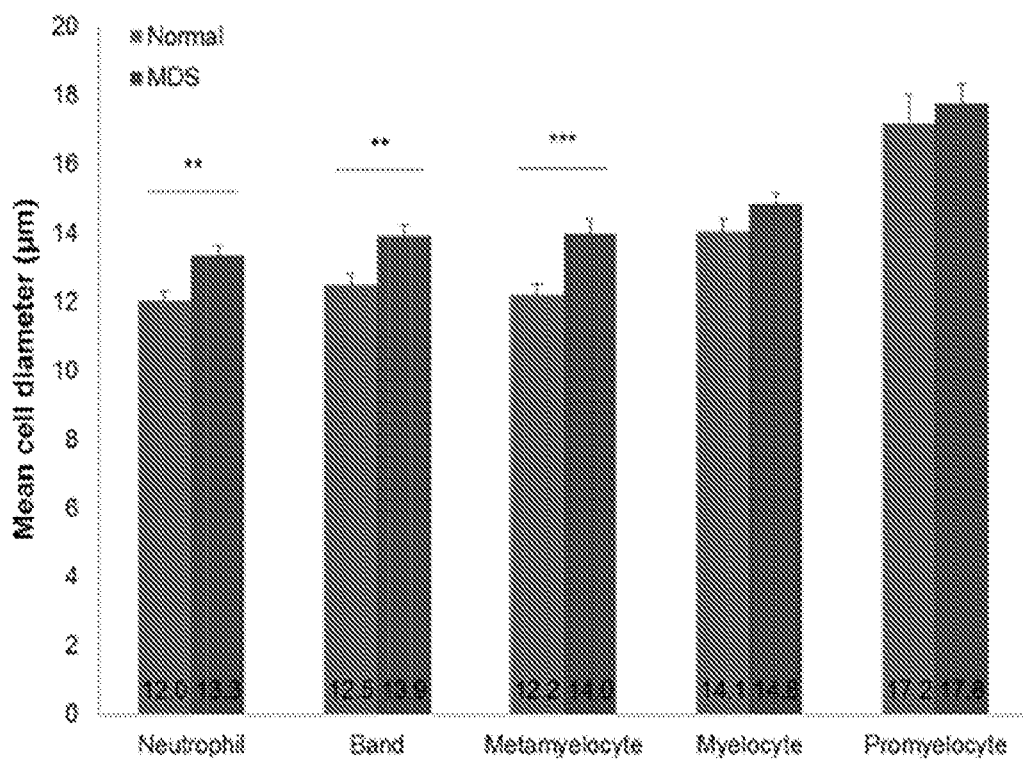

Cell swelling is a hallmark of pyroptosis. This occurs following caspase-1-mediated activation of plasma membrane cation channels, which compromises membrane integrity and disrupts osmolality (Fink S. L. & Cookson B. T. Cell Microbiol. 2006 8(11):1812-25). Confocal image analyses of MDS BM-MNC cells demonstrated significantly larger mean cell area compared to normal controls (FIG. 3a). This phenotype was accentuated in lower-risk MDS patients compared to normal controls (p=6.0×10$^{-5}$), with no significant difference detected in higher-risk patients. Further, there was a positive correlation between mean NLRP3 MFI and mean cell area in lower-risk (but not higher-risk) MDS patients (r=0.49) (p=7.8×10$^{-3}$) (FIG. 3b). To assess pore formation, influx of the membrane-impermeable, cationic dye ethidium bromide was assessed by immunofluorescence. As predicted, monocytic U937 cells treated with rhS100A9 demonstrated rapid and substantial uptake of ethidium bromide (FIG. 3c). Further, flow cytometric analyses of ethidium bromide uptake demonstrated that MDS specimens incubated with autologous bone marrow plasma had rapid and sustained elevated dye influx versus that of BM-MNC from normal donors, which was demonstrable as early as 20 minutes (p=0.041), and remained significant through 1 hour of dye exposure (p=0.014) (FIG. 3d). Finally, analysis of normal and MDS bone marrow aspirate morphology confirmed the larger cell size by maturation stage and lineage in MDS (FIGS. 3e-j, 12).

Inhibition of Pyroptosis Improves Hematopoiesis in MDS

Figure 4A:
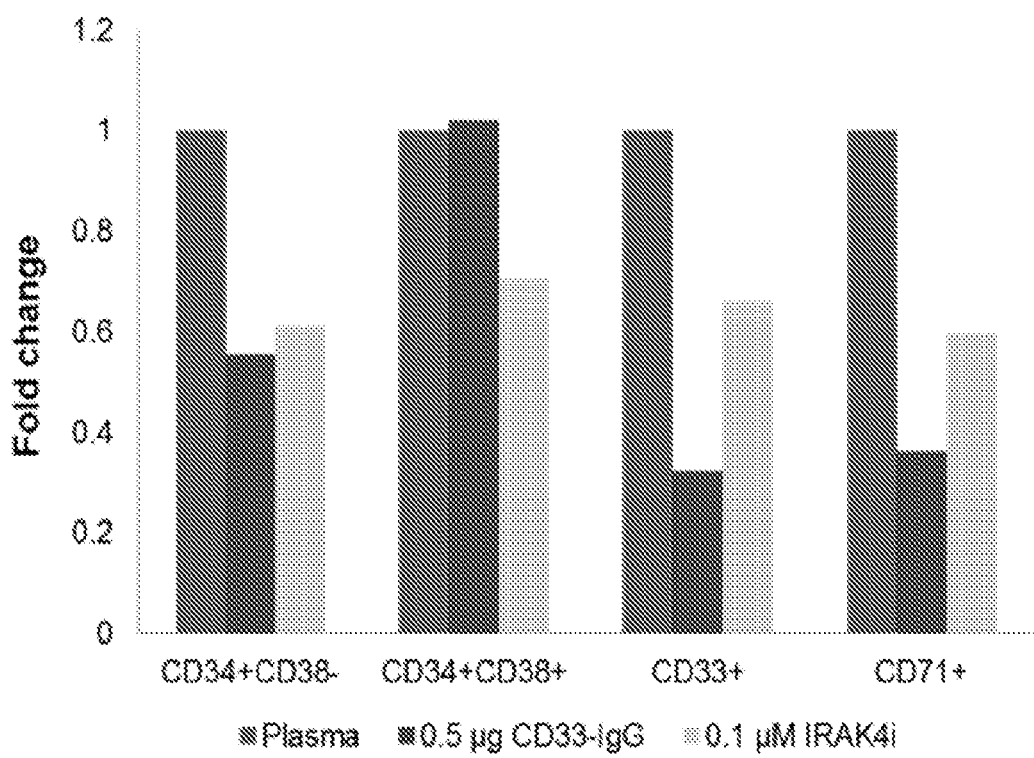
FIGS. 4A to 4E show inhibition of pyroptosis abrogates MDS HSPC cell death and augments colony forming capacity.
Figure 4B:
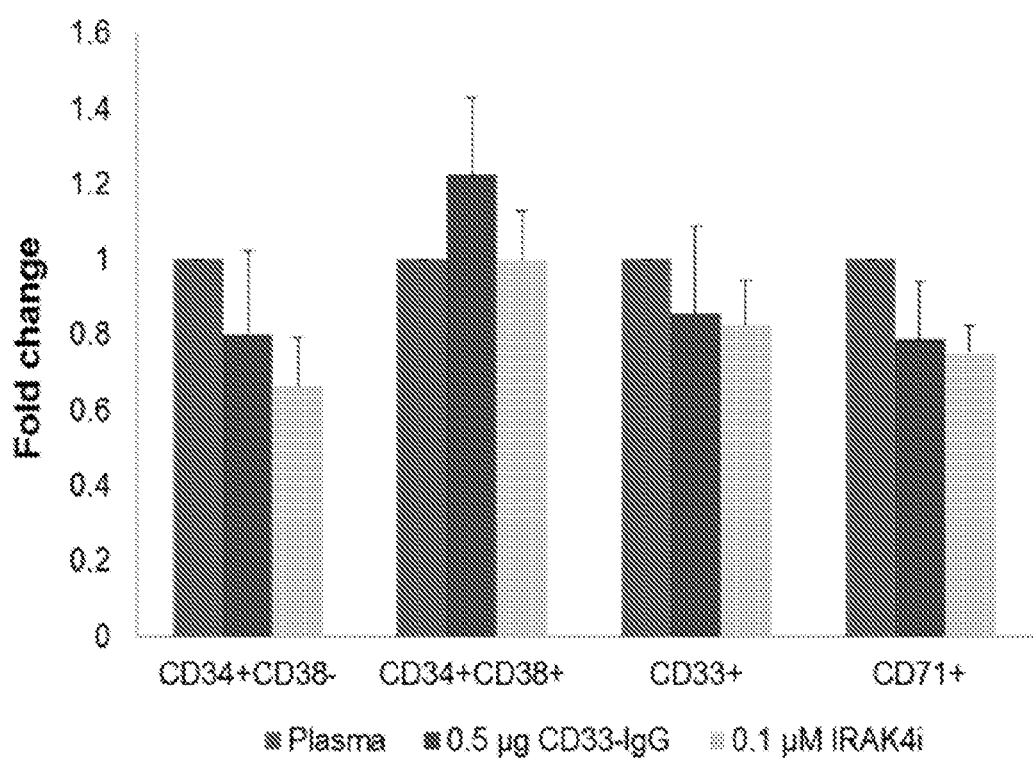
Figure 4C:
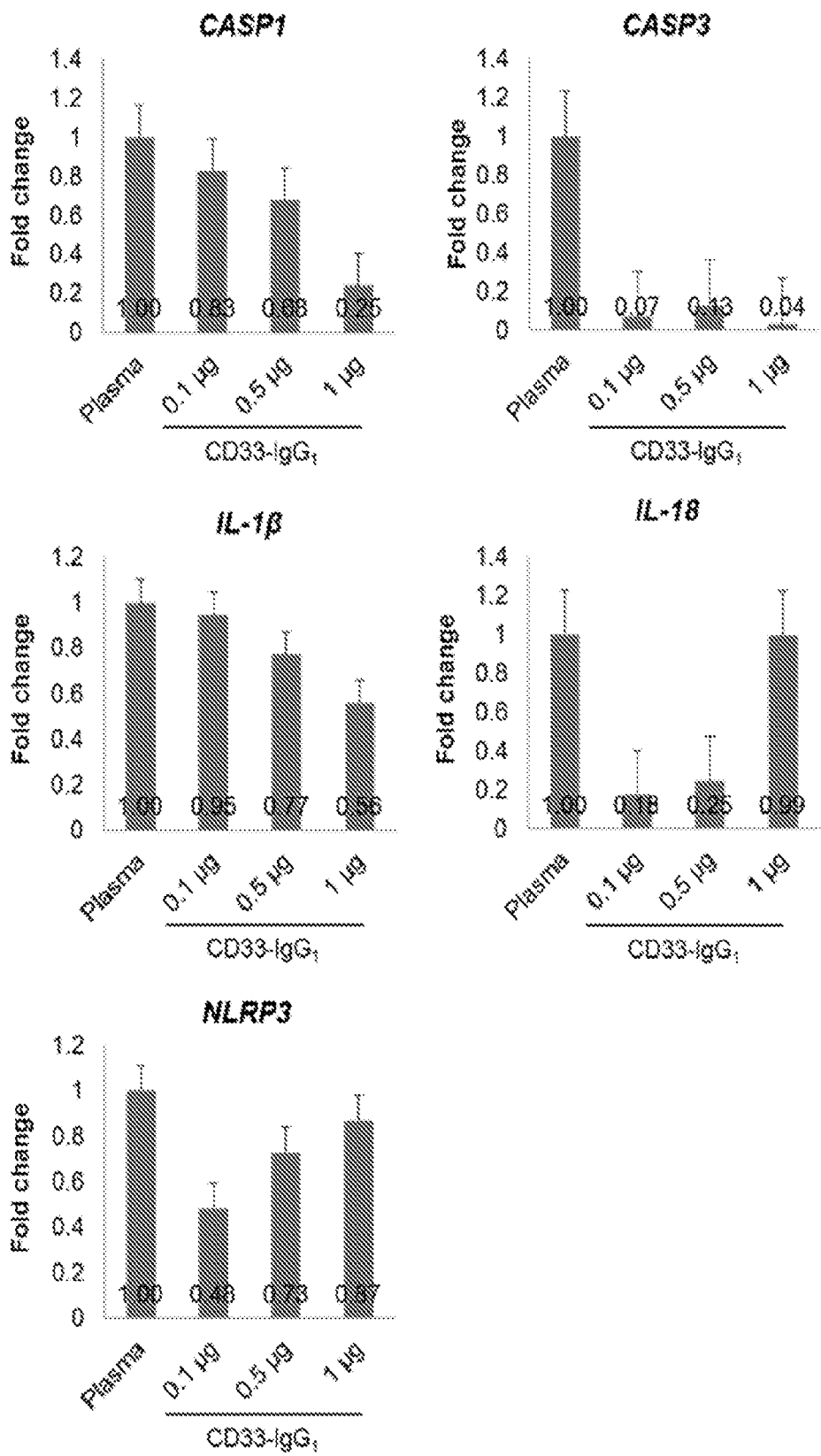

To assess the role of S100A9 in the pyroptosis phenotype evidenced in MDS, experiments were conducted to assess the effects of a S100A9 high-affinity chimeric (CD33-IgG$_1$) decoy receptor or of an IRAK4 inhibitor on phenotypes manifest in BM-MNC (n=4) from MDS patients treated with autologous BM plasma. Notably, treatment with CD33-IgG$_1$ or the IRAK4 inhibitor led to marked reduction in the fraction of pyroptotic cells across all lineages studied (FIG. 4a). Overall, short-term incubation with the chimera or the IRAK4 inhibitor reduced the fraction of pyroptotic cells, with corresponding maximum lineage-specific changes in stem cells (44% vs. 75%, respectively), progenitor cells (23% vs. 36%, respectively), CD33$^+$ (68% vs. 55%, respectively) and CD71$^+$ cells (64% vs. 55%, respectively) (FIG. 4b.). Short-term treatment with the chimeric receptor also significantly reduced the MDSC fraction, suggesting that S100A9 neutralization impairs the survival of MDSC. Consistent with this, the CD33 chimera reduced expression of CASP1, IL-1β, IL-18, and NLRP3 versus autologous BM plasma alone (n=5) (FIG. 4c). CASP3 expression was also markedly reduced, which is consistent with caspase-3 being activated downstream of caspase-1 after late mitochondrial depolarization (Ali A, et al. J Hematother Stem Cell Res. 1999 8(4):343-56). High concentrations of the chimera led to cross-linking of the IgG$_1$-Fc domains and aggregation that masked dose-dependent effects of S100A9 neutralization.

Figure 4D:
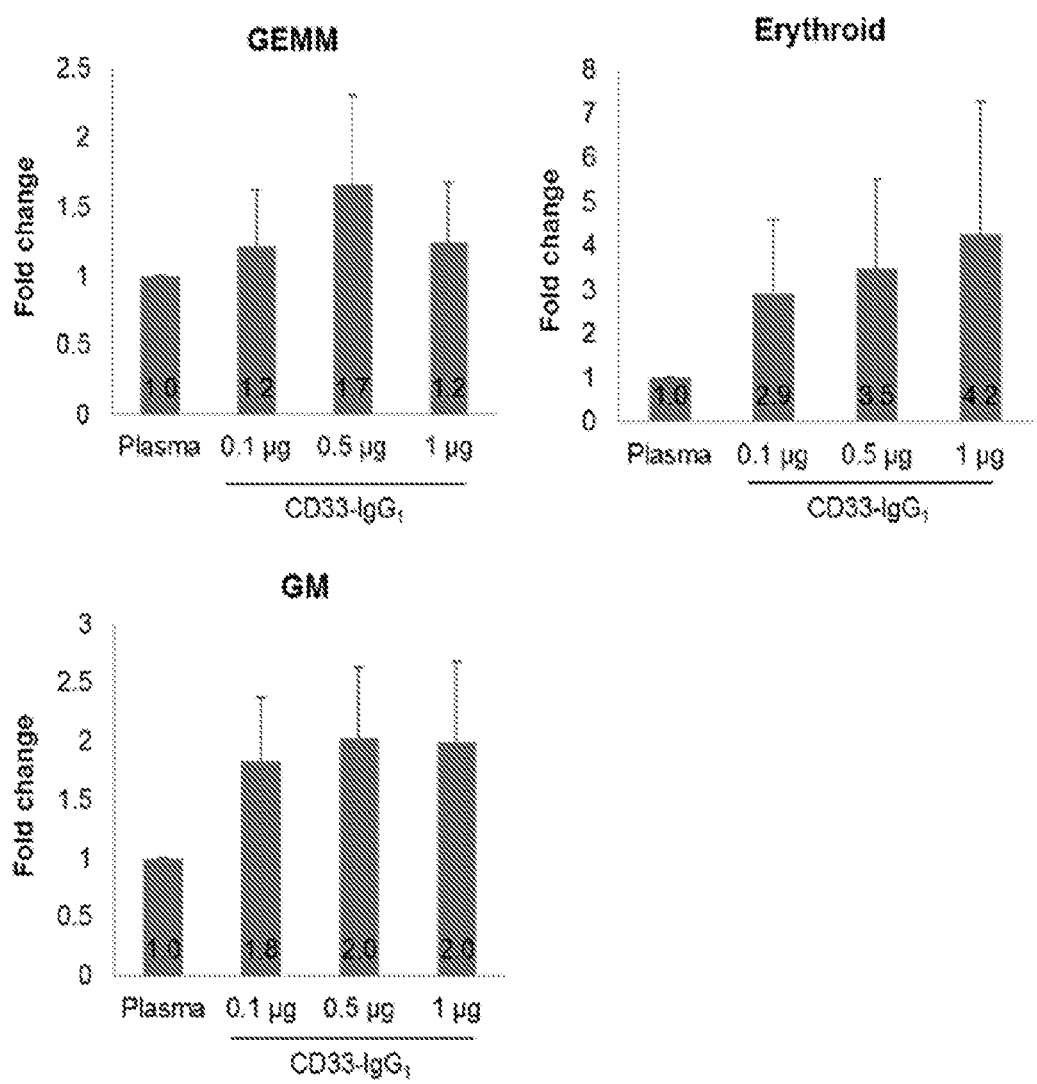
Figure 4E:
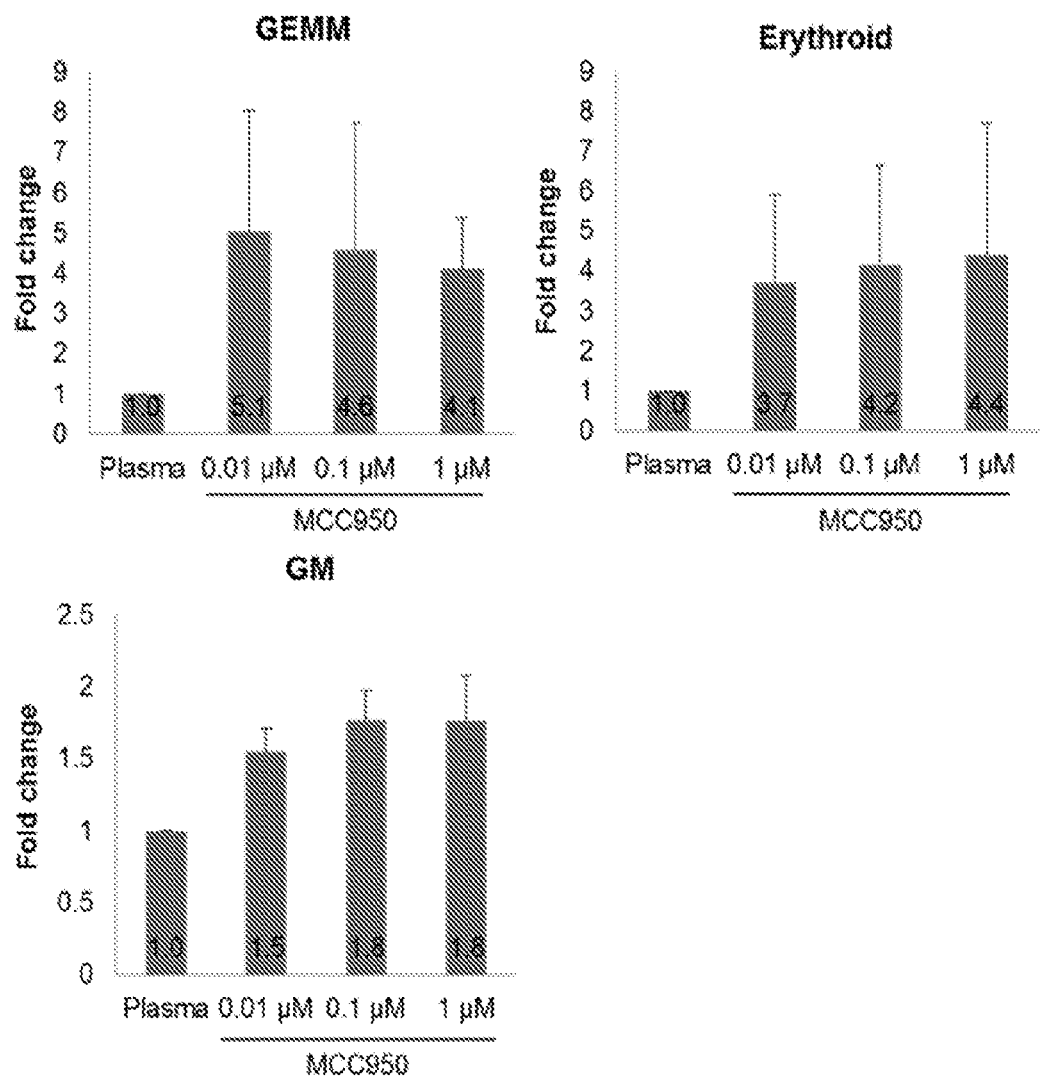

To test if S100A9 neutralization could improve hematopoiesis in MDS, colony forming capacity was assessed after plating of MDS BM-MNC in autologous BM plasma and increasing concentrations of CD33-IgG$_1$ (FIG. 4d) or of MCC950 (FIG. 4e), a small molecule inhibitor of NLRP3 (Coll R. C, et al. Nat Med. 2015 21(3):248-55). Neutralization of S100A9 or inhibition of the NLRP3 inflammasome markedly improved colony-forming capacity (up to 6.6-fold greater than controls). Thus, pyroptotic pathway inhibition abrogates MDS hematopoietic cell death and promotes effective hematopoiesis.

S100A9 is Sufficient to Provoke HSPC Pyroptosis In Vivo

Figure 5A:
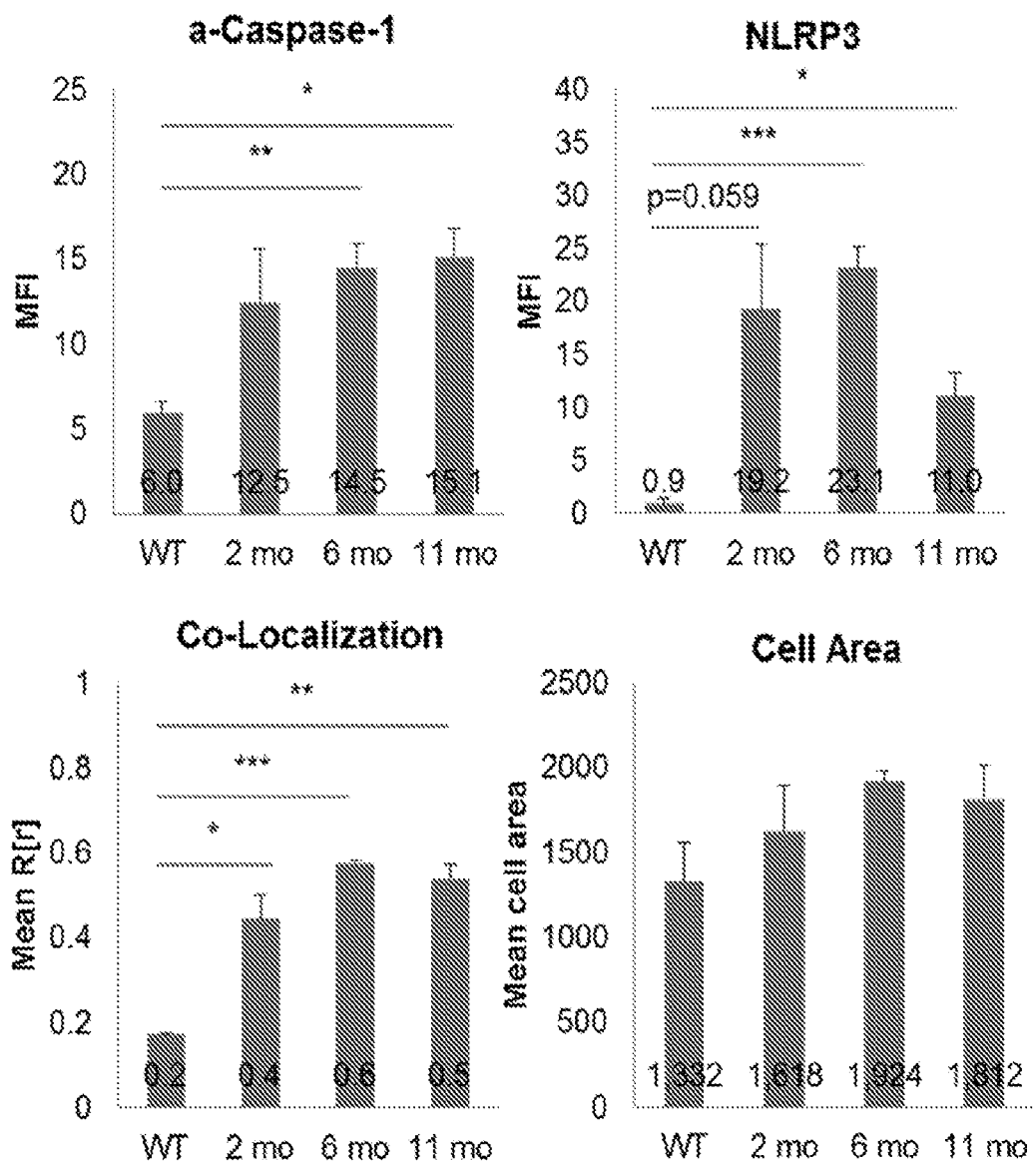
FIGS. 5A to 5H show pyroptosis is the principal mechanism of HSPC death in S100A9 transgenic mice.

To assess whether forced expression of S100A9 was sufficient to induce pyroptosis in vivo, an S100A9 transgenic (S100A9Tg) mouse model was investigated that phenocopies human MDS (Chen X, et al. J Clin Invest. 2013 123 (11):4595-611). Confocal fluorescence microscopy analyses of BM cells from the tibia and femurs of S100A9Tg versus wild type (WT) mice at 2 (n=4), 6 (n=4), and 11 (n=5) months of age established that a-caspase-1 levels selectively increased in an age-dependent manner in the BM of S100A9 transgenics, with a 2.1-fold up-regulation at 2 months, 2.4-fold at 6 months (p=3.3×10$^{-3}$), and 2.5-fold at 11 months (p=0.010) versus WT mice. Similarly NLRP3 levels were increased in S100A9Tg mice, with a 21.1-fold up-regulation at 2 months (p=0.0$^{59}$), 25.6-fold at 6 months (p=2.2×10$^{-4}$), and 12.1-fold at 11 months (p=0.018) (FIG. 5a). Accordingly, formation of NLRP3 inflammasome complexes was significantly increased in an age-dependent fashion, with 2.6-fold greater co-localization in the 2 month old S100A9Tg transgenic mice (p=0.017), 3.3-fold in the 6 month (p=1.0×10$^{-6}$), and 3.2-fold in 11 month old mice (p=1.2×10$^{-3}$) (FIG. 5a). Though transgenic mice illustrate a marked increase in mean cell area at each time point, there was no significant difference in cell size between WT and transgenic mice.

Figure 5B:
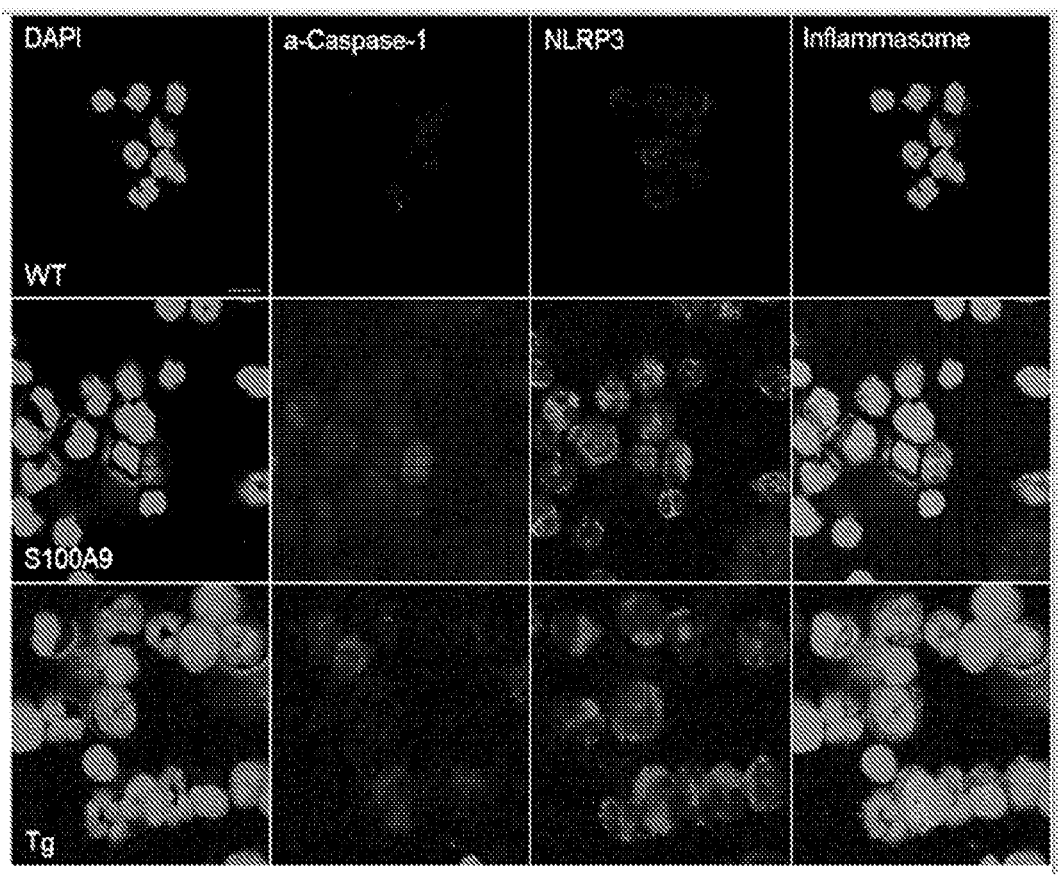
Figure 5C:
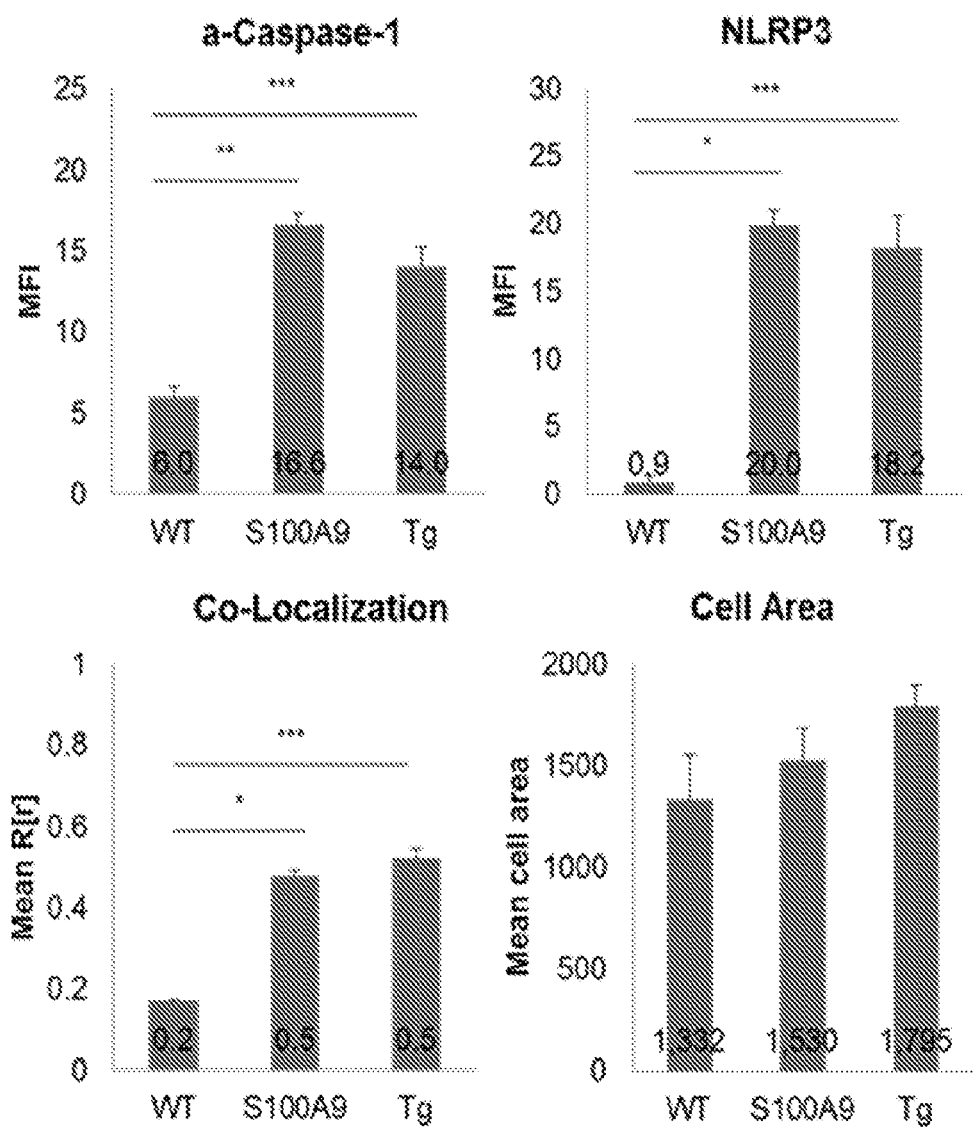
Figure 5D:
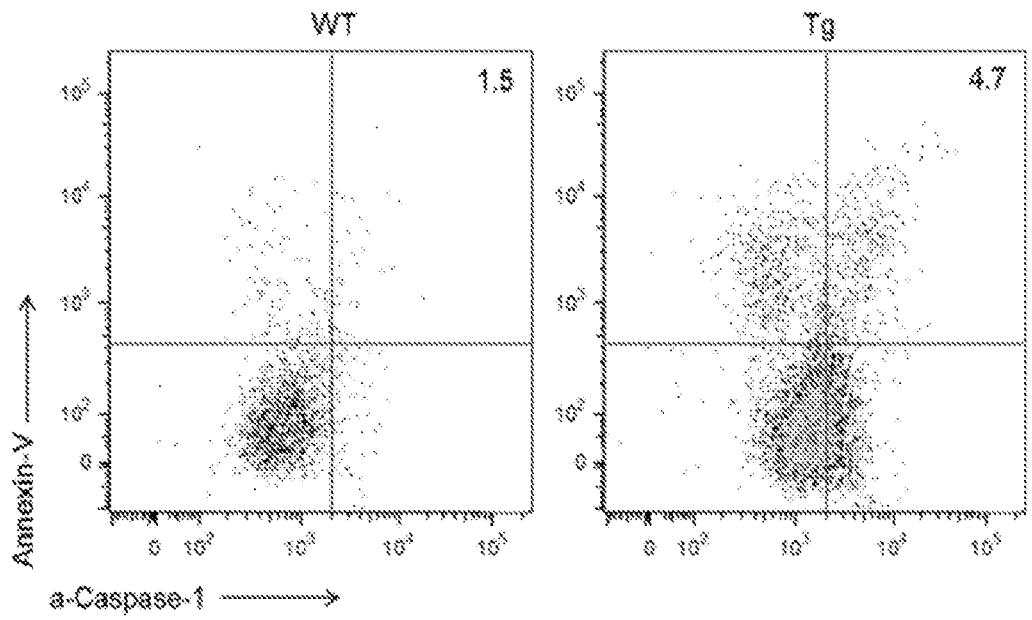
Figure 5E:
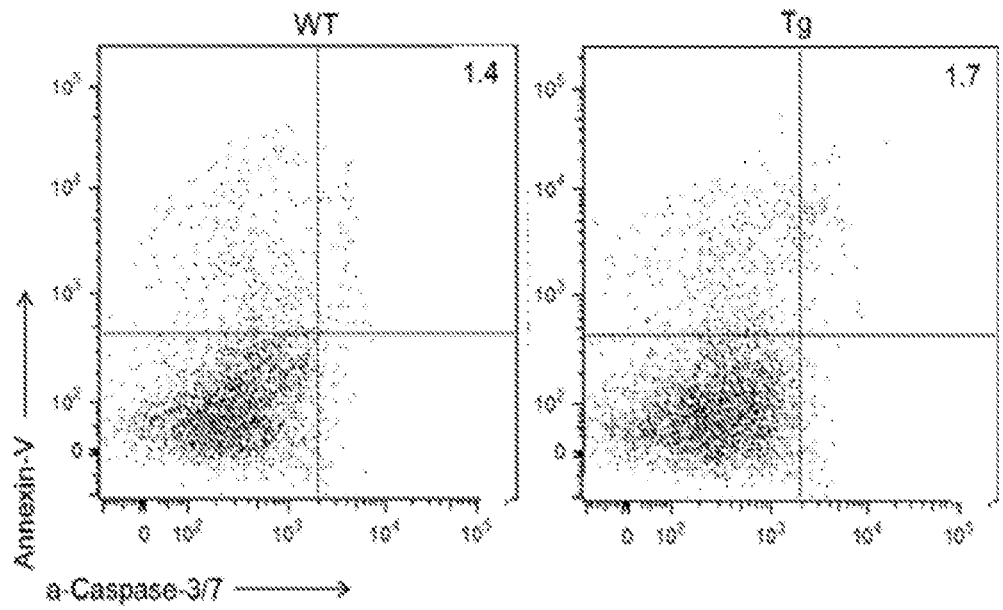
Figure 5F:
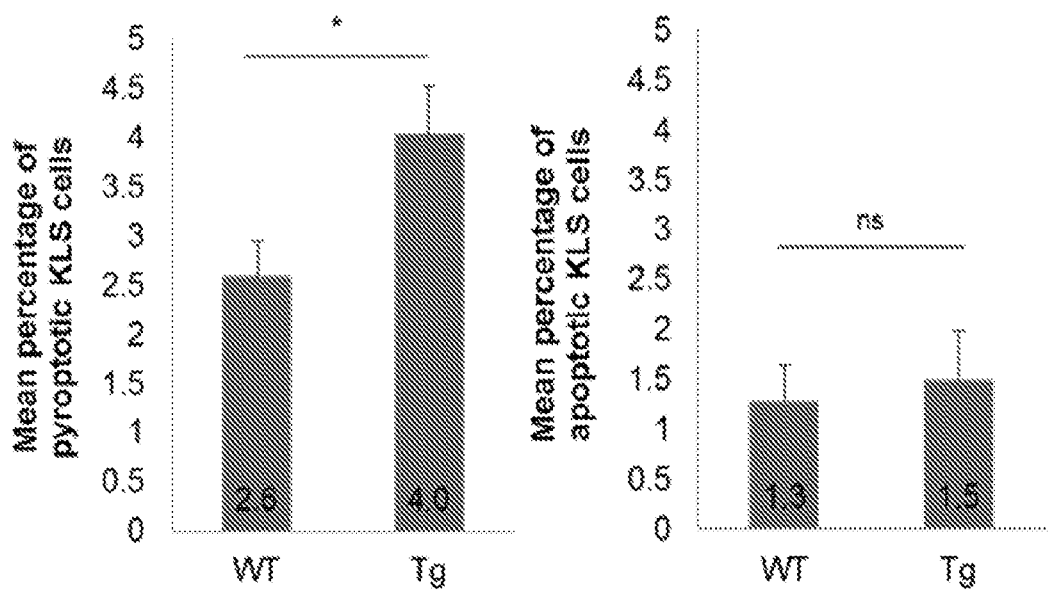
Figure 5G:
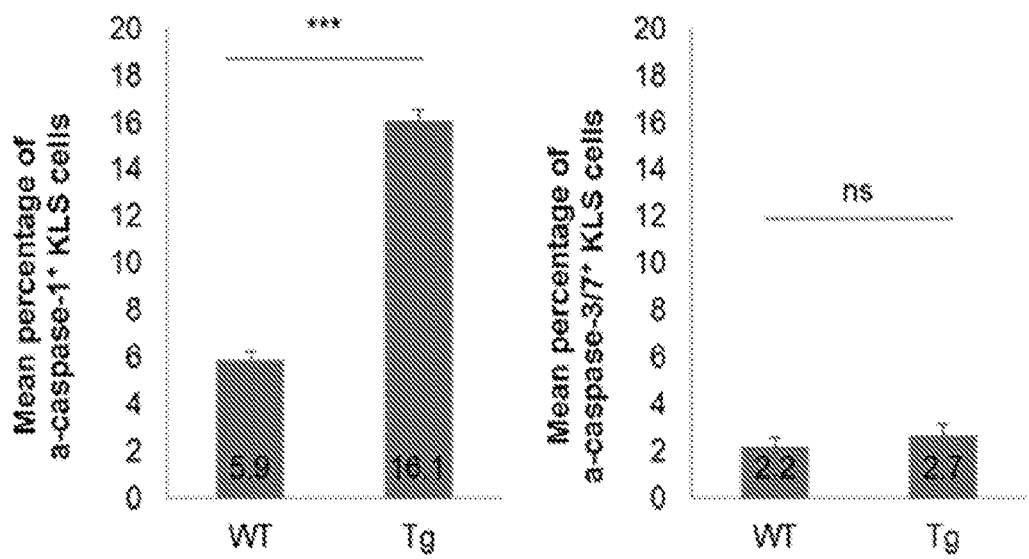
Figure 5H:
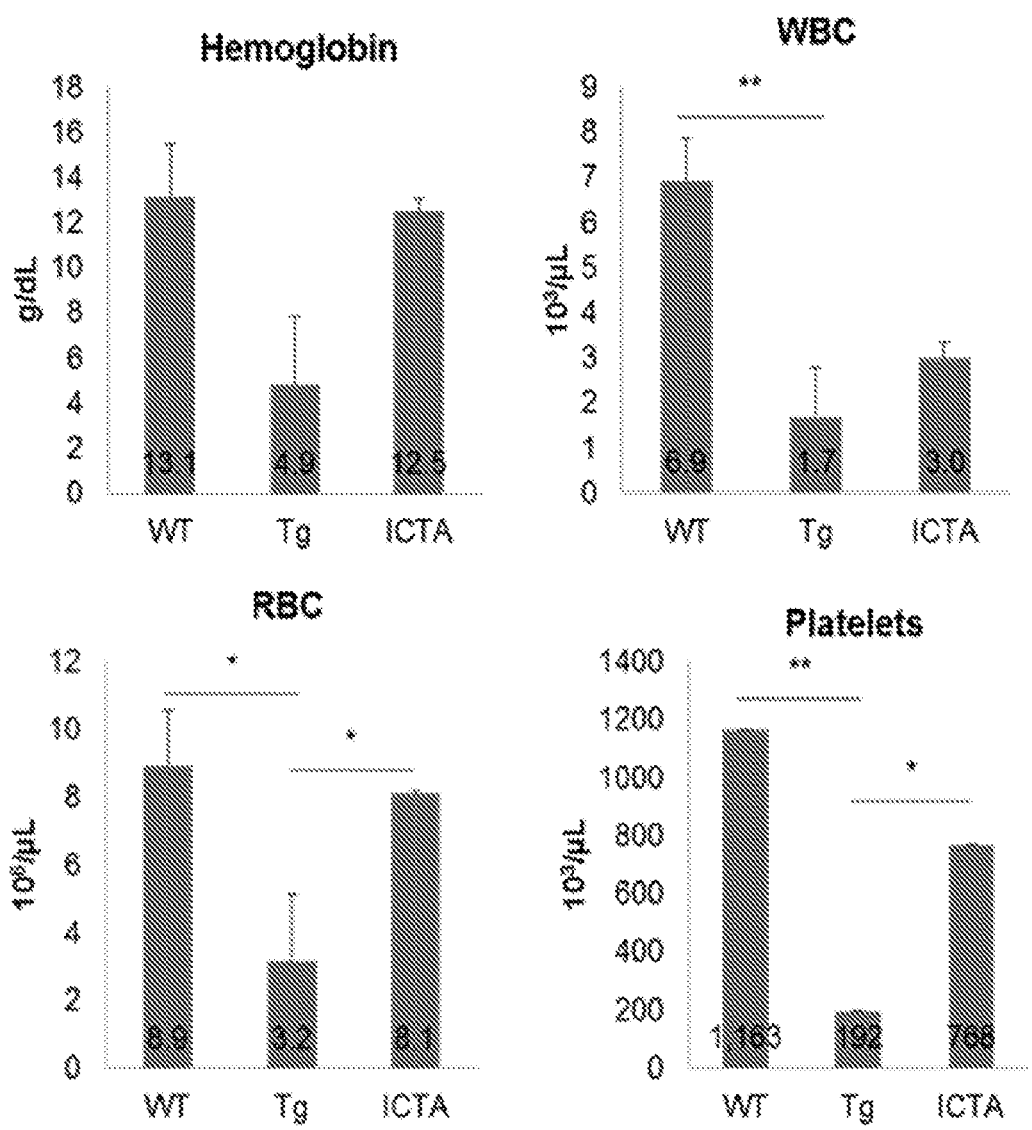
Figure 13A:
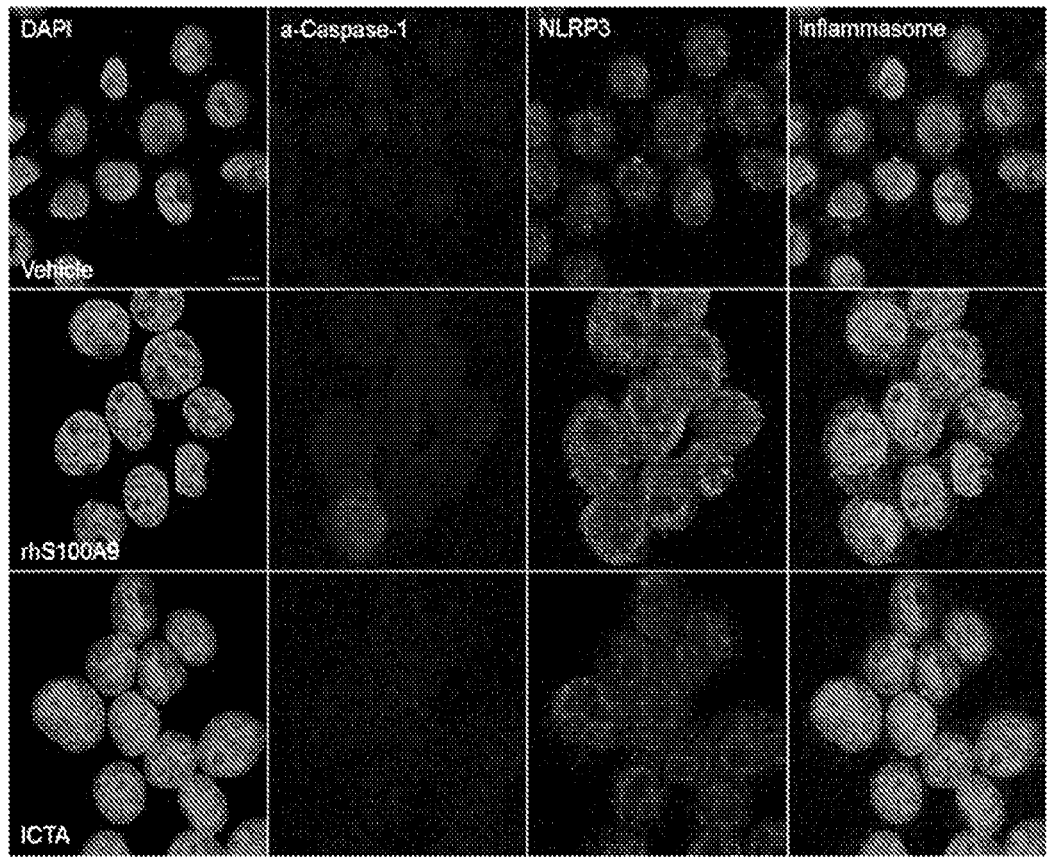
FIGS. 13A and 13B show ICTA inhibits inflammasome activation.
Figure 13B:
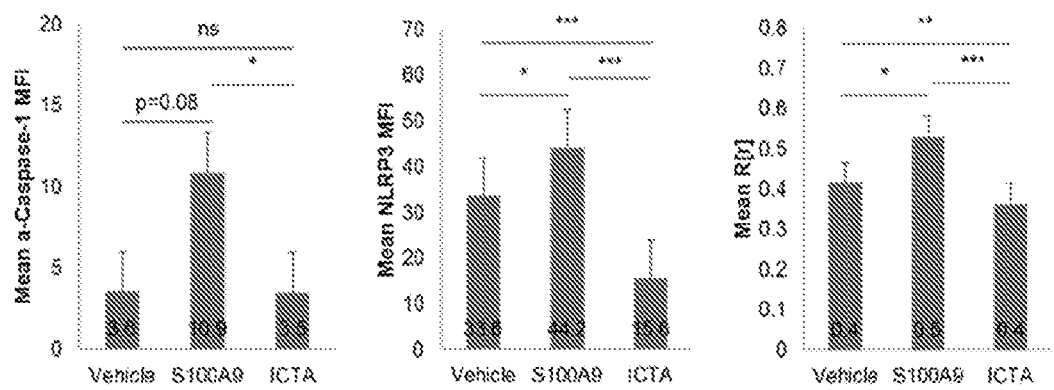

To test if S100A9 triggers pyroptosis in mouse hematopoietic cells, BM cells isolated from WT mice were treated with 5 μg/mL rhS100A9 and inflammasome formation was assessed by confocal microscopy (FIG. 5b, 5c). As predicted. MFI of a-caspase-1 and NLRP3 were both significantly increased after rhS100A9 treatment (n=2) versus controls (n=2) (p=7.5×10$^{-3}$ and 0.017, respectively). Notably, MFI values from rhS100A9 treated BM cells of WT mice were comparable to those manifest in the BM cells of S100A9 transgenic mice (n=13) (FIG. 5c), and rhS100A9 treatment of WT BM cells was associated with a marked induction of inflammasome complexes (p=0.023). To assess the extent of pyroptosis versus apoptosis in the corresponding mice, BM cells were isolated from 7 month old WT (n=6) and 9 month old S100A9Tg mice (n=6). Active caspase-1 and a-caspases-3/7 were assessed by flow cytometry in the KLS (c-Kit$^+$Lin$^-$Sca-1$^+$) hematopoietic stem and progenitor cell population (FIG. 5d, 5e). The mean percentage of pyroptotic KLS cells was significantly increased in the S100A9Tg animals versus WT mice (p=0.038), whereas there were no significant differences in the mean percentage of apoptotic cells (FIG. 5f). Additionally, the total percentage of a-caspase-1$^+$ KLS cells was increased 2.7-fold in the S100A9Tg mice compared to WT mice (p=2.75×10$^{-4}$), with no change in the total a-caspase-3/7$^+$ KLS population (FIG. 5g). Finally, to test if in vivo inflammasome inhibition improves hematopoiesis in S100A9Tg mice analogous to human MDS, aged S100A9Tg mice were treated with ICTA, an Icariin derivative that inhibits NLRP3 inflammasome activation (FIG. 13), every other day for eight weeks. ICTA treated transgenic mice showed marked improvement in peripheral blood counts, including increased hemoglobin, leukocyte count, red blood cells and platelet counts (FIG. 5h), indicating restored effective hematopoiesis. Thus, pyroptosis is the principal mechanism driving HSPC cell death and MDS in S100A9Tg mice.

Figure 6C:
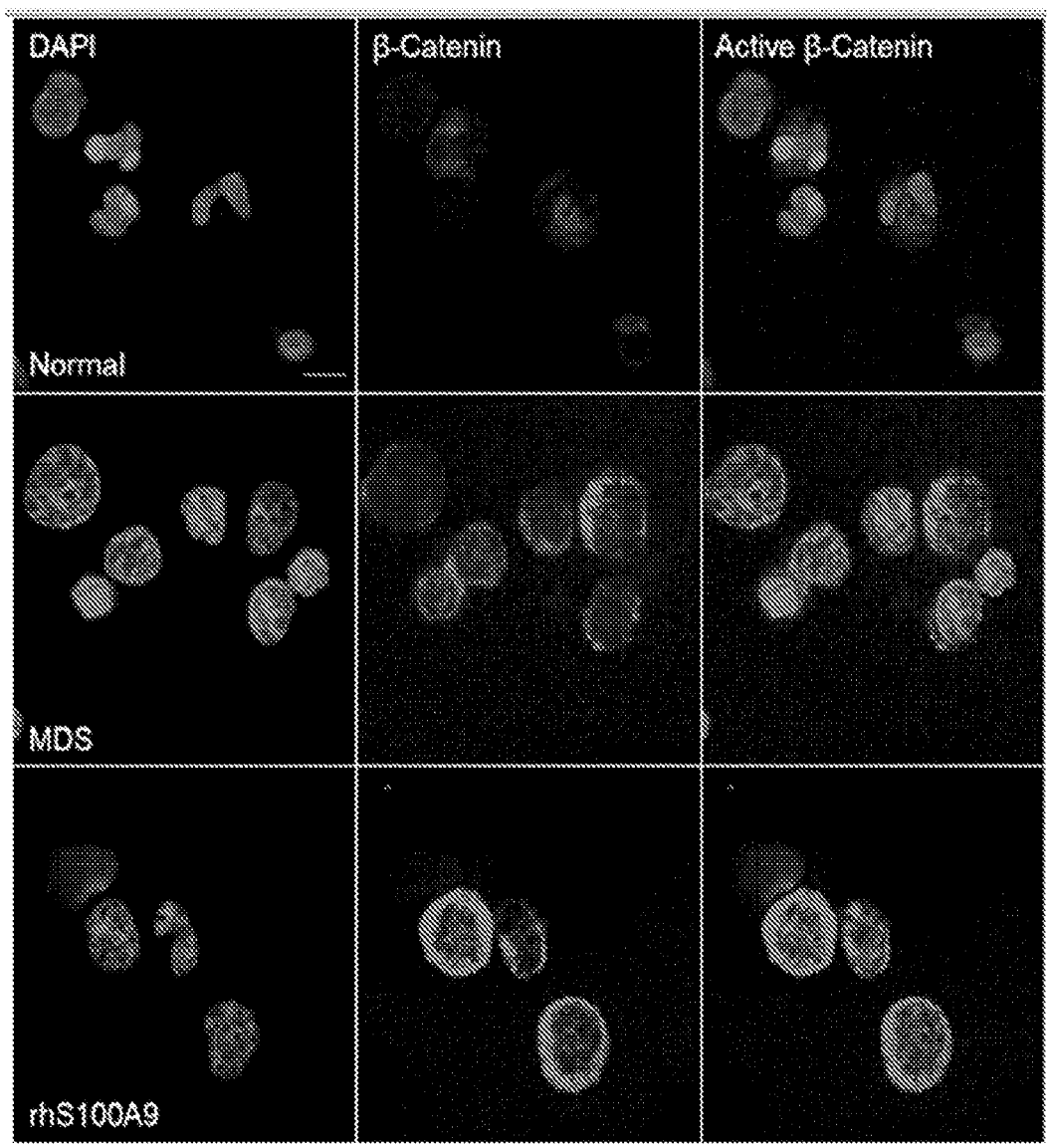
Figure 14A:
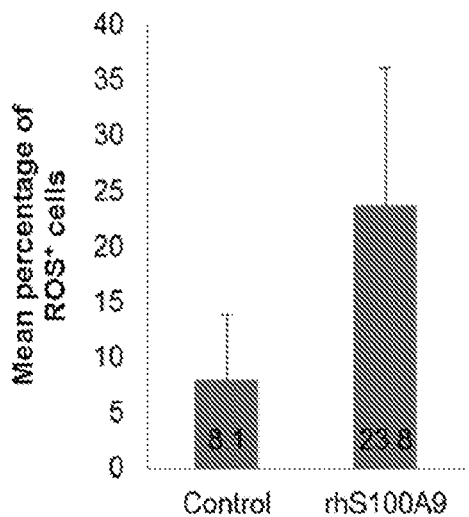
FIGS. 14A to 14D show recombinant human S100A9 is sufficient to induce ROS and β-catenin activation in monocytic cells. U937 cells were treated with 5 µg/mL rhS100A9 for 24 hours.
Figure 14B:
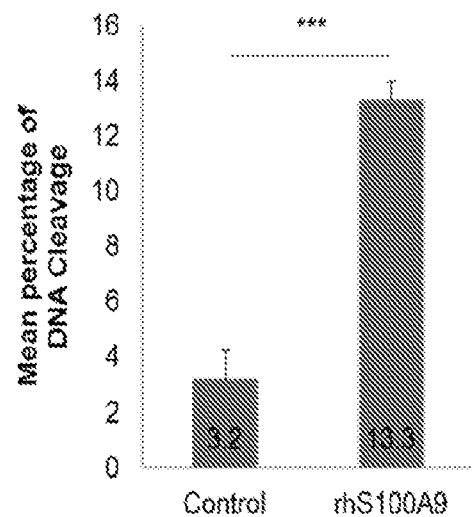
Figure 14C:
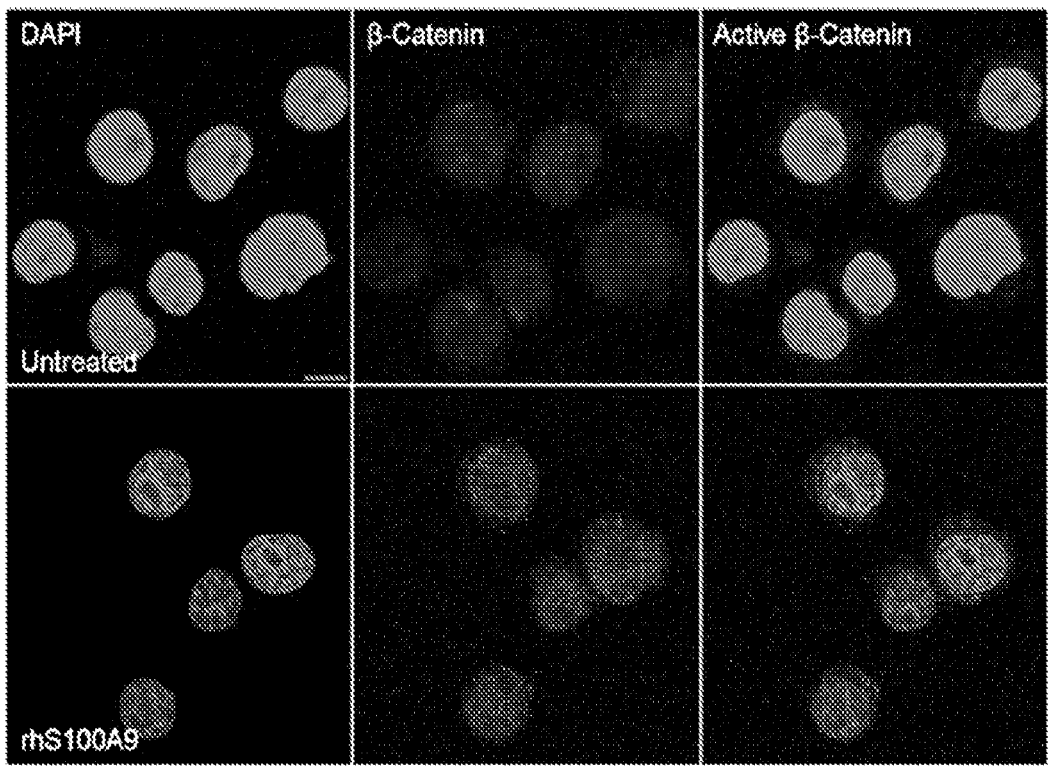
Figure 14D:
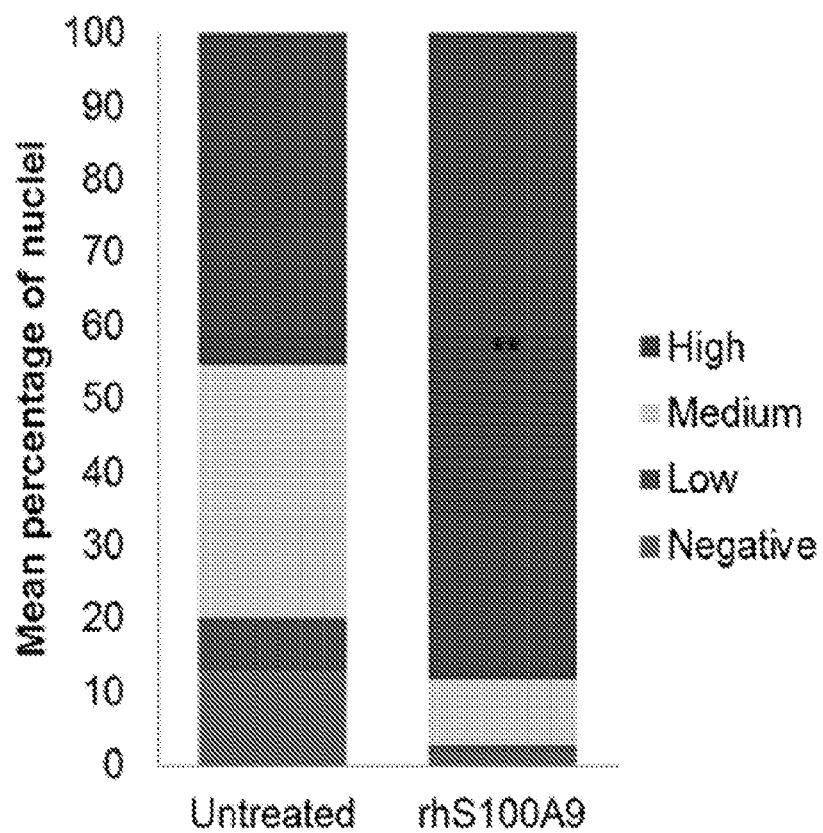

S100A9 and MDS Gene Mutations Trigger Pyroptosis and β-Catenin Activation Via ROS ROS act as DAMP intermediates that activate the Wnt/β-catenin axis (Rharass T, et al. J Biol Chem. 2014 289(40): 27937-51; Kajla S, et al. FASEB J. 2012 26(5):2049-59). Thus, ROS generated by either S100A9 or somatic gene mutations that are manifest in MDS may contribute to self-renewal and clonal expansion via activation of β-catenin. Monocytic U937 cells treated with 5 µg/mL rhS100A9 for 24 hours displayed a 2.9-fold increase in the mean percentage of ROS-positive cells and a 4.1-fold increase in DNA damage (p=1.5×10$^{-9}$), compared to untreated cells (FIG. 14a, 14b). Accordingly, mean percentage of ROS positive cells was increased in MDS BM-MNC (n=5) 16.5-fold compared to normal controls (n=2) (p=0.011) (FIG. 6a), with a corresponding significant increase in ROS MFI (p=0.028) (FIG. 6b). Further, confocal fluorescence microscopy analyses demonstrated marked increases in the levels of nuclear (activated) β-catenin in rhS100A9 treated U937 cells compared to untreated cells (p=2.4×10$^{-3}$) (FIG. 14c, 14d), and elevated levels of nuclear β-catenin were manifest in patient BM-MNC (n=6) compared to normal donors (n=3), as well as in normal BM-MNC treated with 5 µg/mL rhS100A9 for 24 hours compared to controls (p=0.043 and p=6.38×10$^{-7}$, respectively) (FIG. 6c, 6d). Finally, β-catenin gene expression was increased 9.5-fold in the BM cells of S100A9Tg mice versus WT BM cells, with corresponding up-regulation of Wnt/β-catenin target genes. Thus, S100A9-directed activation of β-catenin is a hallmark of MDS.

Figure 6G:
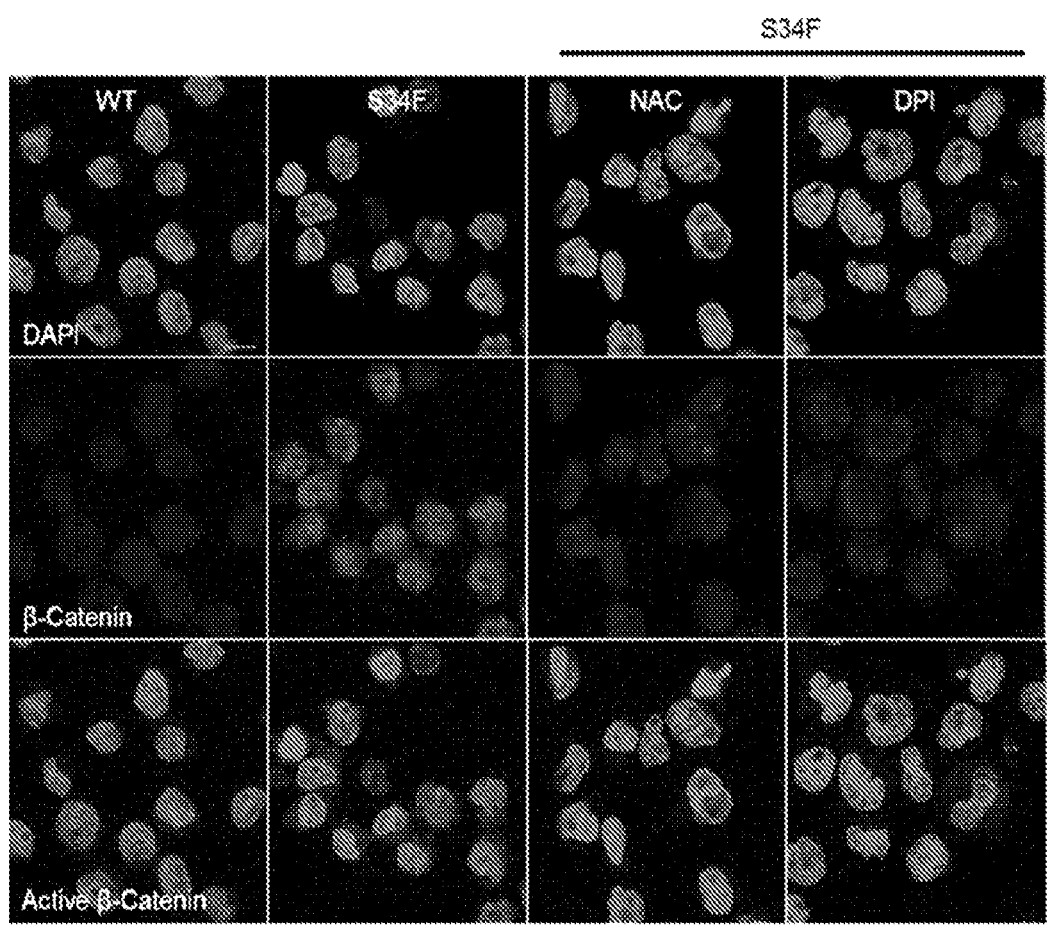
Figure 6H:
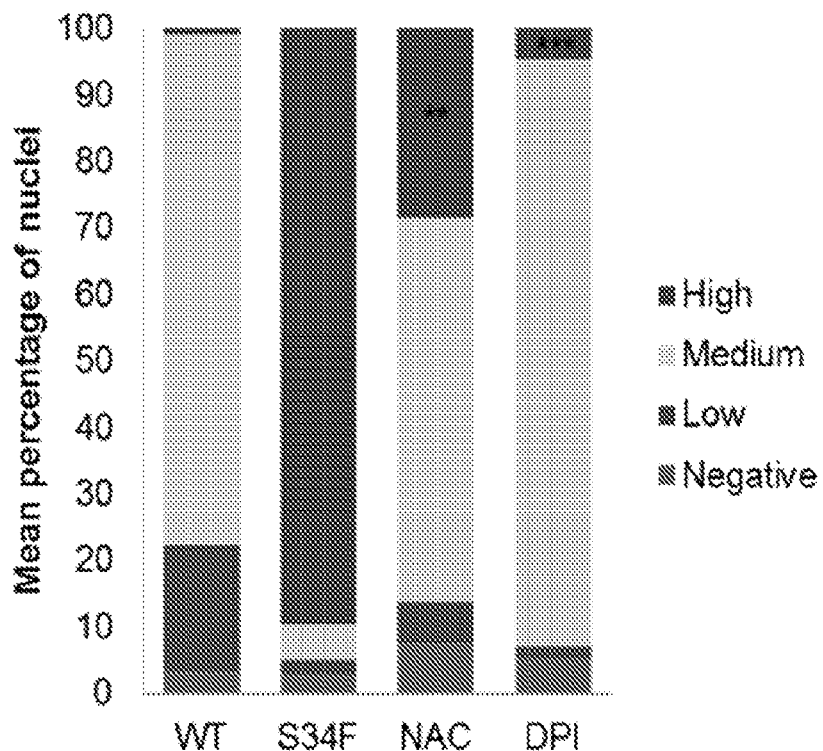
Figure 15A:
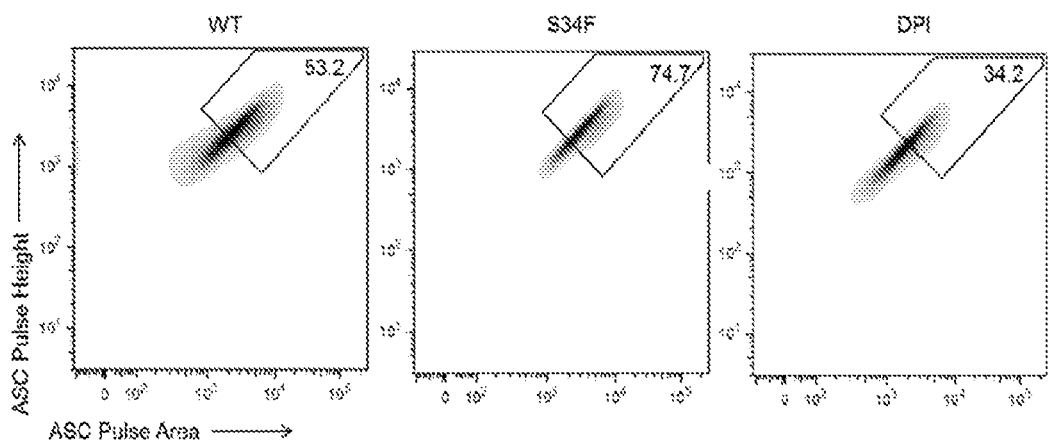
Figures 15H, 15I:
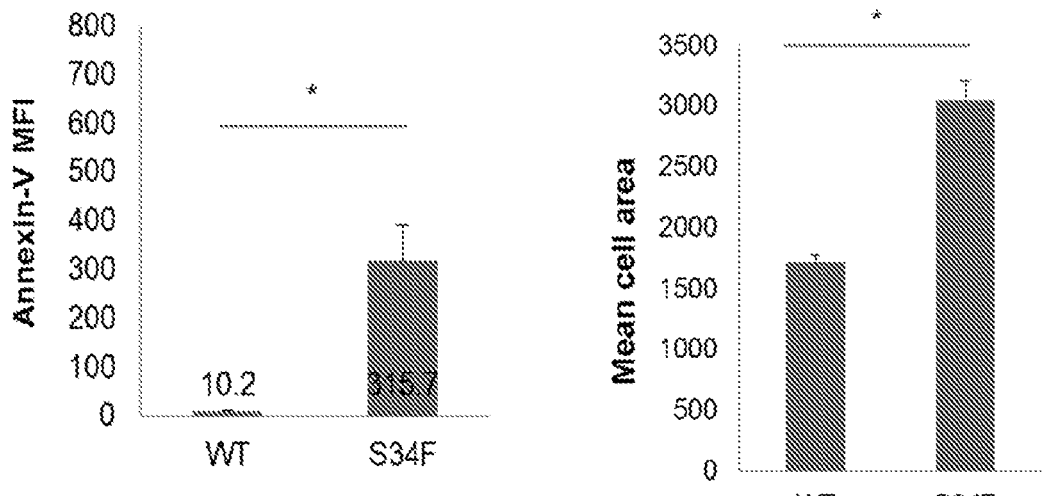
Figure 15J:
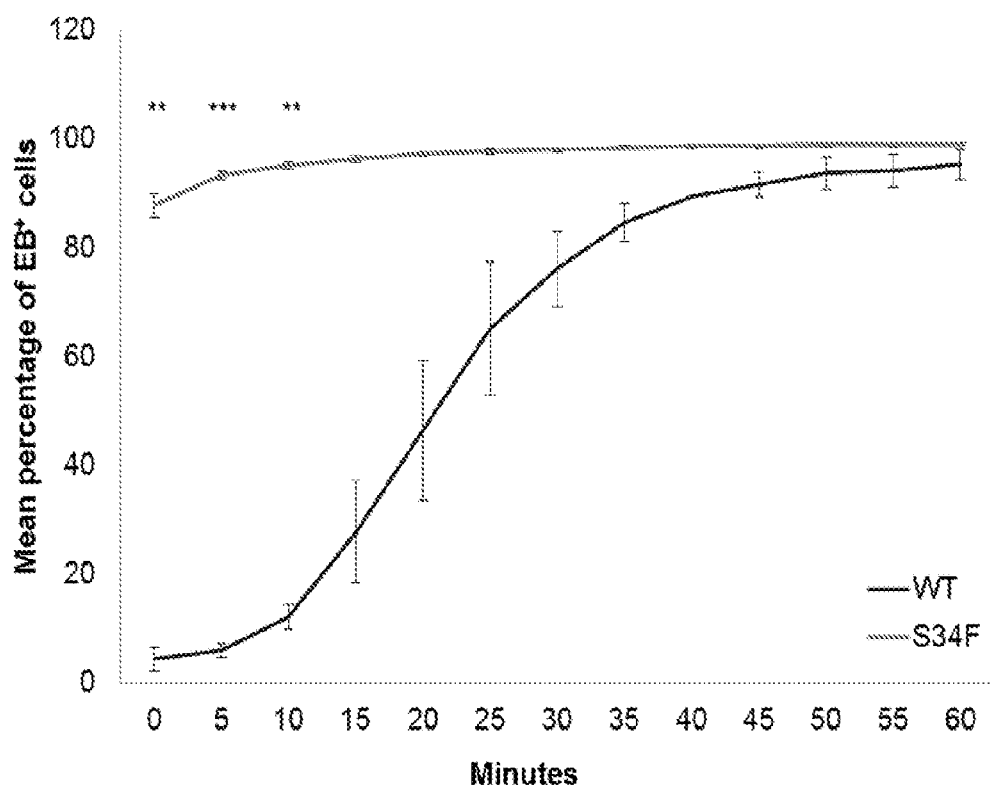

To test if somatic gene mutations manifest in MDS trigger pyroptosis and enhance self-renewal via activation of β-catenin, this circuit was first investigated in cells engineered to express MDS-associated mutants of the U2AF1 splicing factors (Yoshida K, et al. Nature. 2011 478(7367): 64-9). The percentage of pyroptotic cells was increased 4.6-fold in S34F U2AF1 mutant-versus WT U2AF1-expressing cells, accompanied by increased levels of a-caspase-1 (p=0.044) and annexin-V (p=0.021) (FIG. 15a-15h). U2AF1-S34F-expressing cells also displayed significant increases in mean cell area (p=0.035) and ethidium bromide influx (FIG. 15i, 15j), the mean percentage of ROS$^+$ cells (p=1.5×10$^{-3}$), ROS MFI (p=0.032) (FIG. 6e, 6f) and nuclear localization of β-catenin (FIG. 6g, 6h). Notably, treatment of U2AF1-S34F mutant cells with the anti-oxidant N-acetylcysteine (NAC) or the NADPH oxidase (NOX) inhibitor DPI effectively reduced β-catenin activation in mutant cells (p=3.8×10$^{-3}$ and p=2.5×10$^{-6}$, respectively) (FIG. 6g, 6h).

Figure 16A:
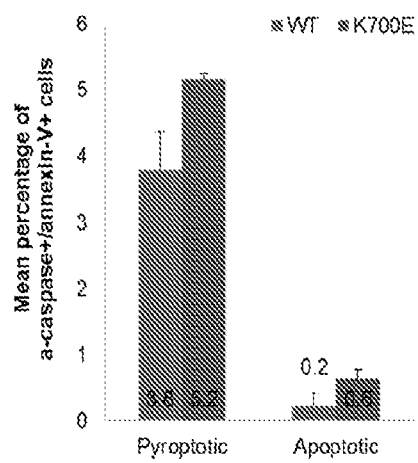
FIGS. 16A to 16G shows SF3B1 K700E induces pyroptosis. The ability of the SF3B1 K700E conditional knock-in mutation to induce pyroptosis was assessed in BM cells harvested from WT (n=3) and mutant (n=3) mice.
Figure 16B:
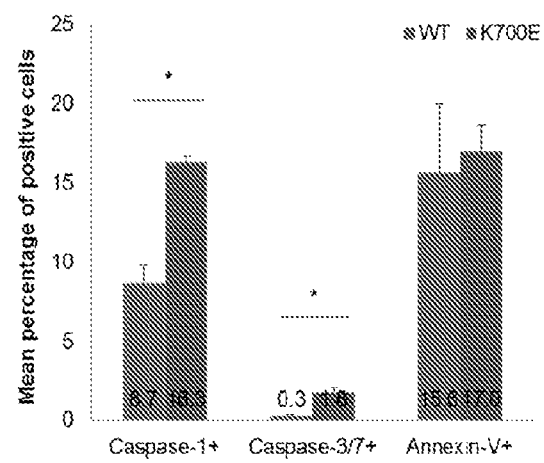
Figure 16C:
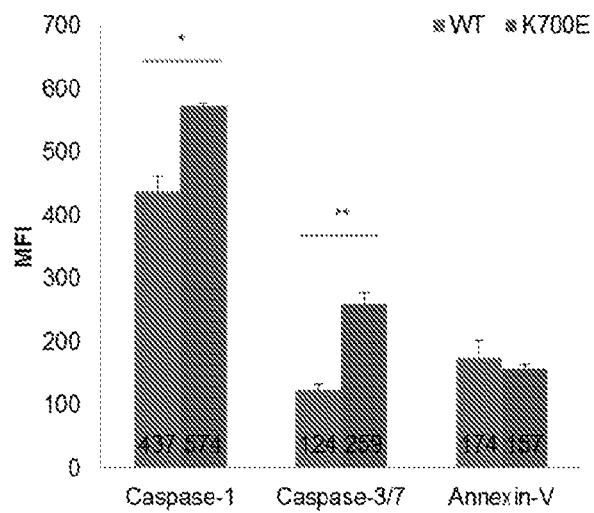
Figure 16D:
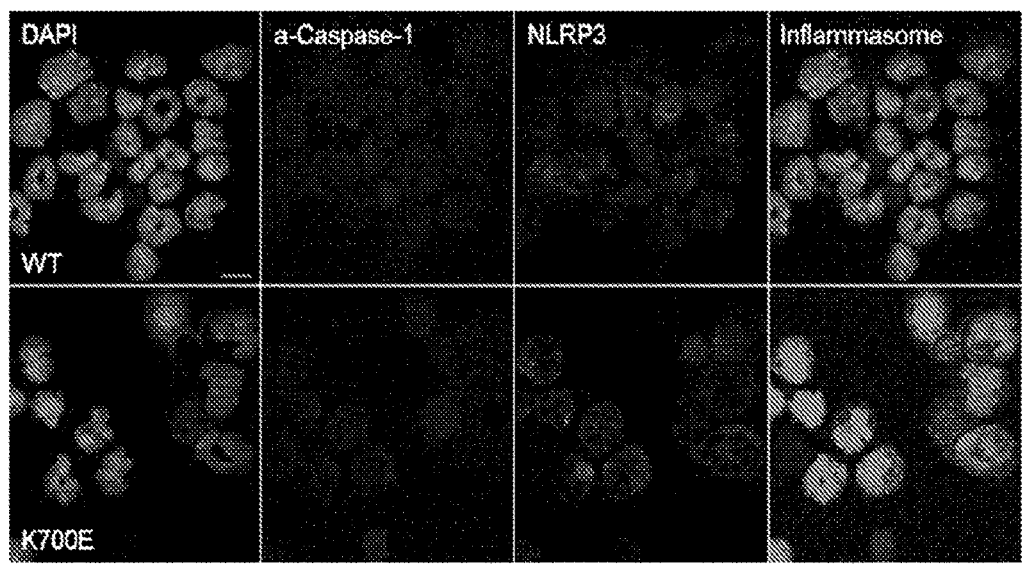
Figure 16E:
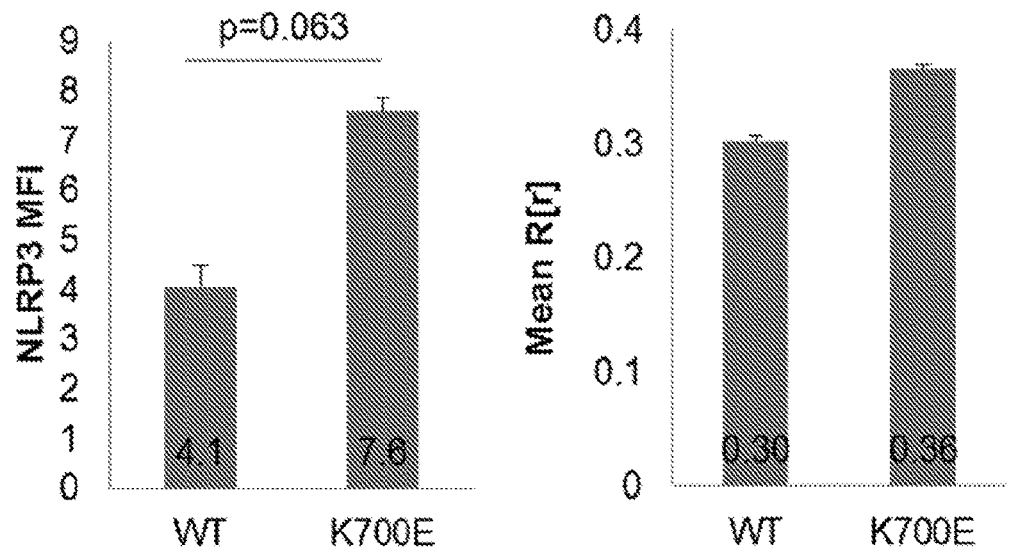
Figure 16F:
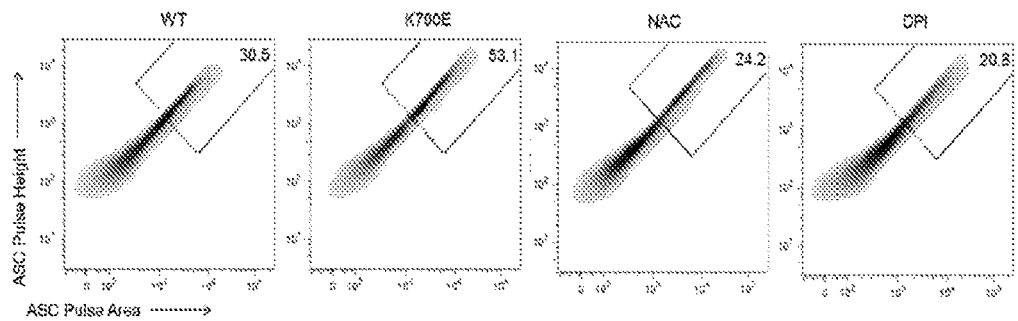
Figure 16G:
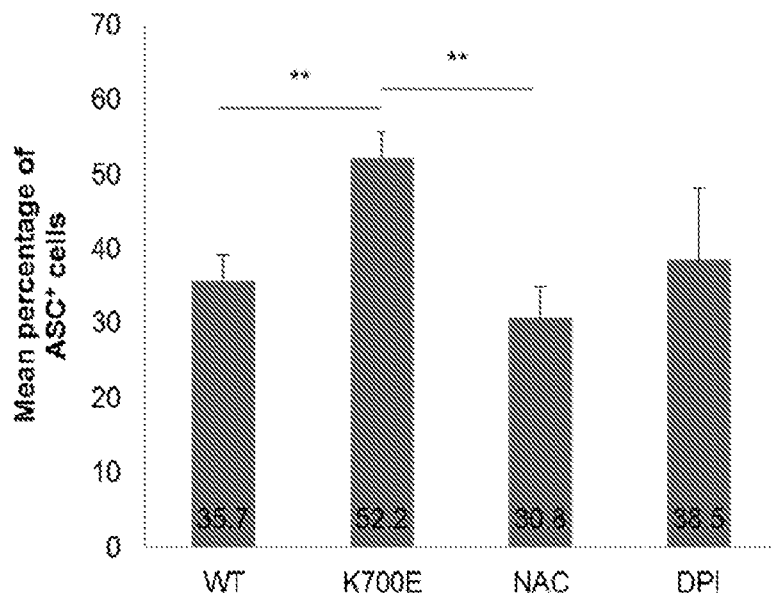
Figure 17A:
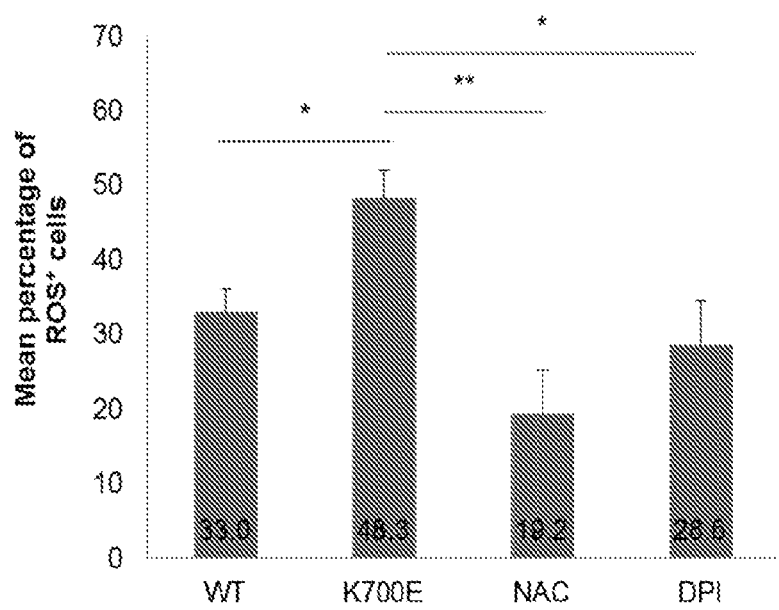
FIGS. 17A to 17D show SF3B1 K700E supports self-renewal through β-catenin activation. The ability of the SF3B1 K700E conditional knock-in mutation to support self-renewal through activation of β-catenin was assessed in BM cells harvested from WT (n=6) and mutant (n=6) mice.
Figure 17B:
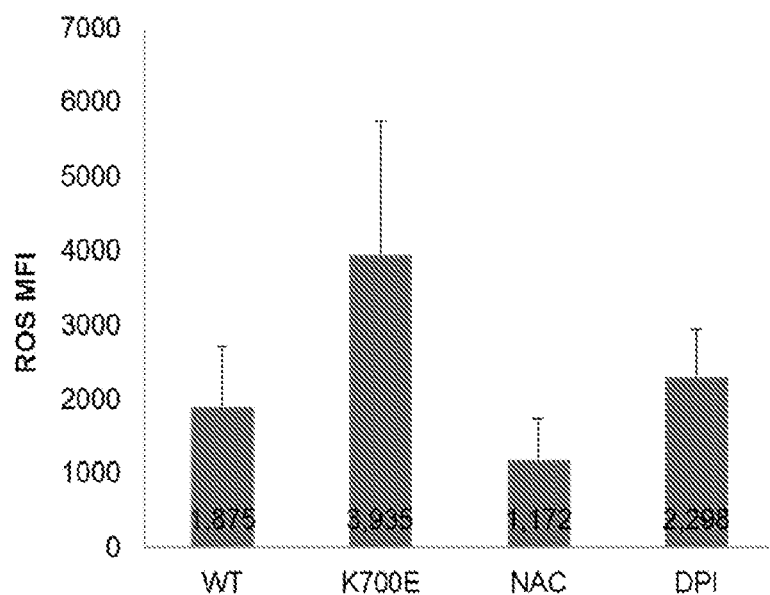
Figure 17C:
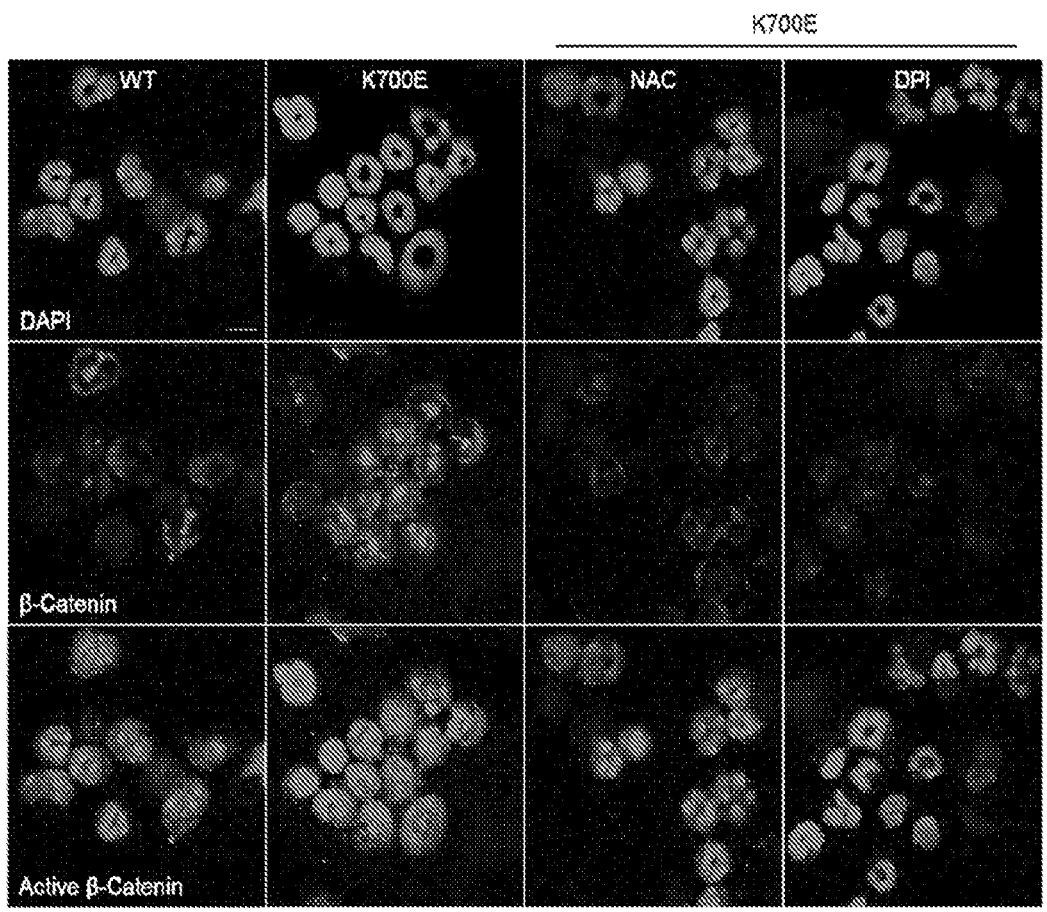
Figure 17D:
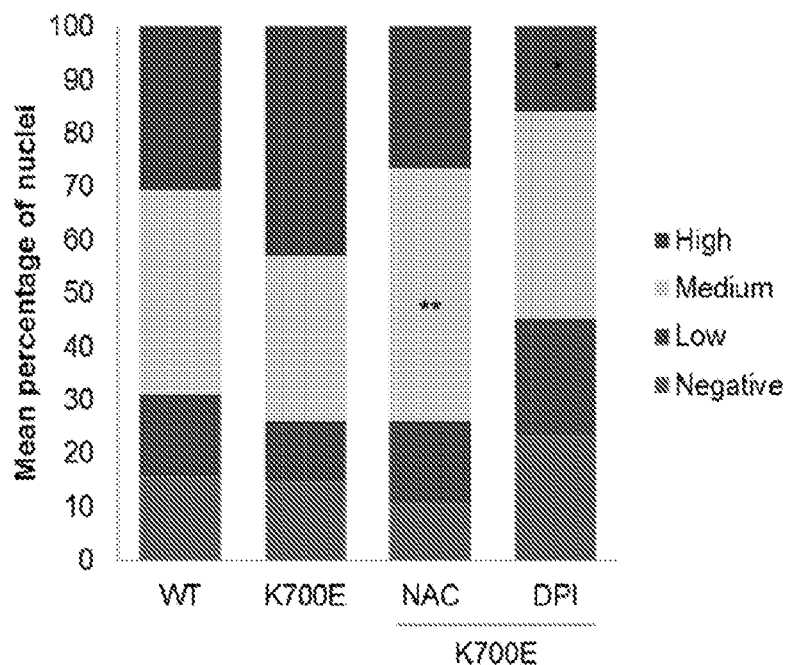
Figure 18A:
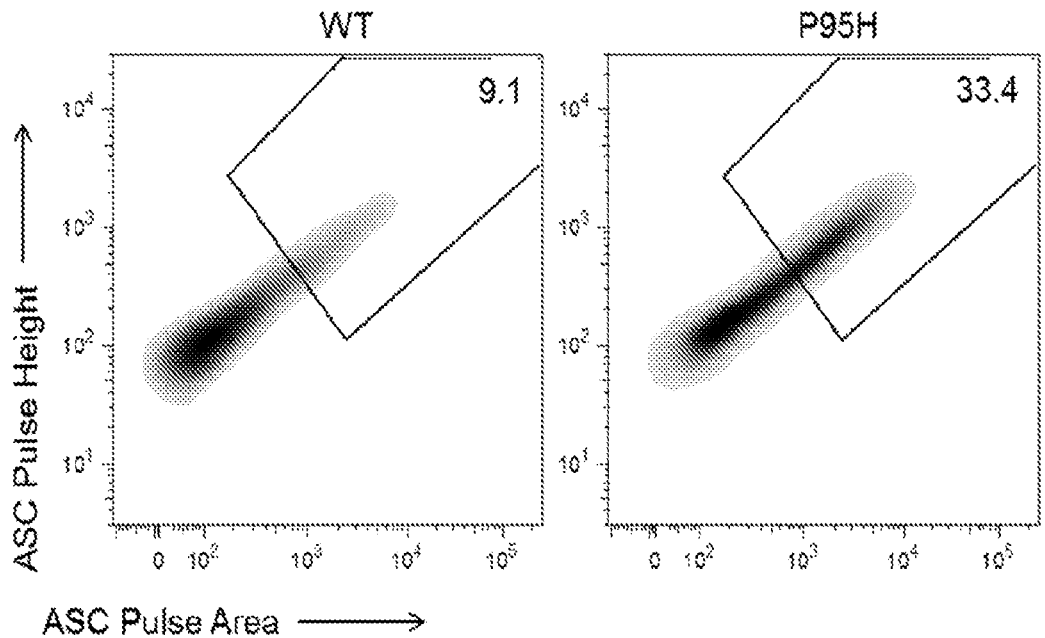
FIGS. 18A to 18K show SRSF2 mutants induce pyroptosis and support self-renewal through β-catenin. HEK293T cells were transiently transfected with WT and P95H mutant SRSF2. Data are representative of three independent experiments, and of the GFP$^+$ transfected population.
Figure 18B:
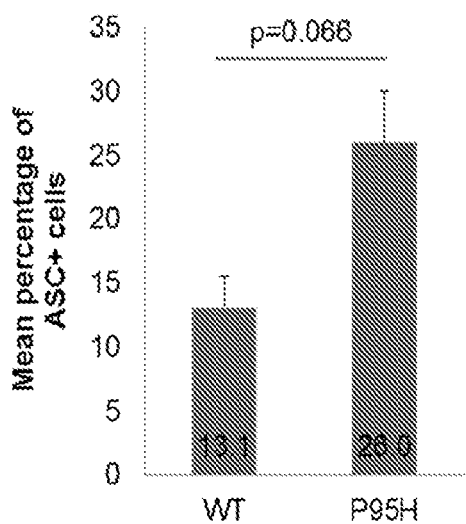
Figure 18C:
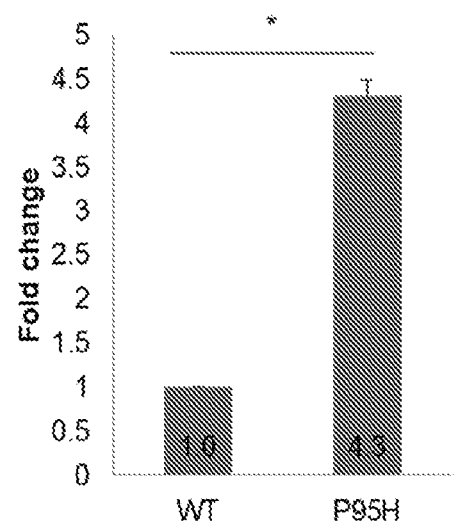
Figure 18D:
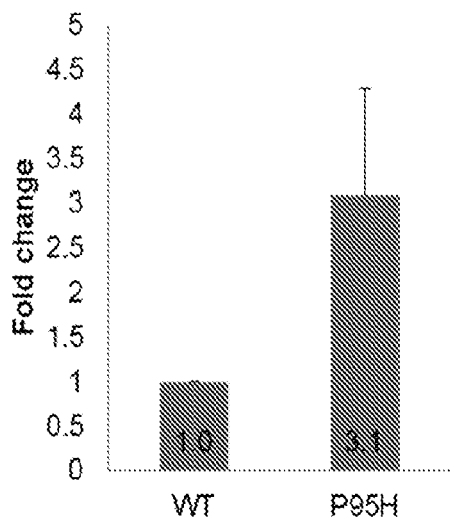
Figure 18E:
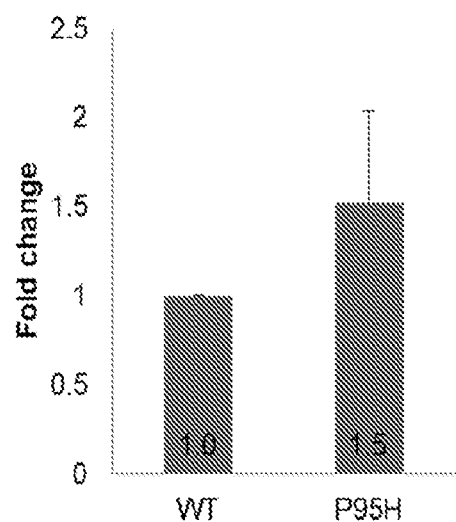
Figure 18F:
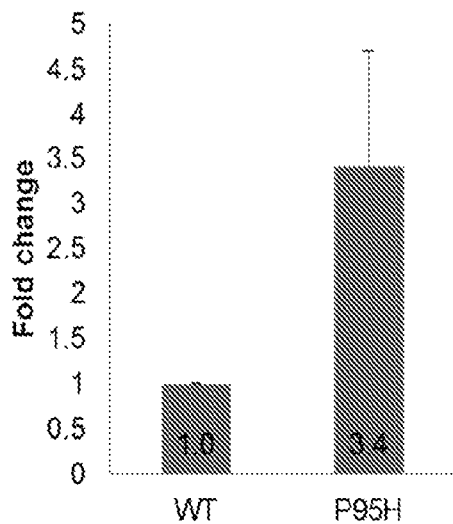
Figure 18G:
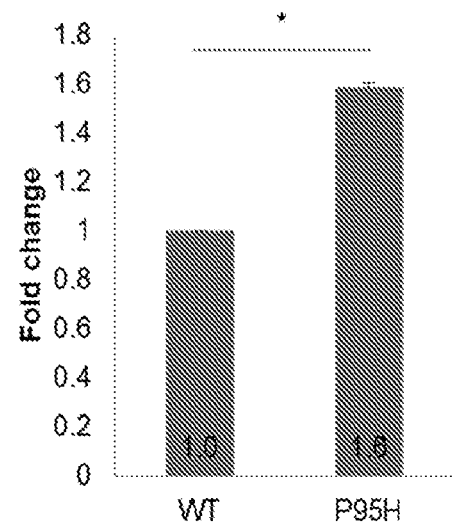
Figure 18H:
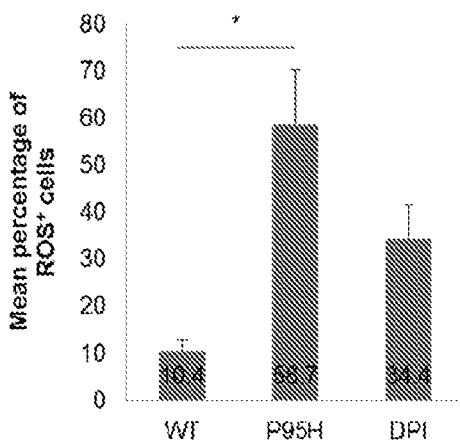
Figure 18I:
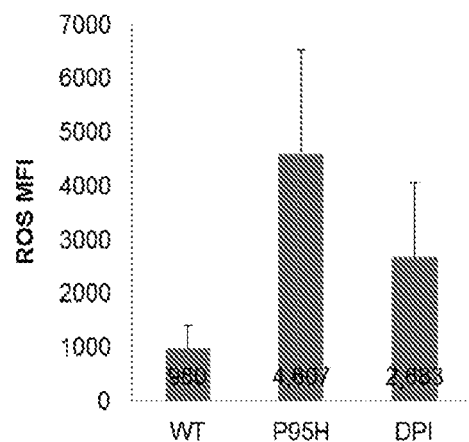
Figure 18J:
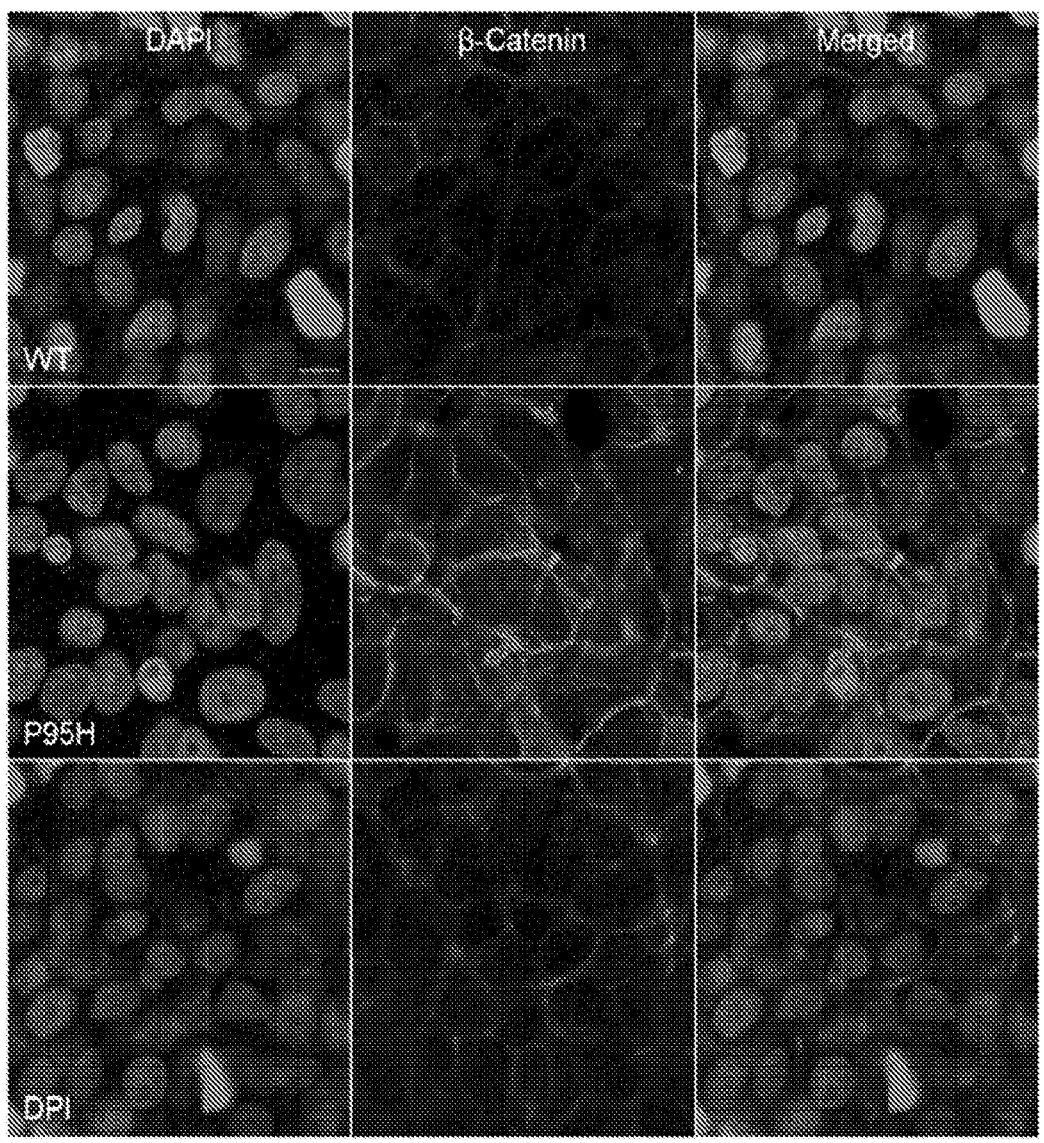
Figure 18K:
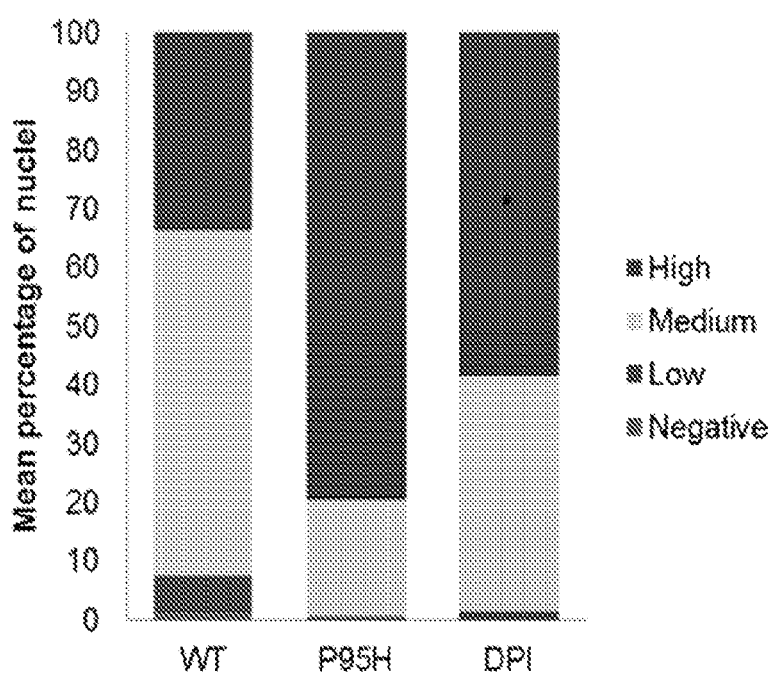
Figure 19A:
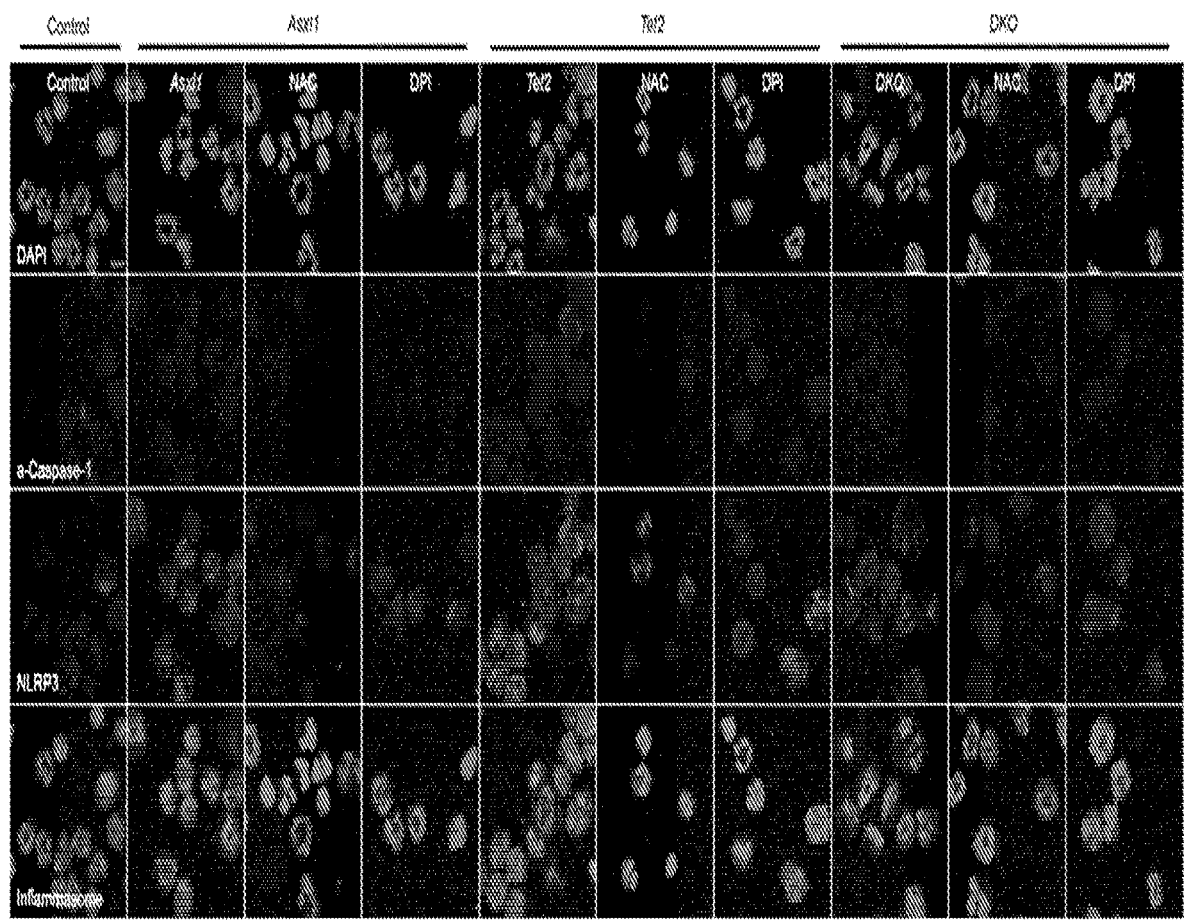
FIGS. 19A to 19H show Asxl1 and Tet2 deletions are sufficient to induce pyroptosis. The ability of deletions in Asxl1 and Tet2 to induce pyroptosis was assessed in BM cells isolated from Asxl1 KO, Tet2 KO, and DKO cells, compared to control cells.
Figure 19B:
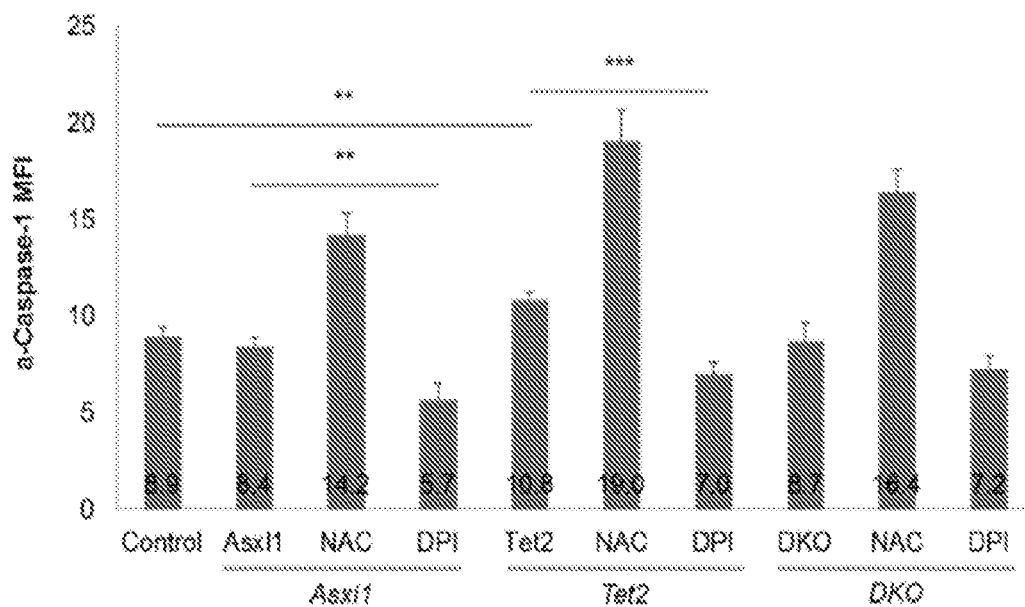
Figure 19C:
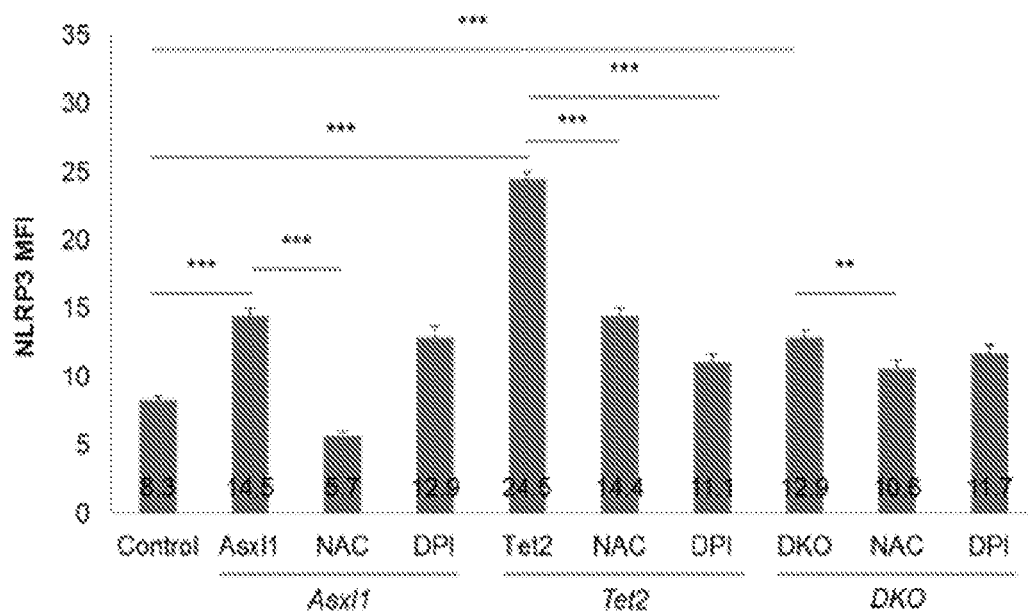
Figure 19D:
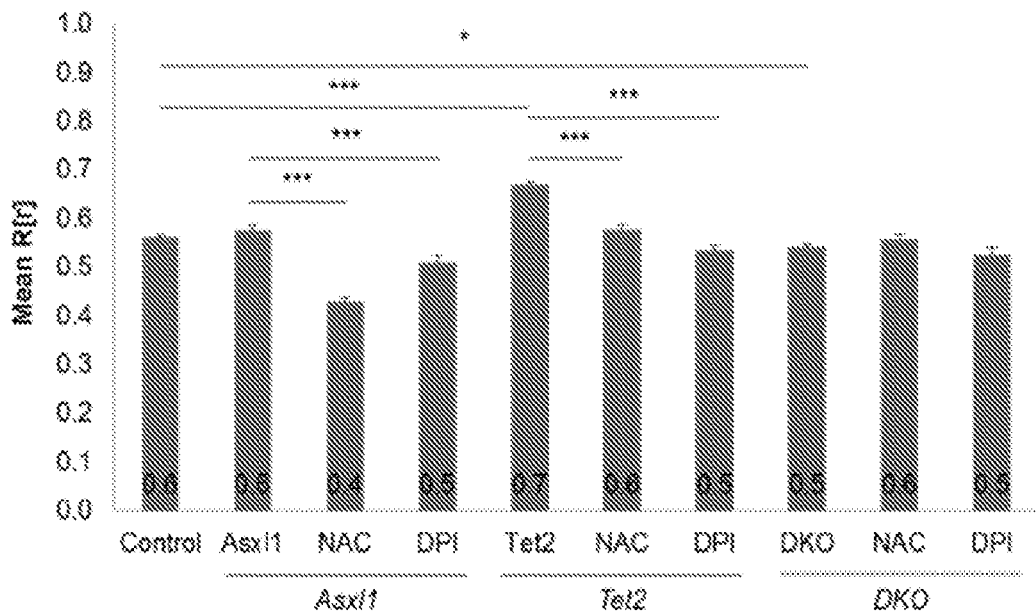
Figure 19E:
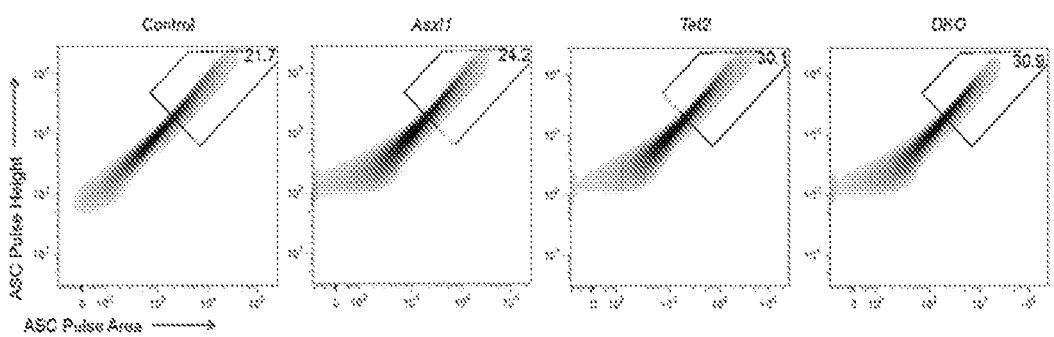
Figure 19F:
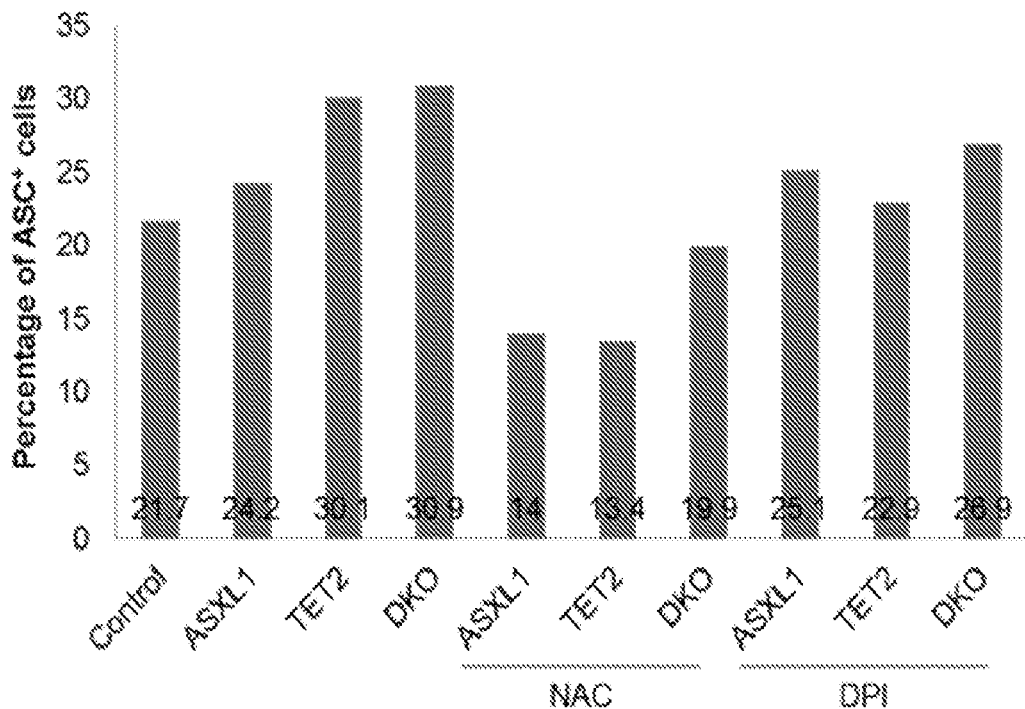
Figure 19G:
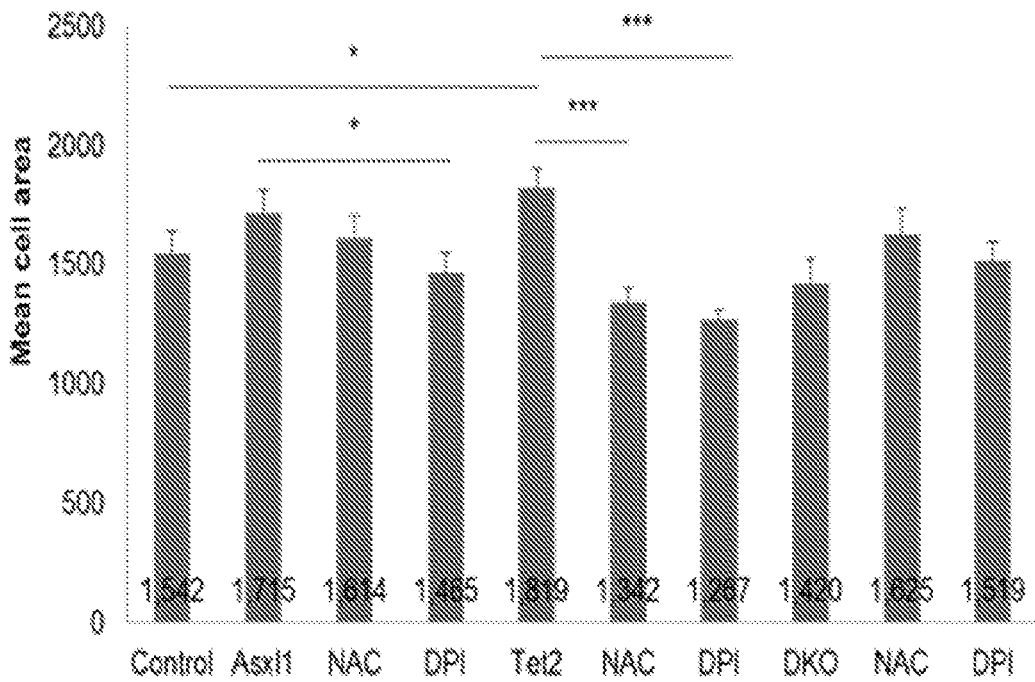
Figure 19H:
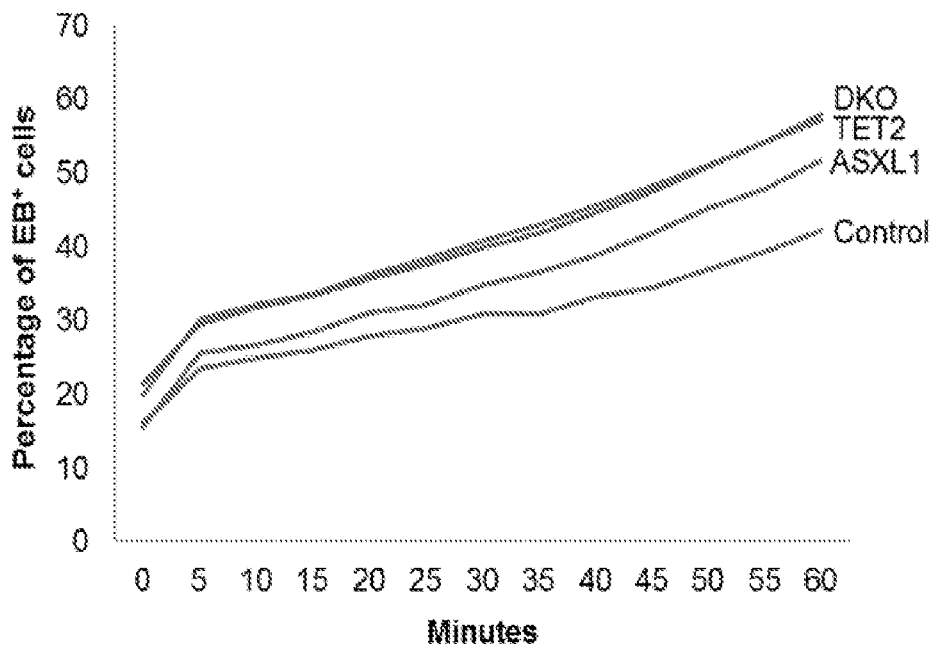
Figure 20A:
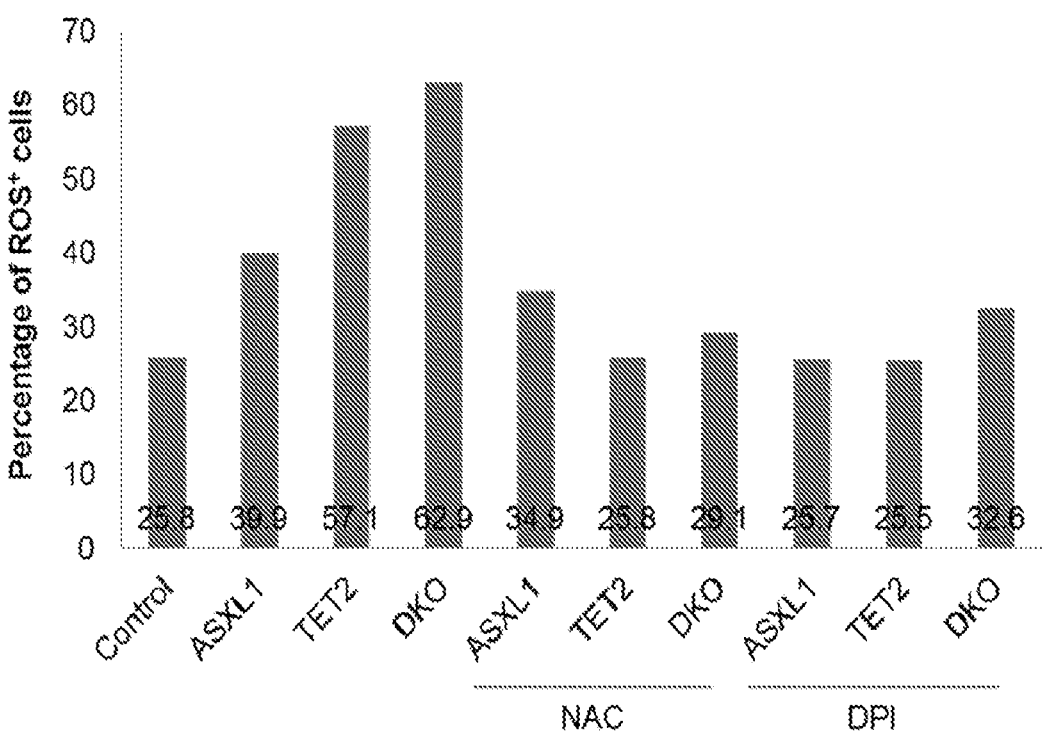
FIGS. 20A to 20D show Asxl1 and Tet2 deletions are sufficient to drive self-renewal through β-catenin activation. The ability of deletions in Asxl1 and Tet2 to activate β-catenin was assessed in BM cells isolated from Asxl1 KO, Tet2 KO, and DKO cells, compared to control cells.
Figure 20B:
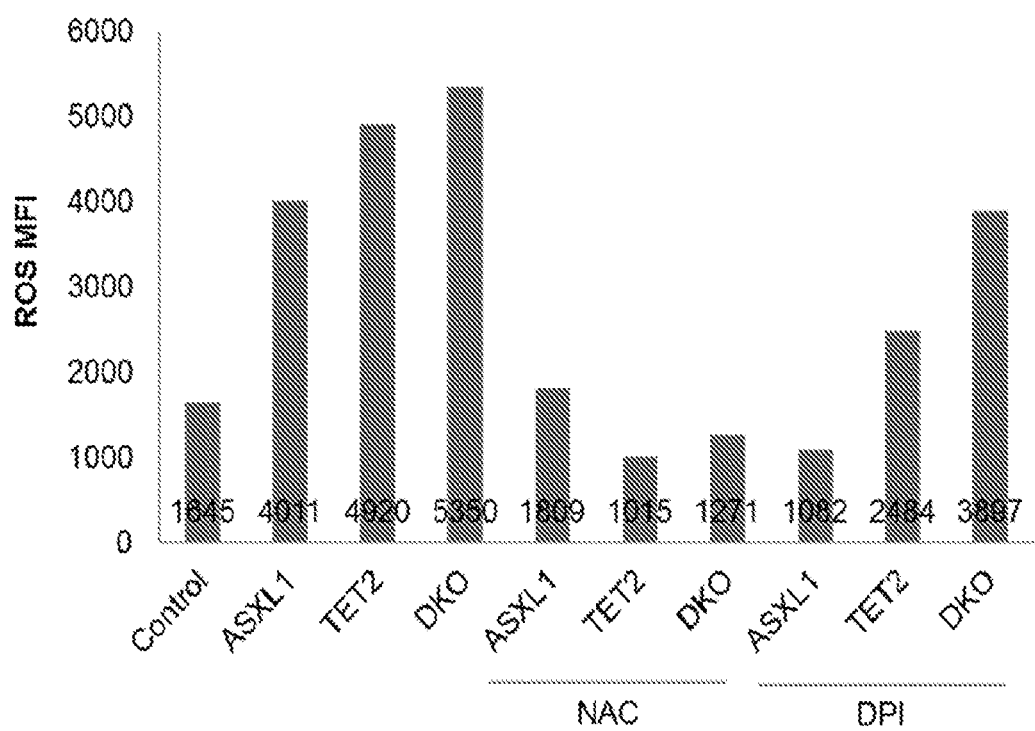
Figure 20C:
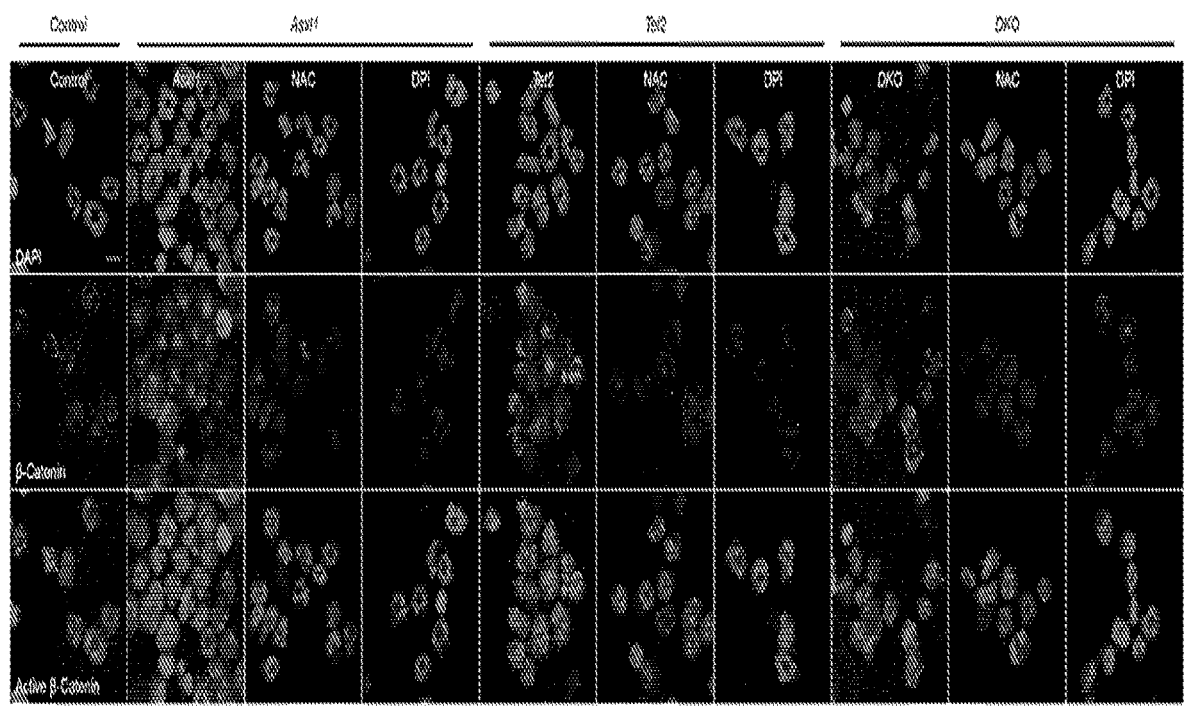
Figure 20D:
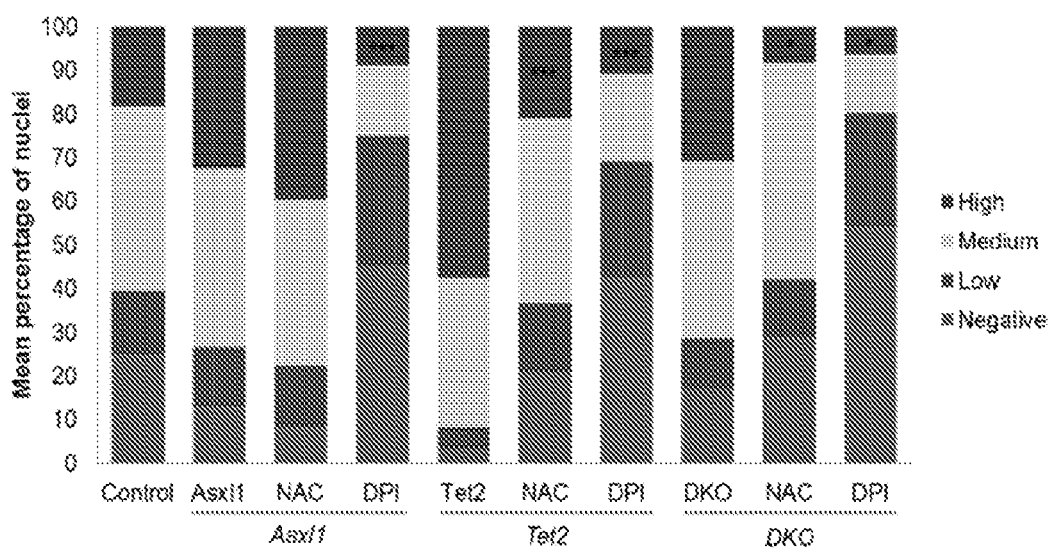

BM cells harvested from SF3B1-K700E conditional knock-in mice (n=3), which also display a MDS phenotype (Obeng E. A, et al. Blood. 2014 124(6):828-30), displayed similar increases in the percentage of pyroptotic versus apoptotic cells, with significant increases in total a-caspase-1$^+$ cells (p=0.014) versus WT controls (n=3) (FIG. 16a, 16b). Further, MFI of a-caspase-1 and a-caspase-3 were both significantly increased in the SF3B1-K700E mutant BM cells (p=0.030 and p=6.92×10$^{-3}$, respectively) (FIG. 16c), which displayed inflammasome assembly (FIG. 16d). Accordingly, NLRP3 protein expression was increased 1.9-fold in the SF3B1-K700E cells (p=0.063), as NLRP3 inflammasome formation was increased 1.2-fold (FIG. 16e). Inflammasome formation was also assessed by flow cytometry based on the detection of the inflammasome adaptor protein ASC oligomerization, whose incorporation into inflammasome complexes can be detected by changes in fluorescence pulse height and area (Sester D. P, et al. J Immunol. 2015 194(1):455-62). SF3B1-K700E mutant-expressing BM cells (n=6) had marked increases in inflammasome formation versus WT controls (n=6, p=8.4×10−3), which was significantly reduced upon treatment with NAC (n=6, p=2.68×10$^{-3}$) or DPI (n=3) (FIG. 16f, 16g). Moreover, mean percentage of ROS$^+$ cells and ROS MFI were both markedly increased in SF3B1-K700E-expressing mutant BM cells, which was extinguished below the level of WT controls by NAC or DPI treatment (FIG. 17a, 17b). Finally, SF3B1-K700E mutant-expressing BM cells demonstrated a statistically significant increase in the percentage of cells with elevated levels of nuclear β-catenin compared to WT controls (p=0.40), which was significantly reduced upon treatment with NAC (p=2.0×10$^{-3}$) or DPI (p=1.8×10$^{-2}$) (FIG. 17c, 17d). Similar findings were observed in mutant versus WT SRSF2-expressing HEK293T cells (FIG. 18), as well as with epigenetic regulatory gene mutations (ASXL1, TET2) (FIG. 19, 20). Thus, MDS somatic gene mutations prime cells to undergo pyroptosis, which promotes self-renewal and contributes to an inflammatory microenvironment that is driven by ROS.

Discussion

Heretofore ineffective hematopoiesis in MDS has been attributed to high fractions of proliferating BM progenitors with a propensity to undergo apoptotic cell death within an unexplained inflammatory microenvironment (Span L. F, et al. Leuk Res. 2007 31(12):1659-67; Raza A, et al. Blood. 1995 86(1):268-76). Nearly two decades ago it was reported that MDS HSPC generate IL-1β in short term cultures, which directly correlated with the extent of apoptosis as measured by DNA fragmentation (Mundle S. D, et al. Blood. 1996 88(7):2640-7). Evidence is disclosed that these and other biological features of MDS are explained by the activation of the NLRP3 pattern recognition receptor by S100A9 and by ROS DAMP intermediates that induce inflammasome assembly, β-catenin nuclear translocation and pyroptotic cell death. Notably, pyroptotic-associated gene transcripts and inflammasome assembly are profoundly up-regulated in MDS independent of genotype. Moreover, pyroptotic but not apoptotic cells are markedly increased in MDS stem cells, progenitors, and erythroid precursors.

Accordingly, knockdown of caspase-1, but not caspase-3, in MDS BM-MNC, significantly reduced the pyroptotic cell fraction. Similarly, neutralization of S100A9 in MDS BM plasma, or pharmacologic inhibition of inflammasome assembly, suppressed pyroptosis and restored effective hematopoiesis in vitro and in a murine MDS model. Thus, pyroptosis, a caspase-1-dependent inflammatory cell death, impairs HSPC survival in MDS.

S100A8/S100A9 activate both NF-κB and NLRP3 inflammasome assembly via an NADPH oxidase (NOX)/ROS-dependent mechanism (Simard J. C, et al. PLoS One. 2013 8(8):e721381; Liao P. C, et al. Inflamm Res. 2013 62(1):89-96; Heid M. E, et al. J Immunol. 2013 191(10): 5230-8; Bauernfeind F, et al. J Immunol. 2011 187(2):613-7). S100A8/9 heterodimers serve as a scaffold for the membrane assembly and activation of the NOX complex (Doussiere J, et al. Eur J Biochem. 2002 269(13):3246-55; Kerkhoff C, et al. FASEB J. 2005 19(3):467-9), which generates ROS via transfer of electrons across membranes to generate superoxide (Bedard K, et al. Physiol Rev. 2007 87(1):245-313). NOX activity regulates both priming and activation of NLRP3 inflammasomes, as NOX inhibition suppresses the activation of caspase-1 and IL-1β secretion (Liao P. C, et al. Inflamm Res. 2013 62(1):89-96). Moreover, transcription and nuclear localization of β-catenin are redox- and NOX-dependent (Coant N, et al. Mol Cell Biol. 2010 30(11):2636-50; Wu X, et al. Cell. 2008 133(2):340-53). Although MDSC are a key paracrine source of S100A9 in the MDS BM-microenvironment (Chen X, et al. J Clin Invest. 2013 123(11):4595-611), here it shown that MDS HSPC also express high intracellular levels of S100A9 (FIG. 11), suggesting that inflammasome activation may be sustained by intracrine DAMP stimulation, and upon cell lysis, promote BM expansion of MDSC. Importantly, NOX inhibition suppressed inflammasome and β-catenin activation in both patient-derived BM-MNC and cells harboring varied classes and types of MDS founder gene mutations. Thus, S100A9 induces NOX activity to drive ROS-dependent inflammasome assembly and pyroptosis, accompanied by β-catenin nuclear translocation.

A hallmark of MDS BM precursors is their enlarged cell size or macrocytosis. It is shown that activation of pattern recognition receptors triggers expansion in size of MDS progenitors via influx of cations mediated by the transient receptor potential melastatin 2 (TRMP2) cation channel, a plasma membrane calcium-permeable channel in hematopoietic cells (Zhang W, et al. Am J Physiol Cell Physiol. 2006 290(4):C1146-59). Further, TRPM2 channels are activated by NOX-derived ROS via oxidation of a single channel methionine residue, Met-214, which is indispensable for NLRP3 inflammasome activation (Kashio M, et al. Proc Natl Acad Sci USA. 2012 109(17):6745-50; Zhong Z, et al. Nat Commun. 2013 4:1611; Yamamoto S, et al. Nat Med. 2008 14(7):738-47). Activation of TRPM2 then directs calcium influx that then leads to corresponding increases in cell volume (Kuhn F, et al. Pflugers Arch. 2005 451(1):212-9). The disclosed data show that MDS BM-MNC display increased influx of the TRPM2 channel substrate ethidium bromide, confirming inflammasome-initiated pore formation. Additionally, quantifying BM cell size according to lineage and stage of maturation confirmed the larger size of MDS BM precursors versus normal controls. The disclosed findings indicate that S100A9-mediated NOX activation and subsequent inflammasome initiated pyroptosis explain the characteristic larger cell size, proliferation and inflammatory cell death manifest in MDS.

NOX-derived ROS enhance mitogenic response to receptor-tyrosine kinases through oxidative inactivation of protein tyrosine phosphatases (Block K & Gorin Y. Nat Rev Cancer. 2012 12(9):627-37). Somatic gene mutations found in MDS are known to trigger Rac/NOX-dependent ROS generation (Sallmyr A, et al. Cancer Lett. 2008 270(1):1-9; Rassool F, et al. Cancer Res. 2007 67(18):8762-71). As ROS serve as DAMP intermediates that activate both inflammasomes and β-catenin, ROS generated by either S100A9 or MDS somatic gene mutations may drive pyroptosis, self-renewal and propagation of the MDS clone. Mechanistically, NOX-derived ROS stabilizes and activates β-catenin by oxidation and dissociation of nucleoredoxin (NRX) from disheveled (Dvl), which in turn inactivates the β-catenin destruction complex (Funato Y, et al. Nat Cell Biol. 2006 8(5):501-8). It is shown herein that ROS and nuclear β-catenin localization are profoundly increased in MDS HSPC. Further, S100A9 treatment of normal BM-MNC is sufficient to trigger nuclear translocation of β-catenin that is abolished by the anti-oxidant NAC or NADPH-oxidase inhibition. Similarly, BM-MNC from S100A9-Tg mice displayed marked increases in the expression and nuclear localization of β-catenin, with corresponding up-regulation of β-catenin target genes (data not shown). Of particular importance, varied RNA splicing gene mutations (U2AF1, SF3B1, SRSF2) and epigenetic regulatory gene mutations (ASXL1, TET2) found in MDS triggered pyroptosis, pore formation, cell volume expansion and β-catenin activation, which was extinguished by treatment with NAC or NOX-inhibition. Thus, both S100A9-induced NOX activation and MDS gene mutations initiate pyroptosis through superoxide generation to drive β-catenin activation and afford a proliferative advantage to the MDS clone. Accordingly, these findings explain how such diverse somatic gene mutations give rise to an MDS phenotype.

Figure 21:
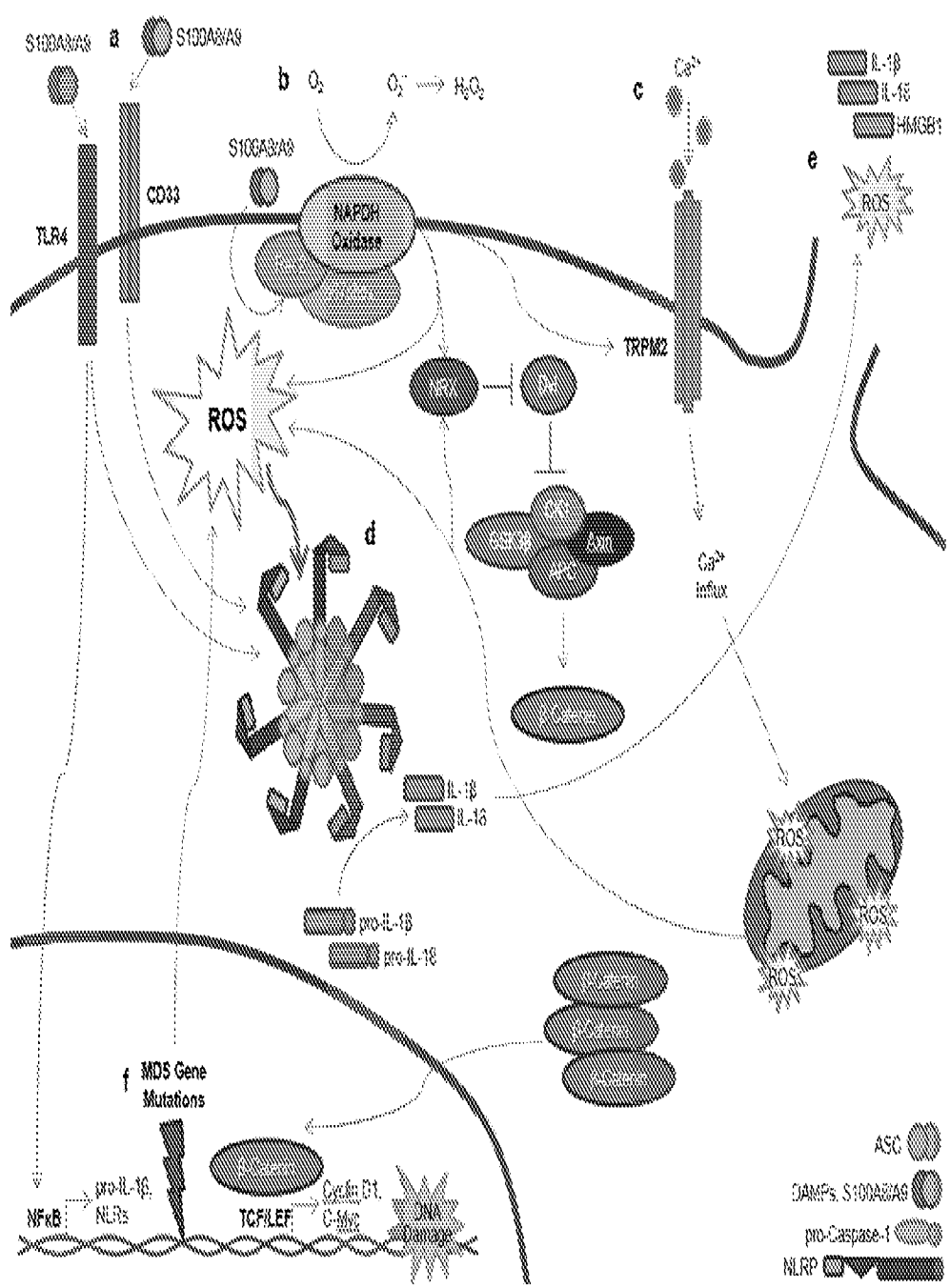
FIGS. 21A to 21F show a S100A9-pyroptosis circuit provokes phenotypes manifest in MDS.

In conclusion, despite genetic heterogeneity, inflammasome activation underlies the biological phenotype in MDS, whereby DAMP signals and MDS gene mutations license a common redox-sensitive inflammasome platform to drive pyroptotic death, elaborate inflammatory cytokines, activate cation influx, and support propagation of the MDS clone through β-catenin activation (FIG. 21). These findings provide a common platform that accounts for the biological features of MDS and suggest that strategies targeting S100A9 neutralization or inhibition of pyroptosis signaling offer therapeutic promise in MDS.

Example 2: Relationship Between Serum S100A9 Concentration & Serum EPO

Anemia remains the most frequent cytopenia in lower-risk MDS. Epoetin α, epoetin β, and darbepoetin (DAR) have been used for several years, alone or in combination with G-CSF, to treat anemia of MDS. Serum EPO level is inversely predictive for erythropoiesis-stimulating agent (ESA) response (Park S, et al. Blood. 2008 Jan. 15; 111(2): 574-82).

Figure 22:
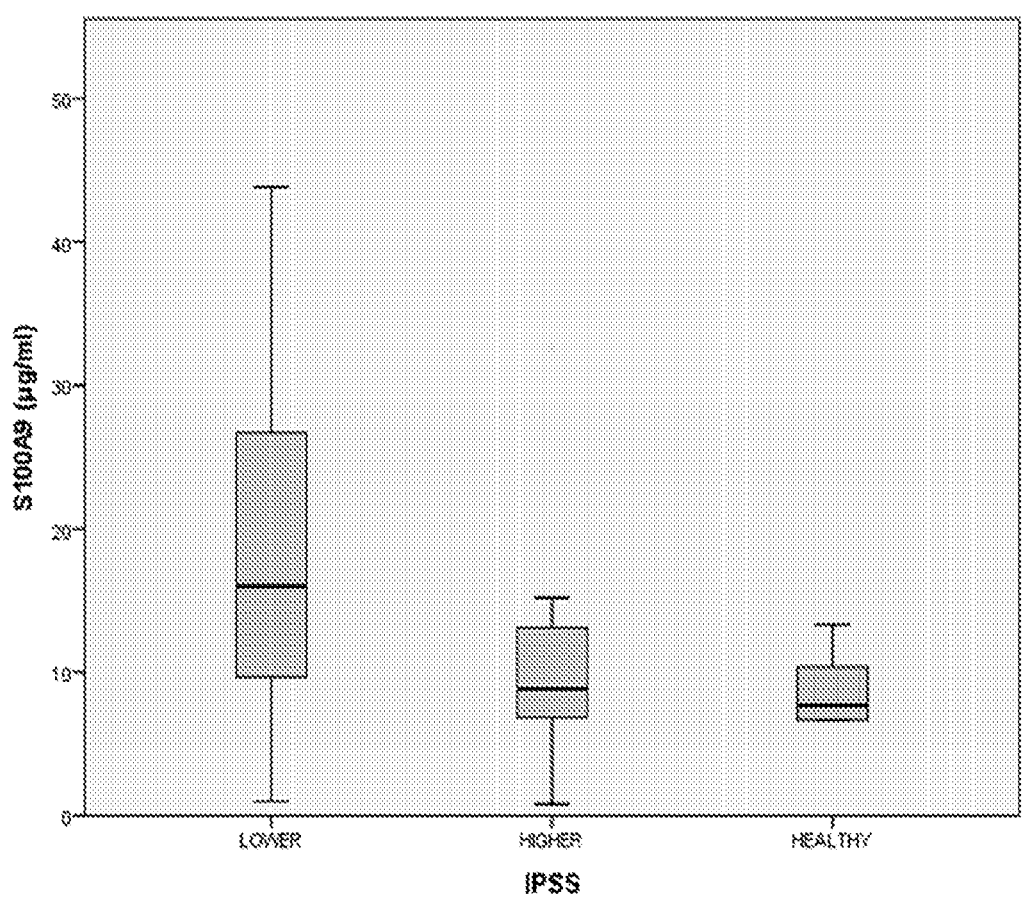
FIG. 22 is a bar graph showing serum s100A9 concentration in healthy patients or patients with lower or higher IPSS score.
Figure 23:
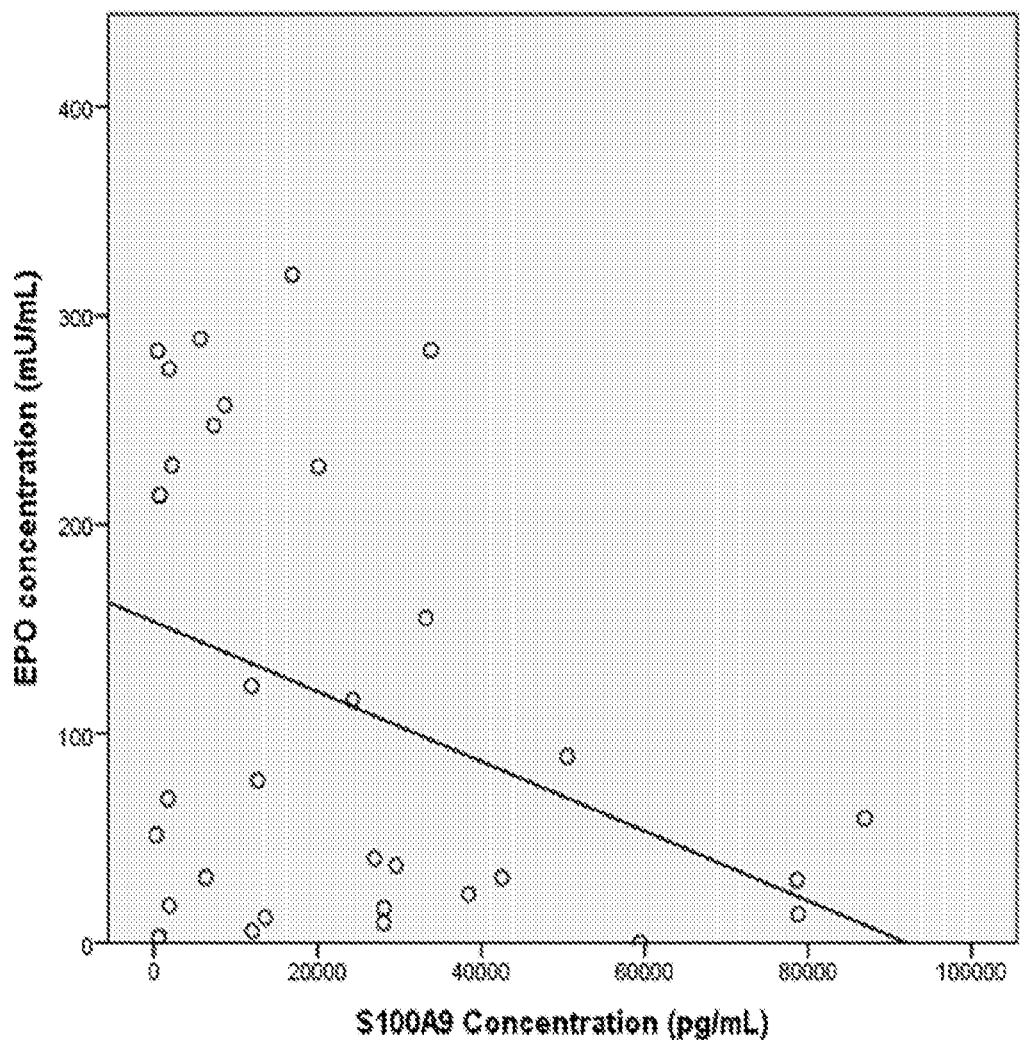
FIG. 23 is a graph showing serum EPO concentration as a function of serum s100A9 concentration.

Serum S100A9 concentration negatively correlates with IPSS Score (FIG. 22). Experiments were conducted with 64 patients (46 in France, 18 at Moffitt Cancer Center) where clinical data was available. ELISA was conducted on serum samples from the patients for s100A9 and EPO. These results were evaluated by Pearson test. A negative correlation between serum EPO and s100A9 was observed (FIG.

Figure 24:
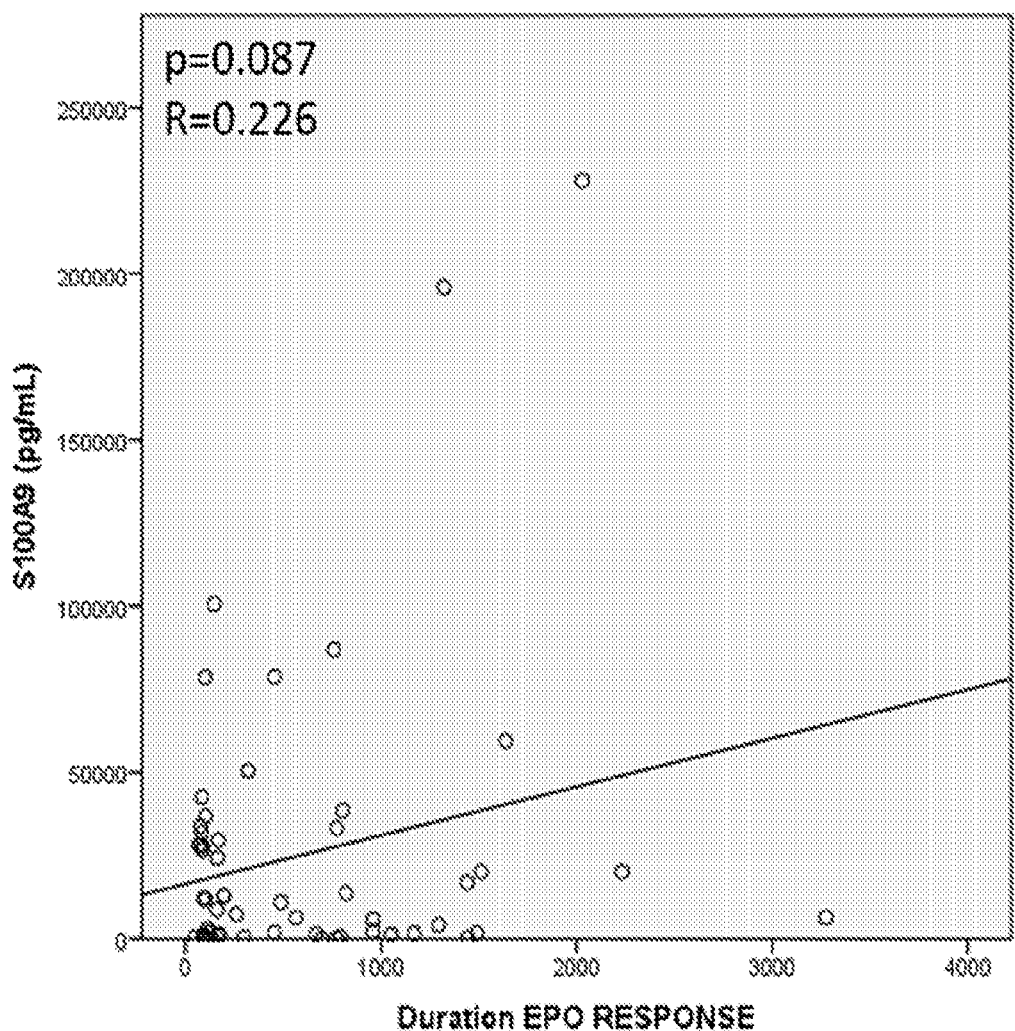
FIG. 24 is a graph showing serum s100A9 concentration as a function of EPO response duration.
Figure 25:
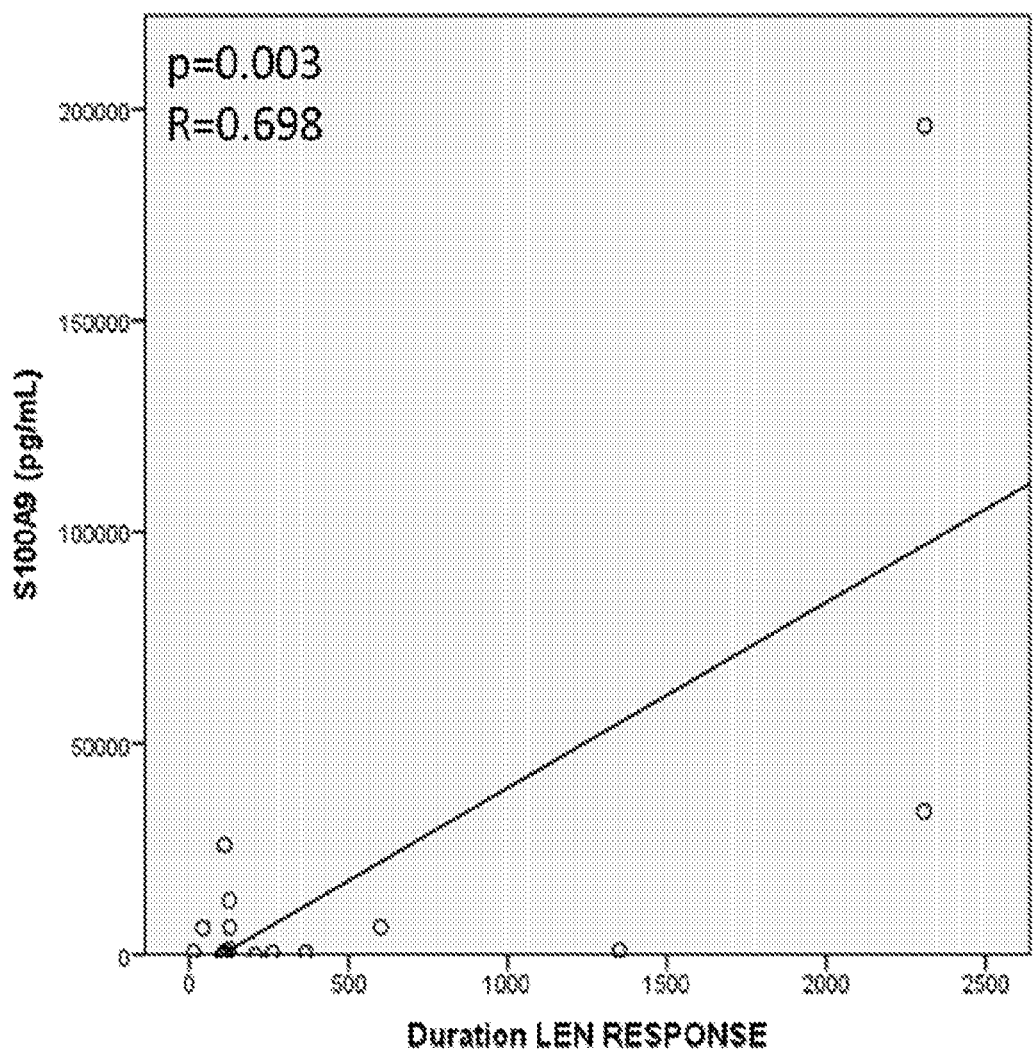
FIG. 25 is a graph showing serum s100A9 concentration as a function of lenalidomide response duration.

23). In addition, serum s100A9 concentration also correlated with the duration of response to EPO (FIG. 24) and lenalidomide (FIG. 25).

Example 3: Pro-Inflammatory Proteins S100A9 and TNFα Suppress Erythropoietin Elaboration in Myelodysplastic Syndromes Introduction Ineffective erythropoiesis in patients with myelodysplastic syndromes (MDS) derives from both intrinsic abnormalities affecting erythropoietin response and extrinsic pressures within the inflammatory bone marrow milieu (Ganan-Gomez I, et al. Leukemia 2015 29(7): 1458-1469). A number of inflammatory cytokines such as tumor necrosis factor-α (TNFα), interleukin (IL)-1β, IL-6 and others, are generated in excess in MDS and are believed to adversely influence hematopoietic stem and progenitor cell (HSPC) survival (Yang L, et al. Cell Mol Life Sci 2015 72(10):1959-1966). Similarly, in a subset of MDS patients, endogenous erythropoietin (Epo) production is deficient, further compromising erythropoietic potential (Valent P. Leuk Res 2008 32(9): 1333-1337). Accumulating evidence implicates innate immune activation in the physiopathology of MDS and the attendant inflammatory microenvironment (Ganan-Gomez I, et al. Leukemia 2015 29(7): 1458-1469). Bone marrow plasma concentrations of the pro-inflammatory, danger-associated molecular pattern (DAMP) protein, S100A9, are profoundly increased in lower risk MDS, which serves as a catalyst directing myeloid-derived suppressor cell expansion (Chen X, et al. J Clin Invest 2013 123(11):4595-4611). S100A9 is a ligand for CD33 and the Toll-like receptor (TLR)-4, which through NF-κB activation, regulates the transcription and cellular elaboration of inflammatory cytokines such as TNFα and IL-1β (Riva M, et al. Immunology 2012 137(2):172-182). Indeed the latter cytokines have been shown to suppress Epo elaboration and have been implicated in the suppression of endogenous Epo production (Faquin W C, et al. Blood 1992 79(8): 1987-1994) in patients with anemia of chronic inflammation (Bertero M T, et al. Haematologica 1997 82(3):375-381). To date, the role of these inflammatory parameters in the regulation of endogenous Epo production and response to erythropoietic treatments in MDS has not been investigated. This Example demonstrates the importance of these inflammatory cytokines as key biological determinants of endogenous Epo production and response to ESA and lenalidomide treatments in patients with non-del (5q) MDS.

Materials and Methods

Reagents and Antibodies

Recombinant S100A9 was generated as previously described (Chen X, et al. J Clin Invest 2013 123(11):4595-4611). TNFα, IL-1β and lipopolysaccharide (LPS) were purchased from Sigma-Aldrich (Saint Louis, Mo., USA). Lenalidomide was purchased from Fisher Scientific (Pittsburgh, Pa., USA). CD33 chimera was constructed as described previously (Chen X, et al. J Clin Invest 2013 123(11):4595-4611; Cannon J P, et al. Methods Mol Biol 2011 748:51-67). NF-κB antibody was purchased from Santa Cruz Biotechnology (Santa Cruz, Calif., USA).

Cell Culture

HepG2 cells, acquired from American Type Culture Collection (ATCC, Manassas, Va.), were grown in EMEM supplemented with 10% FBS and 1% penicillin/streptomycin solution. Cells were maintained at 37° C. under 5% $CO_2$.

ELISA

Quantitation of human S100A9/MRP14 in patient serum and supernatant of the HepG2 cell line was performed using CircuLex S100A9/MRP14 ELISA Kit (MBL, Nagano, Japan). Quantitative measurement of human TNFα and IL-1β from serum patients and supernatant of HepG2 cell line were performed using Human IL-1β ELISA Kit and Human TNFα ELISA Kit (Life Technologies, Carlsbad, Calif., USA). Quantitation of human Epo in patient serum and HepG2 cell line supernatant was performed using Human Erythropoietin ELISA kit (Stemcell Technologies, Vancouver, BC, Canada). All samples were performed in duplicate.

Real-Time Quantitative PCR

RNA was isolated using the RNAeasy Mini Kit (Qiagen, Valencia, Calif., USA) followed by iScript cDNA synthesis (Bio-Rad, Hercules, Calif., USA) and amplification using iQ SYBR Green Supermix (Bio-Rad, Herculed, Calif., USA). The relative level of gene expression for each experimental sample was calculated by the ΔΔCt method. Untreated cells were the experimental control and the housekeeping gene GAPDH was the endogenous control.

Western Blot Analysis

After treatment for 24 h, cells were harvested and lysed in 1×RIPA buffer supplemented with protease and phosphatase inhibitors for classical western blotting. For the nuclear extraction, cells were lysed in ice with buffer A, then pelleted. After removed supernatant (cytoplasmic fraction), pellets were lysed in ice with buffer B and pelleted (nuclear fraction) (Nuclear extraction kit, Abcam, Cambridge, USA). Lysates were pelleted and 50 μg of protein was resolved by SDS-PAGE and transferred to PVDF membranes. The membranes were blocked for 30 min in 5% non-fat dry milk solution in PBST (PBS with 0.1% Tween 20) and incubated with the indicated antibodies. Membranes were developed using ECL according to the manufacturer's protocol (GE Healthcare, Little Chalfont, UK). Densitometry analysis was performed using Image J Software.

Patients and Serum Samples

Serum samples used for ELISA analysis were collected from 4 centers (Taussig Cancer Institute in Cleveland; AOU Careggi, University of Firenze; Saint Louis hospital in Paris; H. Lee Moffitt Cancer Center in Tampa). Peripheral blood mononuclear cells (PBMC) were collected from patients seen at Moffitt Cancer Center All patients were consented on Institutional Review Boards, or equivalent, approved protocols in hematology clinics at each center, and from the Eastern Cooperative Oncology Group (ECOG) E2905 trial (NCT00843882). All routine clinical and biological data were available.

Statistical Analysis

Data are expressed as mean±standard error for continuous variables, or percentage of total for non-continuous variables. Spearman's correlation, Mann-Withney and Jonckheere-Terpstra tests were used for analysis of continuous variables. Chi-square test was used for analysis of non-continuous variables. Differences between the results of comparative tests were considered significant if the two-sided p-value was less than 0.05. All statistical analyses were performed using SPSS v.22 software (IBM SPSS Statistics).

Results

Inflammatory Proteins Suppress Epo Production by HepG2 Cells.

Figure 26A:
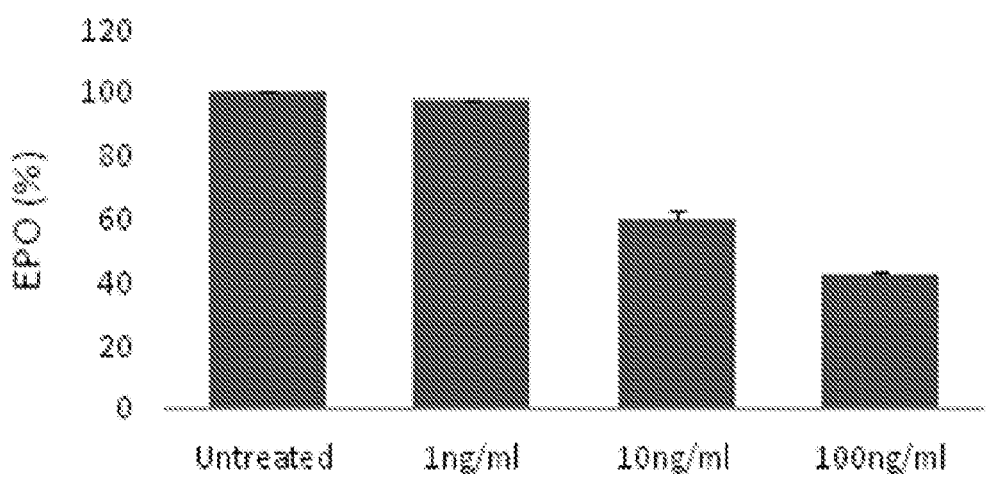
FIGS. 26A to 26C are bar graphs showing the effects of TNFα, IL-1β and S100A9 on Epo elaboration in HepG2 cell line HepG2 cells were stimulated for 24 h with the indicated concentrations of TNFα (FIG. 26A), IL-1β (FIG. 26B) and S100A9 (FIG. 26C) and Epo elaboration was determined by ELISA.
Figure 26B:
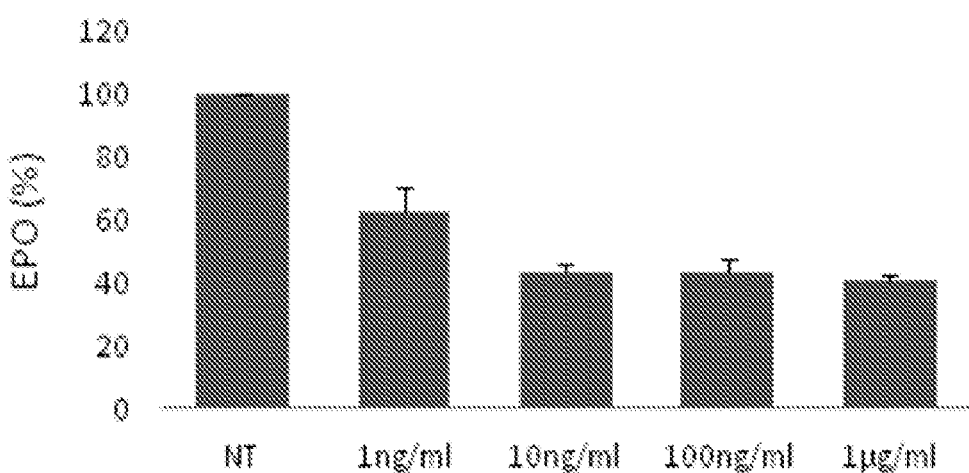
Figure 26C:
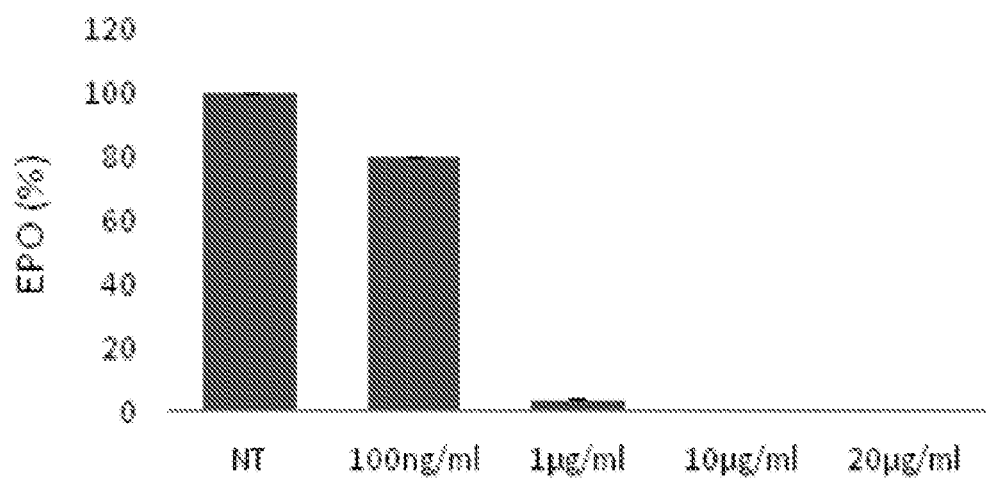

Hepatoma HepG2 cells, which produce Epo under basal conditions (Porwol T, et al. Eur J Biochem 1998 256(1):16-23), were treated with varied concentrations of each of the inflammatory proteins, TNFα, IL-1β or S100A9. After 24 h exposure, we observed a concentration-dependent reduction in Epo elaboration (FIG. 26). At a concentration of 10 ng/ml, TNFα yielded a 40% reduction in Epo elaboration (FIG. 26A), compared to a 60%/reduction following IL-1β incubation (FIG. 26B). Concentrations of 10 to 20 µg/ml of rhS100A9 completely suppressed Epo elaboration, while 1 µg/ml yielded a 95% reduction (FIG. 26C). For subsequent experiments, concentrations of 10 ng/ml of TNFα, 10 ng/ml of IL-1β and 1 µg/ml of S100A9 were employed.

Lenalidomide Mitigates Suppression of Epo Production by S100A9 and TNFα.

Figure 27A:
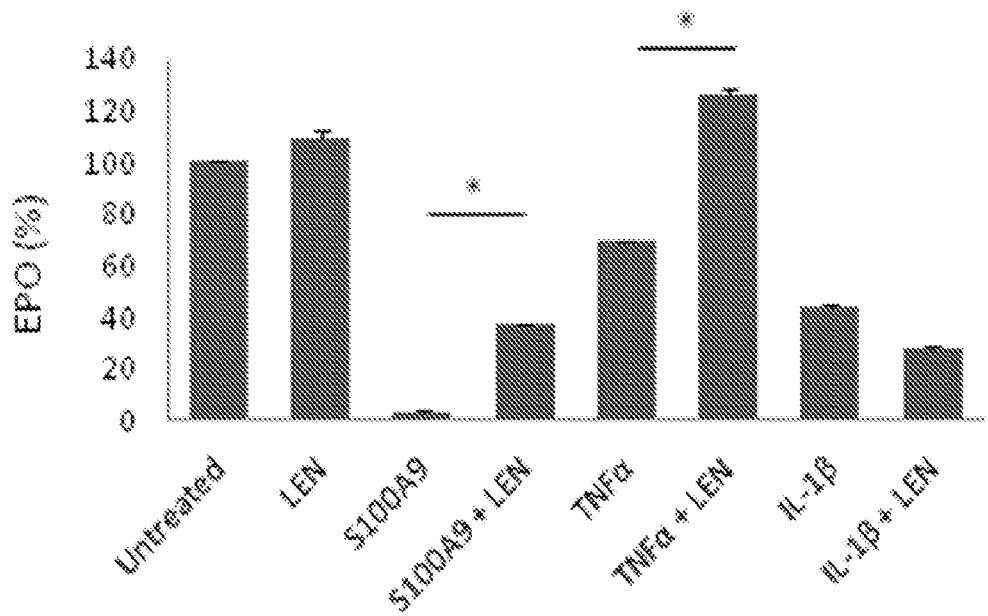
FIGS. 27A to 27C show effect of lenalidomide on Epo elaboration in HepG2 cell line.

The transcription factor NF-κB is activated by TLR ligands and inflammatory cytokines such as TNFα, which like GATA2, is implicated in transcriptional suppression of the Epo transcript (La Ferla K, et al. FASEB J 2002 16(13):1811-1813). HepG2 cells are known to express the S100A9 receptor, TLR4, on the plasma membrane (Hsiao C C, et al. Cancer Lett 2015 368(1): 144-152). Lenalidomide has been reported to suppress NF-κB activation in response to inflammatory cytokine stimulation in lymphocytes and other cell lineages (Crane E, et al. Cancer Invest 2005 23(7):625-634; Galili N, et al. Expert Opin Investig Drugs 2006 15(7):805-813). To determine if lenalidomide can modulate suppression of Epo production by inflammatory proteins, HepG2 cells were treated with 1 µM lenalidomide versus vehicle control 30 minutes prior to TNFα, IL-1β or S100A9 exposure. Lenalidomide significantly, but incompletely reversed suppression of Epo production by S100A9 (95% suppression by S100A9 vs 65% after lenalidomide pre-incubation, p=0.04). Following treatment with TNFα, lenalidomide pre-treatment completely abrogated cytokine suppression of Epo elaboration (TNFα, 30% suppression vs. lenalidomide pre-incubation, 0%, p=0.05, respectively). Lenalidomide had no effect on IL-1β-directed suppression of Epo elaboration (FIG. 27A).

Figure 27B:
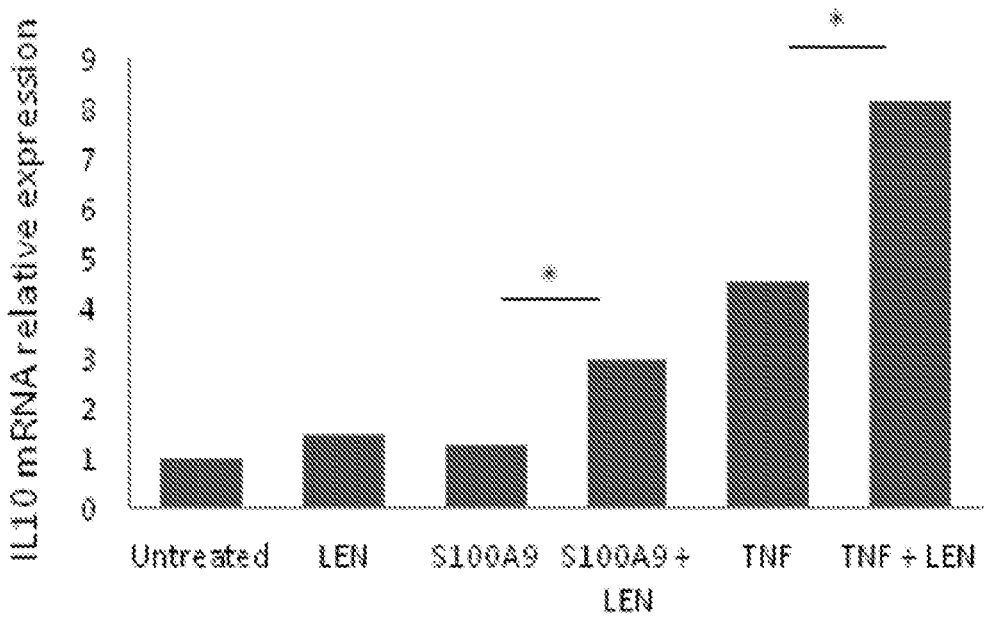

IL-10 is recognized as an anti-inflammatory cytokine secreted by immune cells (Hori S, et al. Science 2003 299(5609):1057-1061). qPCR was performed to determine the effects of the inflammatory proteins and lenalidomide on IL10 gene transcription. Pre-incubation of each inflammatory cytokine with lenalidomide significantly increased IL10 mRNA expression compared to S100A9 or TNFα treatment alone (FIG. 27B). Lenalidomide had no modulatory effect on IL10 gene message following IL-1β treatment.

Figure 27C:
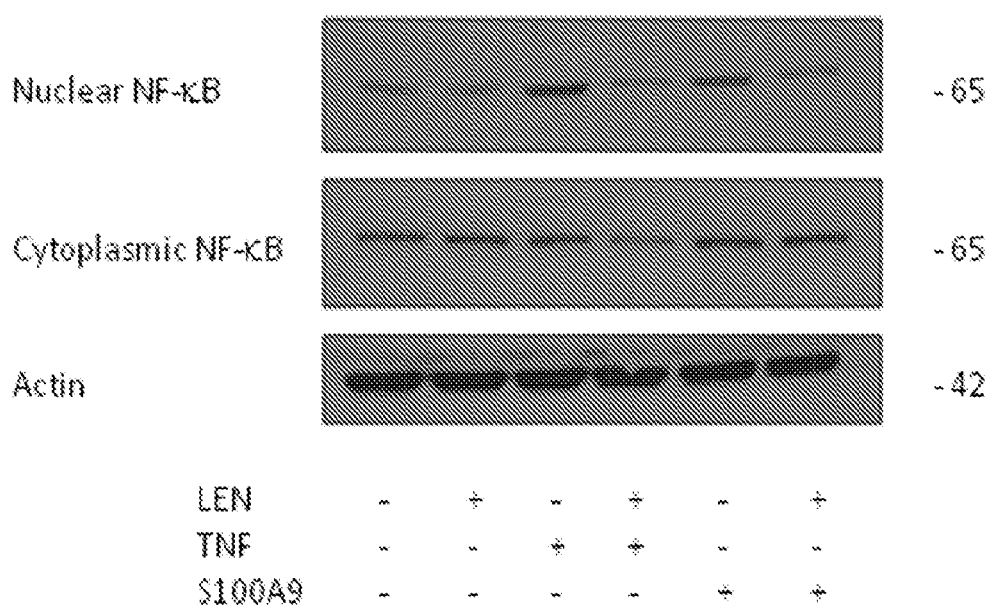
Figure 28A:
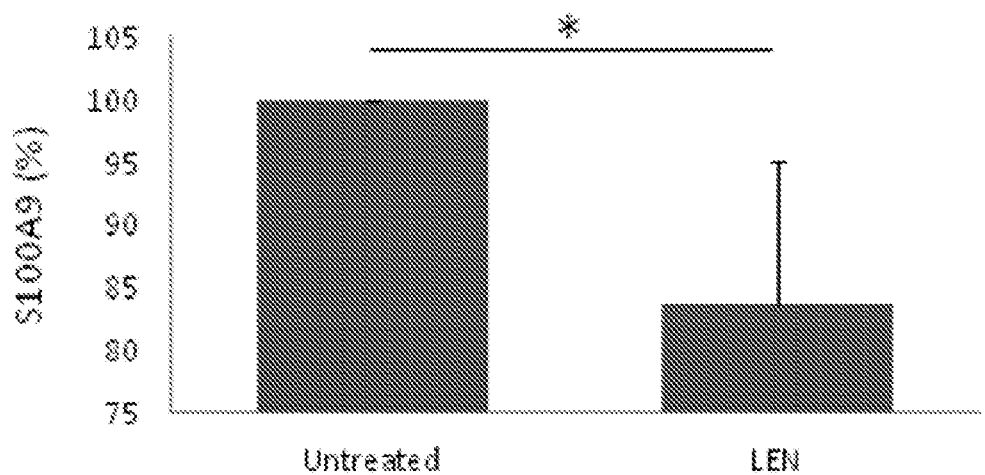
FIGS. 28A and 28B are bar graphs showing effect of lenalidomide on S100A9 and TNFα production in peripheral blood mononuclear cells (PBMC) from MDS patients.
Figure 28B:
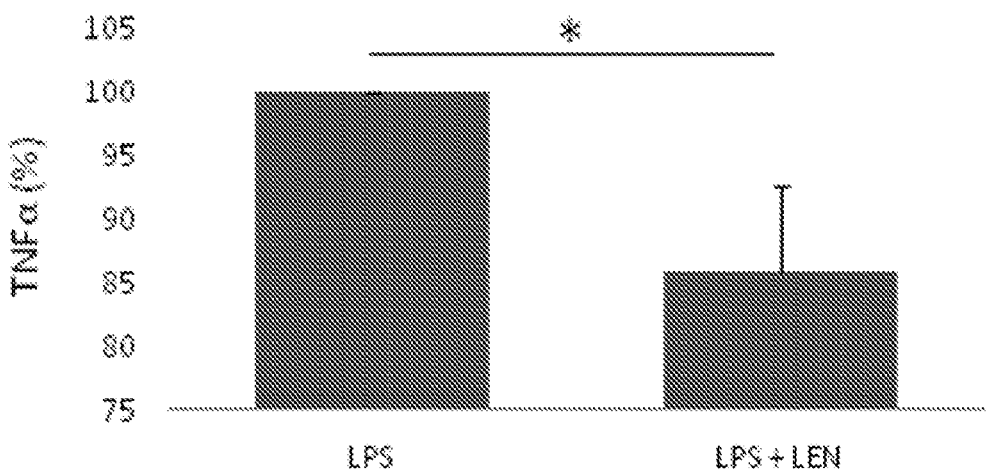

Finally, NF-κB is a key transcription factor involved in S100A9 and TNFα receptor signaling and the transcriptional suppression of Epo mRNA in Epo-producing cells that is modulated by lenalidomide (Zuckerman S H, et al. Immunology 1991 73(4):460-465; Szenajch J, et al. Biochim Biophys Acta 2010 1806(1):82-95; Xu K, et al. J Immunol 2000 164(9):4916-4923). Cytoplasmic and nuclear NF-κB western blotting was therefore performed in HepG2 cells to discern the effect of lenalidomide on inflammatory protein signaling. There was a significant reduction of NF-κB in nuclear fractions after lenalidomide pre-incubation following treatment with S100A9 or TNFα, indicating that lenalidomide suppressed NF-κB activation (FIG. 27C). To confirm the results observed in HepG2 cells, the effects of lenalidomide on steady state production of S100A9 by PBMC isolated from non-del(5q) MDS patients (n=7) was investigated. S100A9 quantification by ELISA showed a significant reduction in S100A9 elaboration after 24 hours exposure to lenalidomide (p=0.01) (FIG. 28A). Similarly, pre-incubation of MDS PBMC with lenalidomide significantly reduced TNFα production induced by LPS (p=0.002).

These findings indicate that S100A9 and TNFα suppression of Epo elaboration is NF-κB-dependent, and modulated by lenalidomide.

Relationship Between Inflammatory Protein and Endogenous Epo Concentration in MDS Patients To validate the regulatory role of these inflammatory proteins on Epo elaboration in vivo, the relationship between serum concentration of these inflammatory cytokines and Epo was assessed in MDS patients with symptomatic anemia. Serum from 316 non-del(5q) MDS patients were analyzed. Median age of the patients was 74.7 years [41-94]. Distribution of International Prognostic Scoring System (IPSS) categories was low, intermediate-1, intermediate-2 and high risk in 38%, 50%, 10% and 2% of patients, respectively; whereas 24%, 38%, 22%, 13% and 3% of patients were very low, low, intermediate, high and very high risk according to the revised-IPSS (IPSS-R) (Table 2). Serum concentrations of Epo, S100A9, S100A8, TNFα and IL-1β were assessed by ELISA. Serum S100A9 concentration was significantly higher in patients with lower risk versus higher risk MDS (12,226 pg/ml vs 240 pg/ml, respectively, p=0.001). No significant differences were observed for TNFα and IL-1β according to IPSS or IPSS-R.

TABLE 2

Patient Demographics and Disease Characteristics

|  | Global cohort n = 316 | Prior ESA Treatment n = 159 | Prior LEN ± ESA Treatment n = 159 |
|---|---|---|---|
| Medan age (range) | 74.7 (41-94) | 74.8 (41-94) | 74.0 (48-85) |
| Sex ratio (F/M) | 212/104 | 105/54 | 110/49 |
| IPSS (%) | | | |
| Low | 38 | 39 | 30 |
| Intermediate 1 | 50 | 47 | 70 |
| Intermediate 2 | 10 | 12 | 0 |
| High | 2 | 2 | 0 |
| IPSS-R (%) | | | |
| Very Low | 24 | 23 | 33 |
| Low | 38 | 39 | 17 |
| Intermediate | 22 | 21 | 50 |
| High | 13 | 14 | 0 |
| Very High | 3 | 3 | 0 |

There was a significant negative correlation between TNFα and Epo concentration (r=−0.164, p=0.006), and between S100A9 and Epo (r=−0.148, p=0.01). There was no discernible relationship between IL-1β and Epo concentration (Table 3A). Moreover, there was a significant positive correlation between the inflammatory protein S100A9 and TNFα (r=0.294, p<0001), S100A9 and IL1β (r=0.180, p=0.002), and IL1β with TNFα concentration (r=0.262, p<0.001) (Table 3B). These findings support the notion that S100A9 and TNFα are generated in parallel and suppress renal Epo elaboration and endocrine response to anemia in non-del(5q) MDS.

TABLE 3A

Correlations between inflammatory proteins and EPO serum concentration.

| Inflammatory parameters | EPO (r; p-value) |
|---|---|
| S100A9 | (−0.148; 0.01) |
| TNFα | (−0.164; 0.006) |
| IL1β | (−0.003; 0.96) |

TABLE 3B

Relationship between inflammatory proteins.

|       | S100A9           | TNFα              |
|-------|------------------|-------------------|
| S100A9|                  | (0.294; <0.0001)  |
| TNFα  | (0.294; <0.0001) |                   |
| IL1β  | (0.180; 0.002)   | (0.262; <0.0001)  |

Figure 29A:
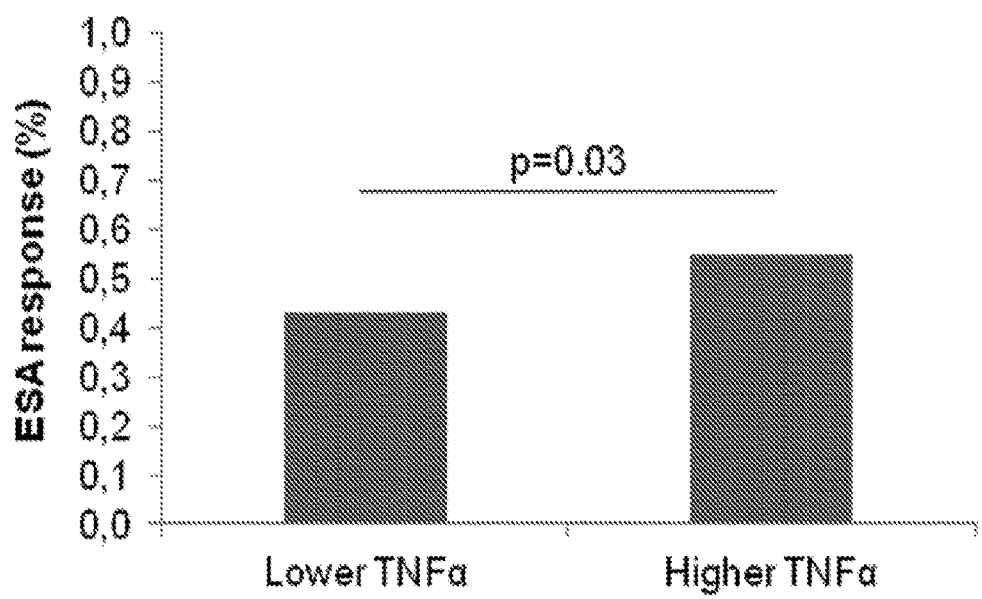
FIGS. 29A and 29B are bar graphs showing relationship between serum concentration of inflammatory proteins and response to ESA (FIG. 29A) or lenalidomide (FIG. 29B).
Figure 29B:
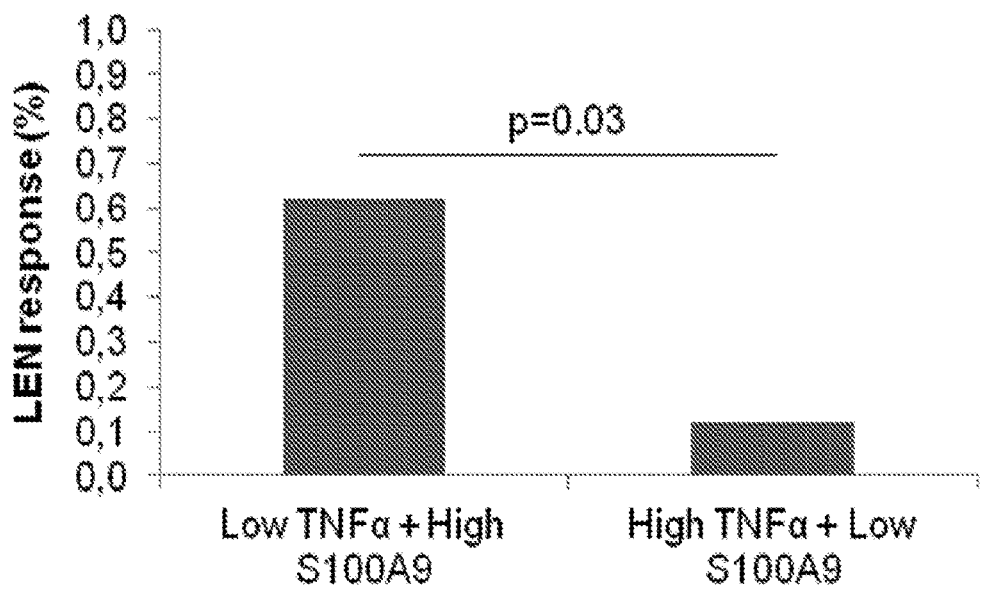

Relationship Between Inflammatory Protein Concentration and Response to Treatment with Erythropoietic Agents Within the cohort of non-del(5q) MDS patients, 159 were obtained prior to ESA treatment and 159 prior to lenalidomide±Epo treatment (Table 2). ESA responders had a significantly higher serum TNFα concentration than non-responders (8.37 pg/ml vs. 3.79 pg/ml, p=0.03) with a corresponding significantly lower Epo concentration in ESA responders (36 mU/ml vs 113 mU/ml, p<0.0001). Erythroid response rate was 43% versus 55% in patients with low vs high TNFα concentration, respectively (FIG. 29A). There was no significant relationship between S100A9 serum concentration and Epo response. Finally, among patients treated with lenalidomide or lenalidomide+ Epo, responding patients had a significantly lower serum TNFα concentration (p=0.02) while there was no relationship to S100A9 concentration (p=0.21). Comparing response to lenalidomide according to low (below the median) and high (above the median) serum TNFα concentration, there was a significant difference in erythroid response rate (64% vs 14% for patients with low TNFα vs. high serum concentration, respectively; p=0.02). In parallel, there was a trend toward a high S100A9 concentration in lenalidomide responders vs low S100A9 concentration in lenalidomide non-responders (p=0.10). Upon analyzing the interaction between TNFα and S100A9 concentration and response to lenalidomide treatment, patients with low TNFα and high S100A9 concentrations had a higher erythroid response rate than patients with high TNFα and low S100A9 (62% vs 12%, respectively; p=0.03) (FIG. 29B).

Discussion

Pro-inflammatory cytokines have long been implicated as key effectors of anemia in disorders of chronic inflammation and malignancy (Morceau F, et al. Mediators Inflamm 2009 2009:405016). The pathogenesis of the ineffective erythropoiesis in MDS in particular is multifactorial, including abnormalities inherent to the neoplastic clone as well as the inflammatory bone marrow microenvironment (Calado R T. Seminars in oncology 2011 38(5):667-672). Inflammatory cytokines such as IL-1β, interferon-γ, transforming growth factor-β (TGFβ) and TNF-α directly inhibit erythroid progenitor colony forming capacity in vitro and impair iron turnover (Wang C Q, et al J Cell Physiol 1995 162(1):134-138; Felli N, et al. J Immunol 2005 175(3):1464-1472; Taniguchi S, et al. Blood 1997 90(6):2244-2252). Moreover, both IL-1β and TNF-α suppress erythropoietin gene expression and protein secretion in a NF-κB-dependent fashion (Simard J C, et al. PLoS One 2013 8(8):e72138), which has been implicated in the disproportionately low endogenous erythropoietin production in response to the anemia of inflammation. In a subset of lower risk MDS patients who are responsive to treatment with recombinant erythropoietin, renal erythropoietin production is suppressed with a corresponding reduction in serum erythropoietin concentration. The precise physiological events that impair erythropoietin production in lower risk MDS, however, remained unexplored. The disclosed investigations show that S100A9, a myeloid derived inflammatory protein produced in excess in MDS, directly suppresses erythropoietin transcription and elaboration in HepG2 hepatoma cells, analogous to the actions of TNFα (Chen X, et al. J Clin Invest 2013 123(11): 4595-4611). Moreover, S100A9 serves as a key coordinator of the inflammatory response by inducing the secretion of TNF-α, IL-6, IL-8, and IL-1β via TLR4-dependent activation of NF-κB (Simard J C, et al. PLoS One 2013 8(8): e72138; Chernov A V, et al. J Biol Chem 2015 290(18): 11771-11784). The disclosed findings support the notion that these inflammatory cytokines similarly suppress erythropoietin production in vivo in lower risk MDS patients. Serum Epo concentration inversely correlated with S100A9 and TNFα concentrations. Furthermore, serum TNFα concentration was significantly higher in patients responding to treatment with recombinant erythropoietin compared to non-responders (p=0.03). Of particular interest, lenalidomide suppressed nuclear translocation of NF-κB to mitigate suppression of Epo production in HepG2 cells by both S100A9 and TNFα. The ability of lenalidomide to modulate cytokine activation may not only reduce progenitor cell injury, but also relieve repression of Epo elaboration and endocrine response to anemia in MDS. Serum concentration of TNFα was significantly lower and serum concentration of S100A9 was higher in lenalidomide responding patients (p=0.03). Together, these findings indicate that S100A9 and its transcriptional target, TNFα, directly suppress Epo elaboration and endocrine response to anemia in MDS and may be useful biomarkers for response to treatment with lenalidomide or recombinant erythropoietin that merit further investigation. More importantly, these findings suggest that therapeutic strategies that either neutralize or suppress S100A9 may improve erythropoiesis in lower risk MDS by suppressing inflammatory cytokine generation and restoring endocrine erythropoietin response to anemia.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for predicting the responsiveness of a patient with a myelodysplastic syndrome (MDS) to lenalidomide treatment, erythropoietin treatment, or a combination thereof, comprising assaying a biological sample from the patient for s100A9 levels, TNFα levels, or a combination thereof, wherein elevated levels of s100A9 in the biological sample is an indication that the patient will be responsive, and wherein reduced levels of TNFα in the biological sample is an indication that the patient will be responsive, detecting elevated s100A9 levels, reduced TNFα levels, or a combination thereof, and treating the patient with lenalidomide, erythropoietin, or a combination thereof.

2. The method of claim 1, wherein the patient has anemia.

3. The method of claim 1, wherein the patient has non-del5q MDS.

4. The method of claim 1, wherein the biological sample is a blood, serum, or plasma sample.

5. The method of claim 1, wherein the patient is treated with erythropoietin and granulocyte colony-stimulating factor (GCSF).

6. A method for diagnosing a myelodysplastic syndrome (MDS), Cryopyrin-Associated Periodic Syndromes (CAPS), or an autoimmune disorder in a subject, comprising assaying a sample from the subject to detect s100A9 protein levels, wherein an increase in s100A9 protein levels in the sample compared to a control is an indication of MDS, CAPS, or autoimmune disorder in the subject, detecting an increase in s100A9 protein levels, and treating the subject for MDS with a therapeutically effective amount of lenalidomide, erythropoietin, or a combination thereof.

7. The method of claim 6, wherein the sample comprises hematopoietic stem/progenitor cells (HSPC).

8. The method of claim 6, wherein the sample comprises a bone marrow sample.

9. The method of claim 6, further comprising predicting from the detection of increased s100A9 protein levels whether the subject has low-risk or high-risk MDS.

* * * * *